US012740550B2

(12) United States Patent
Liu et al.

(10) Patent No.: US 12,740,550 B2
(45) Date of Patent: Sep. 22, 2026

(54) GENETICALLY MODIFIED NON-HUMAN ANIMAL WITH HUMAN OR CHIMERIC TFR1

(71) Applicant: Biocytogen Pharmaceuticals (Beijing) Co., Ltd., Beijing (CN)

(72) Inventors: Chang Liu, Beijing (CN); Chengzhang Shang, Beijing (CN); Xiaofei Zhou, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 371 days.

(21) Appl. No.: 18/566,898

(22) PCT Filed: Jul. 15, 2022

(86) PCT No.: PCT/CN2022/105924
§ 371 (c)(1),
(2) Date: Dec. 4, 2023

(87) PCT Pub. No.: WO2023/284850
PCT Pub. Date: Jan. 19, 2023

(65) Prior Publication Data

US 2024/0268361 A1 Aug. 15, 2024

(30) Foreign Application Priority Data

Jul. 16, 2021 (CN) ......................... 202110808740.8
Oct. 25, 2021 (CN) ......................... 202111238943.4

(51) Int. Cl.
*A01K 67/0278* (2024.01)
*C07K 14/705* (2006.01)

(52) U.S. Cl.
CPC .... *A01K 67/0278* (2013.01); *C07K 14/70582* (2013.01); *A01K 2207/12* (2013.01); *A01K 2207/15* (2013.01); *A01K 2217/052* (2013.01); *A01K 2227/105* (2013.01); *A01K 2267/0331* (2013.01)

(58) Field of Classification Search
CPC ........... A01K 67/0278; A01K 2217/07; G01N 2500/00
See application file for complete search history.

(56) References Cited

U.S. PATENT DOCUMENTS

| | | | |
|---|---|---|---|
| 10,143,187 | B2 | 12/2018 | Dennis et al. |
| 10,912,287 | B2 | 2/2021 | Shen et al. |
| 2013/0045206 | A1 | 2/2013 | Poul et al. |
| 2015/0106961 | A1 | 4/2015 | Rojas et al. |
| 2016/0208008 | A1 | 7/2016 | Alper |
| 2018/0237496 | A1 | 8/2018 | Chen et al. |
| 2020/0154684 | A1 | 5/2020 | Mujica et al. |
| 2021/0051928 | A1 | 2/2021 | Shen et al. |

FOREIGN PATENT DOCUMENTS

| | | | |
|---|---|---|---|
| CN | 107287204 | | 10/2017 |
| CN | 109735498 | | 5/2019 |
| CN | 110382526 | | 10/2019 |
| CN | 112458117 | A | 3/2021 |
| CN | 112501124 | A | 3/2021 |
| CN | 112725379 | | 4/2021 |
| EP | 3561058 | A1 | 10/2019 |
| JP | 2020508049 | A | 3/2020 |
| JP | 2020510418 | A | 4/2020 |
| WO | WO 2018001241 | | 1/2018 |
| WO | WO 2018041118 | | 3/2018 |
| WO | WO 2018041119 | | 3/2018 |
| WO | WO 2018041121 | | 3/2018 |
| WO | WO 2018086583 | | 5/2018 |
| WO | WO 2018086594 | | 5/2018 |
| WO | WO 2018124107 | A1 | 7/2018 |
| WO | WO2018152285 | | 8/2018 |
| WO | WO 2019072241 | | 4/2019 |
| WO | WO 2020103882 | | 5/2020 |
| WO | WO 2020104479 | A1 | 5/2020 |
| WO | WO 2020125763 | | 6/2020 |

OTHER PUBLICATIONS

AL-Rafaei (Heliyon 6 (2020) e03221, 6 pages) f.*
Iocopetta (Cell, vol. 54, 485-489, Aug. 12, 1988).*
Rothenberger (1987, Cell, 49:, 423-431).*
GenBank: AAH01188.1 (NIH National Library of Medicine. Oct. 4, 2003, TFRC protein [*Homo sapiens*]—Protein—NCBI, accessed Mar. 13, 2026.*
Auerbach et al., Establishment and chimera analysis of 129/SvEv- and C57BL/6-derived mouse embryonic stem cell lines, Bio Techniques, Nov. 2000, 29(5):1024-1032.
Candelaria et al., "Antibodies targeting the transferrin receptor 1 (TfR1) as direct anti-cancer agents," Frontiers in Immunology, Mar. 2021, vol. 12, Article 607692, pp. 1-21.
Festing et al., "Revised nomenclature for strain 129 mice," Mammalian Genome, 1999, 10:836.
GenBank Accession No. NC_000003.12, "*Homo sapiens* chromosome 3, GRCh38.p13 Primary Assembly," May 29, 2020, 3 pages.
GenBank Accession No. NC_000082.7, "Mus musculus strain C57BL/6J chromosome 16, GRCm39," Sep. 22, 2020, 2 pages.
GenBank Accession No. NM_003234.4, "*Homo sapiens* transferrin receptor (TFRC), transcript variant 1, mRNA," Jul. 6, 2021, 7 pages.
GenBank Accession No. NM_011638.4, "Mus musculus transferrin receptor (Tfrc), transcript variant 1, mRNA," Apr. 20, 2021, 7 pages.
GenBank Accession No. NP_003225.2, "transferrin receptor protein 1 isoform 1 [*Homo sapiens*]," Jul. 9, 2020, 4 pages.

(Continued)

*Primary Examiner* — Valarie E Bertoglio
(74) *Attorney, Agent, or Firm* — Fish & Richardson P.C.

(57) ABSTRACT

Provided are genetically modified non-human animals that express a human or chimeric (e.g., humanized) TFR1, and methods of use thereof.

13 Claims, 12 Drawing Sheets

Specification includes a Sequence Listing.

(56) References Cited

OTHER PUBLICATIONS

GenBank Accession No. NP_035768.1, "transferrin receptor protein 1 [Mus musculus]," Jul. 12, 2020, 4 pages.
GenBank Accession No. NP_073203.1, "transferrin receptor protein 1 [Rattus norvegicus]," Jun. 7, 2020, 3 pages.
International Preliminary Report on Patentability in International Appln. No. PCT/CN2022/105924, mailed on Jan. 25, 2024, 6 pages.
International Search Report and Written Opinion in International Appln. No. PCT/CN2022/105924, mailed on Oct. 10, 2022, 12 pages.
Ito et al., "NOD/SCID/γc null mouse: an excellent recipient mouse model for engraftment of human cells," Blood, Nov. 1, 2002, 110(9):3175-3182.
Shen et al., "Transferrin receptor 1 in cancer: a new sight for cancer therapy," American Journal of Cancer Research, 2018, available online Jun. 1, 2018, 8(6):916-931.
UniProt Accession No. P02786, "Transferrin receptor protein 1," Jun. 17, 2020, 16 pages.
UniProt Accession No. Q62351, "Transferrin receptor protein 1," Jun. 17, 2020, 6 pages.
Yin et al., "Delivery technologies for genome editing," Nature Reviews Drug Discovery, Jun. 2017, 16:387-399.
Yu et al., "Therapeutic bispecific antibodies cross the blood-brain barrier in nonhuman primates," Science Translational Medicine, Nov. 2014, vol. 6, No. 261, Article 261ra154, 10 pages.
Extended European Search Report in European Appln. No. 22841483.5, mailed on Apr. 29, 2025, 12 pages.
Sonoda et al., "A Blood-Brain-Barrier-Penetrating Anti-human Transferrin Receptor Antibody Fusion Protein for Neuronopathic Mucopolysaccharidosis II," and Supplemental Information, Molecular Therapy, May 2018, 26(5):1366-1374 (21 pages including the supplemental material).

* cited by examiner

Marker +/+ H/H $H_2O$

FIG. 9

| Score | Expect | Method | Identities | Positives | Gaps |
| --- | --- | --- | --- | --- | --- |
| 1237 bits(3201) | 0.0 | Compositional matrix adjust. | 587/764(77%) | 668/764(87%) | 5/764(0%) |

```
HUMAN  1    MMDQARSAFSNLFGGEPLSYTRFSLARQVDGDNSHVEMKLAVDEEENADNNTKANVTKPK  60
            MMDQARSAFSNLFGGEPLSYTRFSLARQVDGDNSHVEMKLA DEEENADNN KA+V KPK
MOUSE  1    MMDQARSAFSNLFGGEPLSYTRFSLARQVDGDNSHVEMKLAADEEENADNNMKASVRKPK  60

HUMAN  61   RCSGSICYGTIAVIVFFLIGFMIGYLGYCKGVEPKTECERLAGTESPVREEP--GEDFPA  118
            R +G +C+  IA+++FFLIGFM GYLGYCK VE K EC +LA TE   + E    ED P
MOUSE  61   RFNGRLCFAAIALVIFFLIGFMSGYLGYCKRVEQKEECVKLAETEETDKSETMETEDVPT  120

HUMAN  119  ARRLYWDDLKRKLSEKLDSTDFTGTIKLLNENSYVFREAGSQKDENLALYVENQFREFKL  178
            + RLYW DLK  LSEKL+S +F  TIK L++N+Y FREAGSQKDE+LA Y+ENQF EFK
MOUSE  121  SSRLYWADLKTLLSEKLNSIEFADTIKQLSQNTYTFREAGSQKDESLAYYIENQFHEFKF  180

HUMAN  179  SKVWRDQHFVKIQVKDS-AQNSVIIVDKNGRLVYLVENPGGYVAYSKAATVTGKLVHANF  237
            SKVWRD+H+VKIQVK S  QN V IV  NG L   VE+P GYVA+SK   V+GKLVHANF
MOUSE  181  SKVWRDEHYVKIQVKSSIGQNMVTIVQSNGNLD-FVESPEGYVAFSKPTEVSGKLVHANF  239

HUMAN  238  GTKKDFEDLYTPVNGSIVIVRAGKITFAEKVANAESLNAIGVLIYMDQTKFPIVNAELSF  297
            GTKKDFE+L   VNGS+VIVRAG+ITFAEKVANA+S NAIGVLIYMD+ KFP+V A+L+
MOUSE  240  GTKKDFEELSYSVNGSLVIVRAGEITFAEKVANAQSFNAIGVLIYMDKNKFPVVEADLAL  299

HUMAN  298  FGHAHLGTGDPYTPGFPSFNHTQFPPSRSSGLPNIPVQTISRAAAEKLFGNMEGDCPSDW  357
            FGHAHLGTGDPYTPGFPSFNHTQFPPS+SSGLPNIPVQTISRAAAEKLFG MEG CP+ W
MOUSE  300  FGHAHLGTGDPYTPGFPSFNHTQFPPSQSSGLPNIPVQTISRAAAEKLFGKMEGSCPARW  359

HUMAN  358  KTDSTCRMVTSESKNVKLTVSNVLKEIKILNIFGVIKGFVEPDHYVVVGAQRDAWGPG-A  416
              DS+C++  S+++NVKL V NVLKE +ILNIFGVIKG+ EPD YVVVGAQRDA G G A
MOUSE  360  NIDSSCKLELSQNQNVKLIVKNVLKERRILNIFGVIKGYEEPDRYVVVGAQRDALGAGVA  419

HUMAN  417  AKSGVGTALLLKLAQMFSDMVLKDGFQPSRSIIFASWSAGDFGSVGATEWLEGYLSSLHL  476
            AKS VGT LLLKLAQ+FSDM+ KDGF+PSRSIIFASW+AGDFG+VGATEWLEGYLSSLHL
MOUSE  420  AKSSVGTGLLLKLAQVFSDMISKDGFRPSRSIIFASWTAGDFGAVGATEWLEGYLSSLHL  479
```

FIG. 9 (Continued)

```
HUMAN   477   KAFTYINLDKAVLGTSNFKVSASPLLYTLIEKTMQNVKHPVTGQFLYQDSNWASKVEKLT   536
              KAFTYINLDK VLGTSNFKVSASPLLYTL+ K MQ+VKHPV G+ LY+DSNW SKVEKL+
MOUSE   480   KAFTYINLDKVVLGTSNFKVSASPLLYTLMGKIMQDVKHPVDGKSLYRDSNWISKVEKLS   539

HUMAN   537   LDNAAFPFLAYSGIPAVSFCFCEDTDYPYLGTTMDTYKELIERIPELNKVARAAAEVAGQ   596
               DNAA+PFLAYSGIPAVSFCFCED DYPYLGT +DTY+ L +++P+LN++ R AAEVAGQ
MOUSE   540   FDNAAYPFLAYSGIPAVSFCFCEDADYPYLGTRLDTYEALTQKVPQLNQMVRTAAEVAGQ   599

HUMAN   597   FVIKLTHDVELNLDYERYNSQLLSFVRDLNQYRADIKEMGLSLQWLYSARGDFFRATSRL   656
               +IKLTHDVELNLDYE YNS+LLSF++DLNQ++ DI++MGLSLQWLYSARGD+FRATSRL
MOUSE   600   LIIKLTHDVELNLDYEMYNSKLLSFMKDLNQFKTDIRDMGLSLQWLYSARGDYFRATSRL   659

HUMAN   657   TTDFGNAEKTDRFVMKKLNDRVMRVEYHFLSPYVSPKESPFRHVFWGSGSHTLPALLENL   716
              TTDF NAEKT+RFVM+++NDR+M+VEYHFLSPYVSP+ESPFRH+FWGSGSHTL AL+ENL
MOUSE   660   TTDFHNAEKTNRFVMREINDRIMKVEYHFLSPYVSPRESPFRHIFWGSGSHTLSALVENL   719

HUMAN   717   KLRKQNNGAFNETLFRNQLALATWTIQGAANALSGDVWDIDNEF   760
              KLR++N  AFNETLFRNQLALATWTIQG ANALSGD+W+IDNEF
MOUSE   720   KLRQKNITAFNETLFRNQLALATWTIQGVANALSGDIWNIDNEF   763
```

FIG. 10

| Score | Expect | Method | Identities | Positives | Gaps |
|---|---|---|---|---|---|
| 1245 bits(3222) | 0.0 | Compositional matrix adjust. | 581/762(76%) | 674/762(88%) | 3/762(0%) |

```
HUMAN  1    MMDQARSAFSNLFGGEPLSYTRFSLARQVDGDNSHVEMKLAVDEEENADNNTKANVTKPK  60
            MMDQARSAFSNLFGGEPLSYTRFSLARQVDGDNSHVEMKLA DEEENAD+N KA+V KPK
RAT    1    MMDQARSAFSNLFGGEPLSYTRFSLARQVDGDNSHVEMKLAADEEENADSNMKASVRKPK  60

HUMAN  61   RCSGSICYGTIAVIVFFLIGFMIGYLGYCKGVEPKTECERLAGTESPVREEPGED--FPA  118
            R +G +C+ TIAV++FFLIGFMIGYLGYCK VE K EC RLA  E   + E  E    P
RAT    61   RFNGRLCFATIAVVIFFLIGFMIGYLGYCKRVEQKEECVRLAEAEEADKSENDETEYVPK  120

HUMAN  119  ARRLYWDDLKRKLSEKLDSTDFTGTIKLLNENSYVPREAGSQKDENLALYVENQFREFKL  178
            + RL+W DLK  LSEKL+S +FT  IK L++N+Y PREAGSQKDENLA Y+EN F +FK
RAT    121  SSRLFWADLKTLLSEKLNSIEFTDIIKQLSQNTYTPREAGSQKDENLAYYIENLFHDFKF  180

HUMAN  179  SKVWRDQHFVKIQVKDSAQNSVIIVDKNGRLVYLVENPGGYVAYSKAATVTGKLVHANFG  238
            SKVWRD+H+VKIQVK+S   +++ ++ +G  +  VE P GYVA+SKA  VTGKLVHANFG
RAT    181  SKVWRDEHYVKIQVKNSVSQNLVTIN-SGSNIDPVEAPEGYVAFSKAGEVTGKLVHANFG  239

HUMAN  239  TKKDFEDLYTPVNGSIVIVRAGKITFAEKVANAESLNAIGVLIYMDQTKFPIVNAELSFF  298
            TKKDFE+L   VNGS+VIVRAGKITFAEKVANA+S NAIGVLIYMD+  FP+V A+L FF
RAT    240  TKKDFEELNYSVNGSLVIVRAGKITFAEKVANAQSFNAIGVLIYMDRNTFPVVEADLQFF  299

HUMAN  299  GHAHLGTGDPYTPGFPSFNHTQFPPSRSSGLPNIPVQTISRAAAEKLFGNMEGDCPSDWK  358
            GHAHLGTGDPYTPGFPSFNHTQFPPS+SSGLP+IPVQTISRAAAEKLF NMEG+CP  W
RAT    300  GHAHLGTGDPYTPGFPSFNHTQFPPSQSSGLPSIPVQTISRAAAEKLFKNMEGNCPPSWN  359

HUMAN  359  TDSTCRMVTSESKNVKLTVSNVLKEIKILNIFGVIKGFVEPDHYVVVGAQRDAWGPGAAK  418
             DS+C++  S+++NVKLTV+NVLKE +ILNIFGVIKG+ EPD Y+VVGAQRDAWGPG AK
RAT    360  IDSSCKLELSQNQNVKLTVNNVLKETRILNIFGVIKGYEEPDRYIVVGAQRDAWGPGVAK  419

HUMAN  419  SGVGTALLLKLAQMFSDMVLKDGFQPSRSIIFASWSAGDFGSVGATEWLEGYLSSLHLKA  478
            S VGT LLLKLAQ+FSDM+ KDGF+PSRSIIFASW+AGD+G+VGATEWLEGYLSSLHLKA
RAT    420  SSVGTGLLLKLAQVFSDMISKDGFRPSRSIIFASWTAGDYGAVGATEWLEGYLSSLHLKA  479
```

FIG. 10 (Continued)

```
HUMAN  479  FTYINLDKAVLGTSNFKVSASPLLYTLIEKTMQNVKHPVTGQFLYQDSNWASKVEKLTLD  538
            FTYINLDK VLGTSNFKVSASPLLYTL+ K MQ+VKHP+ G++LY+DSNW SK+E+L+LD
RAT    480  FTYINLDKVVLGTSNFKVSASPLLYTLMGKIMQDVKHPIDGKYLYRDSNWISKIEELSLD  539

HUMAN  539  NAAFPFLAYSGIPAVSFCFCEDTDYPYLGTTMDTYKELIERIPELNKVARAAAEVAGQFV  598
            NAAFPFLAYSGIPAVSFCFCED DYPYLGT +DTY+ LI+++P+LN++ R AAEVAGQF+
RAT    540  NAAFPFLAYSGIPAVSFCFCEDEDYPYLGTKLDTYEILIQKVPQLNQMVRTAAEVAGQFI  599

HUMAN  599  IKLTHDVELNLDYERYNSQLLSFVRDLNQYRADIKEMGLSLQWLYSARGDFFRATSRLTT  658
            IKLTHD+EL LDYE YNS+LLSF++DLNQ++ADIK+MGLSLQWLYSARGD+FRATSRLTT
RAT    600  IKLTHDIELTLDYEMYNSKLLSFMKDLNQFKADIKDMGLSLQWLYSARGDYFRATSRLTT  659

HUMAN  659  DFGNAEKTDRFVMKKLNDRVMRVEYHFLSPYVSPKESPFRHVFWGSGSHTLPALLENLKL  718
            DF NAEKT+RFVM+++NDR+M+VEYHFLSPYVSP+ESPFRH+FWGSGSHTL AL+ENL+L
RAT    660  DFHNAEKTNRFVMREINDRIMKVEYHFLSPYVSPRESPFRHIFWGSGSHTLSALVENLRL  719

HUMAN  719  RKQNNGAFNETLFRNQLALATWTIQGAANALSGDVWDIDNEF  760
            R++N  AFNETLFRNQLALATWTIQG ANALSGD+W+IDNEF
RAT    720  RQKNITAFNETLFRNQLALATWTIQGVANALSGDIWNIDNEF  761
```

GENETICALLY MODIFIED NON-HUMAN ANIMAL WITH HUMAN OR CHIMERIC TFR1

CLAIM OF PRIORITY

This application is a National Phase Application under 35 U.S.C. § 371 of International Application No. PCT/CN2022/105924, filed on Jul. 15, 2022, which claims the benefit of Chinese Patent Application application No. 202110808740.8, filed on Jul. 16, 2021 and Chinese Patent Application application No. 202111238943.4, filed on Oct. 25, 2021. The entire contents of the foregoing applications are incorporated herein by reference.

SEQUENCE LISTING

This application contains a Sequence Listing that has been submitted electronically as an XML file named "44835-0125US1 SL ST26.xml". The XML file, created on Jun. 26, 2023, is 66,912 bytes in size. The material in the XML file is hereby incorporated by reference in its entirety.

TECHNICAL FIELD

This disclosure relates to genetically modified animal expressing human or chimeric (e.g., humanized) TFR1, and methods of use thereof.

BACKGROUND

Transferrin Receptor 1 (TFR1), also known as cluster of differentiation 71 (CD71), is widely expressed and can bind to transferrin (Tf) with high affinity. TfR1 expressed on the endothelial cells of the blood-brain barrier is used in pre-clinical research to allow the delivery of large molecules including antibodies into the brain. Thus, antibodies targeting TFR1 can be important for therapies of central nervous system. For example, it can be used to transport large molecules through blood-brain barrier and deliver therapies to the central nervous system.

The traditional drug research and development for various therapies involve animal models. However, because of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human TFR1 or chimeric TFR1. The animal model can express human TFR1 or chimeric TFR1 (e.g., humanized TFR1) protein in its body. It can be used in the studies on the function of TFR1 gene, and can be used in the screening and evaluation of anti-human TFR1 antibodies. In addition, the animal models prepared by the methods described herein can be used in drug screening, pharmacodynamics studies, treatments for immune-related diseases, and cancer therapy for human TFR1 target sites; they can also be used to facilitate the development and design of new drugs, and save time and cost. In summary, this disclosure provides a powerful tool for studying the function of TFR1 protein and a platform for screening cancer drugs.

In one aspect, the disclosure is related to a genetically-modified, non-human animal whose genome comprises at least one chromosome comprising a sequence encoding a human or chimeric TFR1 (Transferrin Receptor Protein 1). In some embodiments, the sequence encoding the human or chimeric TFR1 is operably linked to an endogenous regulatory element at the endogenous TFR1 gene locus in the at least one chromosome. In some embodiments, the sequence encoding a human or chimeric TFR1 comprises a sequence encoding an amino acid sequence that is at least 70%, 75%, 80%, 85%, 90%, 95%, 99%, or 100% identical to human TFR1 (NP_003225.2 (SEQ ID NO: 2)). In some embodiments, the sequence encoding a human or chimeric TFR1 comprises a sequence encoding an amino acid sequence that is at least 70%, 75%, 80%, 85%, 90%, 95%, 99%, or 100% identical to SEQ ID NO: 9. In some embodiments, the sequence encoding a human or chimeric TFR1 comprises a sequence encoding an amino acid sequence that is at least 70%, 75%, 80%, 85%, 90%, 95%, 99%, or 100% identical to amino acids 89-760 of SEQ ID NO: 2. In some embodiments, the animal is a mammal, e.g., a monkey, a rodent, a mouse, or a rat. In some embodiments, the animal is a mouse. In some embodiments, the animal does not express endogenous TFR1 or expresses a decreased level of endogenous TFR1. In some embodiments, the animal has one or more cells expressing human or chimeric TFR1. In some embodiments, the animal has one or more cells expressing human or chimeric TFR1, and the expressed human or chimeric TFR1 can interact with human transferrin (Tf) and iron, forming an iron-Tf-TFR1 complex to facilitate iron import. In some embodiments, the animal has one or more cells expressing human or chimeric TFR1, and the expressed human or chimeric TFR1 can interact with endogenous transferrin (Tf) and iron, forming an iron-Tf-TFR1 complex to facilitate iron import.

In one aspect, the disclosure is related to a genetically-modified, non-human animal, in some embodiments, the genome of the animal comprises a replacement of a sequence encoding a region of endogenous TFR1 with a sequence encoding a corresponding region of human TFR1 at an endogenous TFR1 gene locus. In some embodiments, the sequence encoding the corresponding region of human TFR1 is operably linked to an endogenous regulatory element at the endogenous TFR1 locus, and one or more cells of the animal expresses a human or chimeric TFR1. In some embodiments, the animal does not express endogenous TFR1 or expresses a decreased level of endogenous TFR1. In some embodiments, the replaced locus is the extracellular region of TFR1. In some embodiments, the animal has one or more cells expressing a chimeric TFR1 having a cytoplasmic region, a transmembrane region, and an extracellular region, in some embodiments, the extracellular region comprises a sequence that is at least 50%, 60%, 70%, 80%, 90%, 95%, or 99% identical to the extracellular region of human TFR1. In some embodiments, the extracellular region of the chimeric TFR1 has a sequence that has at least 100, 200, 300, 400, 500, 600, 620, 650, 660, 665, 666, 667, 668, 669, 670, 671, or 672 contiguous amino acids that are identical to a contiguous sequence present in the extracellular region of human TFR1. In some embodiments, the sequence encoding a region of endogenous TFR1 comprises exon 4, exon 5, exon 6, exon 7, exon 8, exon 9, exon 10, exon 11, exon 12, exon 13, exon 14, exon 15, exon 16, exon 17, exon 18, and/or exon 19, or a part thereof, of the endogenous TFR1 gene. In some embodiments, the animal is a mouse. In some embodiments, the animal is heterozygous with respect to the replacement at the endogenous TFR1 gene locus. In some embodiments, the animal is homozygous with respect to the replacement at the endogenous TFR1 gene locus.

In one aspect, the disclosure is related to a method for making a genetically-modified, non-human animal, comprising: replacing in at least one cell of the animal, at an endogenous TFR1 gene locus, a sequence encoding a region of endogenous TFR1 with a sequence encoding a corresponding region of human TFR1. In some embodiments, the sequence encoding the corresponding region of human TFR1 comprises exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19, or a part thereof, of a human TFR1 gene. In some embodiments, the sequence encoding the corresponding region of human TFR1 comprises a portion of exon 4, exon 5, exon 6, exon 7, exon 8, exon 9, exon 10, exon 11, exon 12, exon 13, exon 14, exon 15, exon 16, exon 17, exon 18, and a portion of exon 19, of a human TFR1 gene. In some embodiments, the sequence encoding the corresponding region of human TFR1 encodes amino acids 89-760 of SEQ ID NO: 2. In some embodiments, the region is located within the extracellular region of TFR1. In some embodiments, the sequence encoding a region of endogenous TFR1 comprises exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19, or a part thereof, of the endogenous TFR1 gene. In some embodiments, the animal is a mouse, and the sequence encoding a region of endogenous TFR1 comprises a portion of exon 4, exon 5, exon 6, exon 7, exon 8, exon 9, exon 10, exon 11, exon 12, exon 13, exon 14, exon 15, exon 16, exon 17, exon 18, and a portion of exon 19, of the endogenous TFR1 gene.

In one aspect, the disclosure is related to a non-human animal comprising at least one cell comprising a nucleotide sequence encoding a chimeric TFR1 polypeptide, in some embodiments, the chimeric TFR1 polypeptide comprises at least 50 contiguous amino acid residues that are identical to the corresponding contiguous amino acid sequence of a human TFR1, in some embodiments, the animal expresses the chimeric TFR1 polypeptide. In some embodiments, the chimeric TFR1 polypeptide has at least 50, at least 100, at least 150, at least 200, at least 250, at least 300, at least 350, at least 400, at least 500, at least 550, at least 600, at least 650, at least 660, at least 670, at least 671, or at least 672 contiguous amino acid residues that are identical to the corresponding contiguous amino acid sequence of a human TFR1 extracellular region. In some embodiments, the chimeric TFR1 polypeptide comprises a sequence that is at least 90%, 95%, or 99% identical to amino acids 89-760 of SEQ ID NO: 2. In some embodiments, the nucleotide sequence is operably linked to an endogenous TFR1 regulatory element of the animal. In some embodiments, the chimeric TFR1 polypeptide comprises an endogenous TFR1 cytoplasmic region and/or an endogenous TFR1 transmembrane region. In some embodiments, the nucleotide sequence is integrated to an endogenous TFR1 gene locus of the animal. In some embodiments, the chimeric TFR1 polypeptide has at least one mouse TFR1 activity and/or at least one human TFR1 activity.

In one aspect, the disclosure is related to a method of making a genetically-modified animal cell that expresses a chimeric TFR1, the method comprising: replacing at an endogenous TFR1 gene locus, a nucleotide sequence encoding a region of endogenous TFR1 with a nucleotide sequence encoding a corresponding region of human TFR1, thereby generating a genetically-modified animal cell that includes a nucleotide sequence that encodes the chimeric TFR1, in some embodiments, the animal cell expresses the chimeric TFR1. In some embodiments, the animal is a mouse. In some embodiments, the chimeric TFR1 comprises a cytoplasmic region and/or a transmembrane region of mouse TFR1; and an extracellular region of human TFR1. In some embodiments, the nucleotide sequence encoding the chimeric TFR1 is operably linked to an endogenous TFR1 regulatory region, e.g., promoter.

In some embodiments, the animal further comprises a sequence encoding an additional human or chimeric protein. In some embodiments, the additional human or chimeric protein is programmed cell death protein 1 (PD)-1), programmed cell death ligand 1 (PD-L1), cytotoxic T-lymphocyte-associated protein 4 (CTLA-4), TNF receptor superfamily member 4 (OX40), lymphocyte-activation gene 3 (LAG3), T-cell immunoglobulin and mucin-domain containing-3 (TIM-3), or CD73.

In one aspect, the disclosure is related to a method of determining effectiveness of an anti-TFR1 antibody for the treatment of cancer (e.g., tumor), comprising: a) administering the anti-TFR1 antibody to the animal as described herein, in some embodiments, the animal has a cancer (e.g., tumor); and determining inhibitory effects of the anti-TFR1 antibody to the cancer (e.g., tumor). In some embodiments, the cancer (e.g., tumor) comprises one or more cells that express TFR1. In some embodiments, the cancer (e.g., tumor) comprises one or more cancer cells that are injected into the animal. In some embodiments, determining inhibitory effects of the anti-TFR1 antibody to the cancer involves measuring the tumor volume in the animal. In some embodiments, the cancer is brain cancer, breast cancer, colon cancer, liver cancer, ovarian cancer, lung cancer, bone cancer, leukemia, and/or lymphoma.

In one aspect, the disclosure is related to a method of determining effectiveness of an anti-TFR1 antibody and an additional therapeutic agent for the treatment of cancer, comprising a) administering the anti-TFR1 antibody and the additional therapeutic agent to the animal as described herein, in some embodiments, the animal has a cancer (e.g., tumor); and b) determining inhibitory effects on the cancer (e.g., tumor). In some embodiments, the animal further comprises a sequence encoding a human or chimeric programmed cell death protein 1 (PD)-1). In some embodiments, the animal further comprises a sequence encoding a human or chimeric programmed death-ligand 1 (PD-L1). In some embodiments, the additional therapeutic agent is an anti-PD-1 antibody or an anti-PD-L1 antibody. In some embodiments, the cancer comprises one or more cancer cells that express TFR1 and/or PD-L1. In some embodiments, the cancer is caused by injection of one or more cancer cells into the animal. In some embodiments, determining inhibitory effects of the treatment involves measuring the tumor volume in the animal. In some embodiments, the animal has brain cancer, breast cancer, colon cancer, liver cancer, ovarian cancer, lung cancer, bone cancer, leukemia, and/or lymphoma.

In one aspect, the disclosure is related to a method of determining delivery efficiency of a therapeutic agent to cross the blood-brain barrier, comprising: a) administering the therapeutic agent to the animal as described herein; and b) determining concentration of the therapeutic agent over time in brain and/or serum of the animal. In some embodiments, the therapeutic agent comprises an anti-TFR1 antibody or antigen-binding fragment thereof. In some embodiments, the therapeutic agent is a multi-specific antibody (e.g., a bispecific antibody) targeting TFR1 (e.g., human TFR1) and a second antigen. In some embodiments, the second antigen is beta-secretase 1 (BACE1) or amyloid beta. In some embodiments, concentration of the therapeutic agent is determined over a period of at least 5 hours, at least 10 hours, at least 15 hours, at least 20 hours, or at least 25 hours.

In one aspect, the disclosure is related to a method of determining effectiveness of an anti-TFR1 antibody for treating a bone disease, comprising: a) administering the anti-TFR1 antibody to the animal as described herein, in some embodiments, the animal has the bone disease; and b)determining effects of the anti-TFR1 antibody for treating the bone disease. In some embodiments, the bone disease is fractures, bone degeneration, arthritis, bone deformities, osteoporosis, and/or necrosis of the femoral head.

In one aspect, the disclosure is related to a method of determining effectiveness of an anti-TFR1 antibody for treating a neurodegenerative disease, comprising: a) administering the anti-TFR1 antibody to the animal as described herein, in some embodiments, the animal has the neurodegenerative disease; and b) determining effects of the anti-TFR1 antibody for treating the neurodegenerative disease. In some embodiments, the neurodegenerative disease is cerebral ischemia, brain injury or, epilepsy, Alzheimer's disease. Parkinson's disease, amyotrophic lateral sclerosis and/or spinocerebellar ataxia.

In one aspect, the disclosure is related to a method of determining effectiveness of an anti-TFR1 antibody for treating an immune disorder, comprising: a) administering the anti-TFR1 antibody to the animal as described herein, in some embodiments, the animal has the immune disorder; and b) determining effects of the anti-TFR1 antibody for treating the immune disorder. In some embodiments, the immune disorder is allergy, asthma, myocarditis, nephritis, hepatitis, systemic lupus erythematosus, rheumatoid arthritis, scleroderma, hyperthyroidism, idiopathic thrombocytopenia purpura, autoimmune hemolytic anemia, ulcerative colitis, autologous Immune liver disease, diabetes, pain and/or neurological disorders.

In one aspect, the disclosure is related to a protein comprising an amino acid sequence, in some embodiments, the amino acid sequence is one of the following: (a) an amino acid sequence set forth in SEQ ID NO: 1, 2, or 9; (b) an amino acid sequence that is at least 90% identical to SEQ ID NO: 1, 2, or 9; (c) an amino acid sequence that is at least 91%, 92%, 93%, 94%, 95%, 96%, 97%, 98%, or 99% identical to SEQ ID NO: 1, 2, or 9; (d) an amino acid sequence that is different from the amino acid sequence set forth in SEQ ID NO: 1, 2, or 9 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 1, 2, or 9.

In one aspect, the disclosure is related to a nucleic acid comprising a nucleotide sequence, in some embodiments, the nucleotide sequence is one of the following: (a) a sequence that encodes the protein as described herein; (b) SEQ ID NO: 3, 4, 5, 6, 7, or 8; (c) a sequence that is at least 90% identical to SEQ ID NO: 3, 4, 5, 6, 7, or 8; and (d) a sequence that is at least 91%, 92%, 93%, 94%, 95%, 96%, 97%, 98%, or 99% identical to SEQ ID NO: 3, 4, 5, 6, 7, or 8.

In one aspect, the disclosure is related to a cell comprising the protein and/or the nucleic acid as described herein.

In one aspect, the disclosure is related to an animal comprising the protein and/or the nucleic acid as described herein.

In another aspect, the disclosure also provides a genetically-modified, non-human animal whose genome comprise a disruption in the animal's endogenous TFR1 gene, wherein the disruption of the endogenous TFR1 gene comprises deletion of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19, or part thereof of the endogenous TFR1 gene.

In some embodiments, the disruption of the endogenous TFR1 gene comprises deletion of one or more exons or part of exons selected from the group consisting of exon 4, exon 5, exon 6, exon 7, exon 8, exon 9, exon 10, exon 11, exon 12, exon 13, exon 14, exon 15, exon 16, exon 17, exon 18, and/or exon 19 of the endogenous TFR1 gene.

In some embodiments, the disruption of the endogenous TFR1 gene further comprises deletion of one or more introns or part of introns selected from the group consisting of intron 4, intron 5, intron 6, intron 7, intron 8, intron 9, intron 10, intron 11, intron 12, intron 13, intron 14, intron 15, intron 16, intron 17, and/or intron 18 of the endogenous TFR1 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, or more nucleotides.

In some embodiments, the disruption of the endogenous TFR1 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nucleotides of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19 (e.g., deletion of at least 180 nucleotides from exon 4, exons 5-18, and at least 200 nucleotides from exon 19).

The disclosure further relates to a TFR1 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the TFR1 gene function, human TFR1 antibodies, the drugs or efficacies for human TFR1 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 9 shows the alignment between human TFR1 amino acid sequence (NP_003225.2; SEQ ID NO: 2) and mouse TFR1 amino acid sequence (NP_035768.1; SEQ ID NO: 1).

FIG. 10 shows the alignment between human TFR1 amino acid sequence (NP_003225.2; SEQ ID NO: 2) and rat TFR1 amino acid sequence (NP_073203.1; SEQ ID NO: 31).

DETAILED DESCRIPTION

Figure 1:
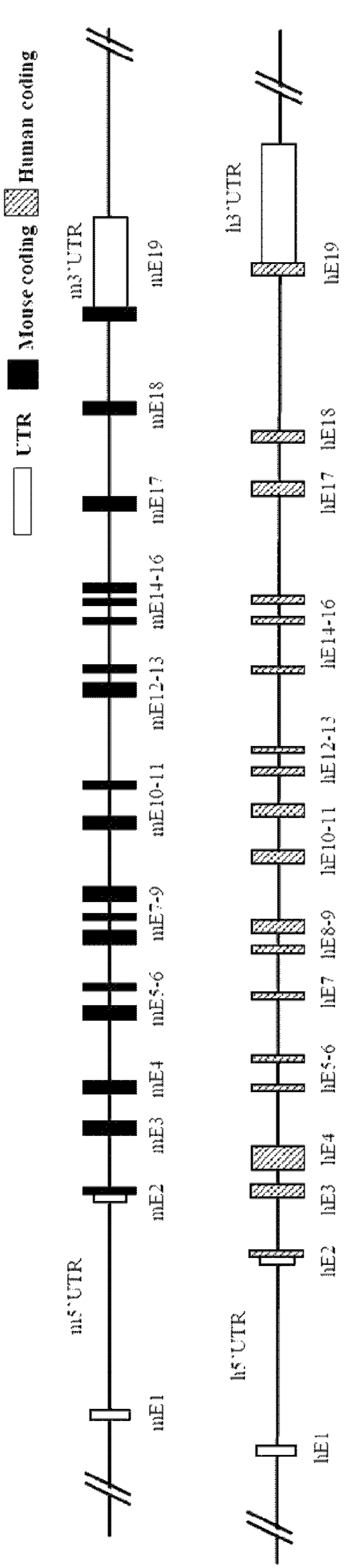
FIG. 1 is a schematic diagram showing mouse and human TFR1 gene loci.

This disclosure relates to transgenic non-human animal with human or chimeric (e.g., humanized) TFR1, and methods of use thereof.

Iron is a vital element in several biological processes including oxygen transportation, energy generation/mitochondrial function, as well as DNA synthesis and repair. Within the context of a cancer cell, facilitating DNA synthesis would allow increased proliferation, while increased capacity to repair DNA would aid in repairing DNA damage from the increased mutational burden common among cancer cells. Central proteins in the regulation of iron metabolism are transferrin (Tf) and its receptors. As the main cellular importer of iron, transferrin receptor 1 (TFR1) function is essential to iron related processes and the uptake of Tf-bound iron through TFR1 is the main source of cellular iron import in general.

As disruption of iron homeostasis may have potentially detrimental consequences to the cell, the expression of TFR1 is tightly regulated. However, TFR1 is overexpressed on many different types of cancer cells, often at levels several-fold higher than normal cells. In fact, TFR1 has been identified as a universal cancer marker. Increased expression of TFR1 correlates with advanced stage and/or poorer prognosis in a number of cancers, e.g., solid cancers such as esophageal squamous cell carcinoma, breast cancer, ovarian cancer, lung cancer, cervical cancer, bladder cancer, osteosarcoma, pancreatic cancers, cholangiocarcinoma, renal cell carcinoma, hepatocellular carcinoma, adrenal cortical carcinoma, and cancers of the nervous system as well as hematopoietic malignancies such as acute lymphoblastic leukemia (ALL), chronic lymphocytic leukemia (CLL), and non-Hodgkin lymphoma (NHL). Therefore, TFR1 is regarded as a potential biomarker and therapeutic target for cancer.

Furthermore, TfR1 expressed on the endothelial cells of the blood-brain barrier can be used to allow the delivery of large molecules including antibodies into the brain. Some of the TfR1 targeting antibodies have been shown to cross the blood-brain barrier, without interfering with the uptake of iron. The affinity of the antibody-TfR interaction seems to be important determining the success of transcytotic transport over endothelial cells of the blood-brain barrier.

Experimental animal models are an indispensable research tool for studying the effects of these antibodies (e.g., anti-TFR1 antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

TFR1

Transferrin Receptor 1 (TFR1), also known as cluster of differentiation 71 (CD71), is widely expressed and can bind to transferrin (Tf) with high affinity. Human TFR1 is a 90 kDa type II transmembrane glycoprotein consisting of 760 amino acids that is found as a dimer (180 kDa) linked by disulfide bonds on the cell surface. The TFR1 monomer is composed of a large extracellular, C-terminal domain of 671 amino acids containing the Tf-binding site, a transmembrane domain (28 amino acids), and an intracellular N-terminal domain (61 amino acids). The C-terminal extracellular domain contains three N-linked glycosylation sites at asparagine residues 251, 317, and 727 and one O-linked glycosylation site at threonine 104, which are all required for adequate function of the receptor.

Transferrin (Tf) It is an 80 kDa glycoprotein composed of two 40 kDa subunits, known as the N- and C-lobes that are separated by a short linker sequence. Each subunit is capable of binding to one free ferric iron ($Fe^{3+}$) and thus, Tf may have up to two atoms of iron attached. Tf in its iron free form, apo-Tf, binds $Fe^{3+}$ with high efficiency in the blood and transports it to the cell surface for internalization through the interaction with TFR1. As a membrane protein regulating iron import, TFR1 is a member of the TFR family that shows nanomolar affinity to transferrin (Tf) bound to $Fe^{3+}$. The complex of Tf-TFR1 is internalized through endocytosis mediated by clathrin, and $Fe^{3+}$ is disassociated from Tf when pH decreases to 5.5. At this pH, apo-Tf and TFR1 are still associated and recycled to cell surface with physiological pH, so the former is released.

Iron uptake by transferrin receptor is an important way for cancer cells to absorb iron, thus accumulating evidence has proven that TFR1 participated in tumor onset and progression, and its expression was dysregulated significantly in many cancers. The relationship between TFR1 and cancers has been revealed, rendering TFR1 a valuable pharmaceutical target for intervening with cancers.

TFR1 expressed on the endothelial cells of the blood-brain barrier is used also in preclinical research to allow the delivery of large molecules including antibodies into the brain. Some of the TFR1 targeting antibodies have been shown to cross the blood-brain barrier, without interfering with the uptake of iron.

A detailed description of TFR1, Tf, and their functions can be found, e.g., in Candelaria, P. V., et al. "Antibodies targeting the transferrin receptor 1 (TfR1) as direct anti-cancer agents." Frontiers in Immunology 12 (2021): 607692; and Shen, Y., et al. "Transferrin receptor 1 in cancer: a new sight for cancer therapy." American Journal of Cancer Research 8.6 (2018): 916; each of which is incorporated by reference in its entirety.

In human genomes, TFR1 gene (Gene ID: 7037) locus has nineteen exons, exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and exon 19 (FIG. 1). The TFR1 protein also has, from N-terminus to C-terminus, a cytoplasmic region, a transmembrane region, and an extracellular region. The nucleotide sequence for human TFR1 mRNA is NM_003234.4, and the amino acid sequence for human TFR1 is NP_003225.2 (SEQ ID NO: 2).

The location for each exon and each region in human TFR1 nucleotide sequence and amino acid sequence is listed below:

TABLE 1

| Human TFR1 (approximate location) | NM_003234.4 5224 bp | NP_003225.2 760 aa (SEQ ID NO: 2) |
|---|---|---|
| Exon 1 | 1-260 | 0 |
| Exon 2 | 261-319 | 1-12 |
| Exon 3 | 320-521 | 13-79 |
| Exon 4 | 522-717 | 80-145 |
| Exon 5 | 718-867 | 146-195 |
| Exon 6 | 868-970 | 196-229 |
| Exon 7 | 971-1084 | 230-267 |
| Exon 8 | 1085-1183 | 268-300 |
| Exon 9 | 1184-1323 | 301-347 |
| Exon 10 | 1324-1481 | 348-399 |
| Exon 11 | 1482-1601 | 400-439 |
| Exon 12 | 1602-1687 | 440-468 |
| Exon 13 | 1688-1751 | 469-489 |
| Exon 14 | 1752-1819 | 490-512 |
| Exon 15 | 1820-1878 | 513-532 |
| Exon 16 | 1879-1960 | 533-559 |
| Exon 17 | 1961-2182 | 560-633 |
| Exon 18 | 2183-2323 | 634-647 |
| Exon 19 | 2324-5224 | 648-760 |
| Cytoplasmic | 284-484 | 1-67 |
| Transmembrane | 485-547 | 68-88 |
| Extracellular | 548-2563 | 89-760 |
| Donor region | 548-2566 | 89-760 |

The human TFR1 gene (Gene ID: 7037) is located in Chromosome 16 of the human genome, which is located from 196018694 to 1960821231 of NC_000003.12. The 5' UTR is from 196082043 to 196082090, and from 196077100 to 196077122; Exon 1 is from 196082090 to 196082043; the first intron is from 196082042 to 196077123; Exon 2 is from 196077122 to 196077064; the second intron is from 196077063 to 196075361; Exon 3 is from 196075360 to 196075159; the third intron is from 196075158 to 196074126; Exon 4 is from 196074125 to 196073930; the fourth intron is from 196073929 to 196072153; Exon 5 is from 196072152 to 196072003; the fifth intron is from 196072002 to 196071499; Exon 6 is from 196071498 to 196071396; the sixth intron is from 196071395 to 196069569; Exon 7 is from 196069568 to 196069455; the seventh intron is from 196069454 to 196068131; Exon 8 is from 196068130 to 196068032; the eighth intron is from 196068031 to 196067658; Exon 9 is from 196067657 to 196067518; the ninth intron is from 196067517 to 196065601; Exon 10 is from 196065600 to 196065443; the tenth intron is from 196065442 to 196064429; Exon 11 is from 196064428 to 196064309; the eleventh intron is from 196064308 to 196062940; Exon 12 is from 196062939 to 196062854; the twelfth intron is from 196062853 to 196062646; Exon 13 is from 196062645 to 196062582; the thirteen intron is from 196062581 to 196060248; Exon 14 is from 196060247 to 196060180; the fourteenth intron is from 196060179 to 196058633; Exon 15 is from 196058632 to 196058574; the fifteenth intron is from 196058573 to 196058366; Exon 16 is from 196058365 to 196058284; the sixteenth intron is from 196058283 to 196055302; Exon 17 is from 196055301 to 196055080; the seventeenth intron is from 196055079 to 196053559; Exon 18 is from 196053558 to 196053418; the eighteenth intron is from 196053417 to 196052185; Exon 19 is from 196052184 to 196049284, and the 3'UTR is from 196049284 to 196051941, based on transcript NM_003234.4. All relevant information for mouse TFR1 locus can be found in the NCBI website with Gene ID: 7037.

In mice, TFR1 gene locus has nineteen exons, exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and exon 19 (FIG. 1). The mouse TFR1 protein also has, from N-terminus to C-terminus, a cytoplasmic region, a transmembrane region, and an extracellular region. The nucleotide sequence for mouse TFR1 mRNA is NM_011638.4, the amino acid sequence for mouse TFR1 is NP_035768.1 (SEQ ID NO: 1). The location for each exon and each region in the mouse TFR1 nucleotide sequence and amino acid sequence is listed below:

TABLE 2

| Mouse TFR1 (approximate location) | NM_011638.4 4920 bp | NP_035768.1 763 aa (SEQ ID NO: 1) |
|---|---|---|
| Exon 1 | 1-141 | 0 |
| Exon 2 | 142-200 | 1-12 |
| Exon 3 | 201-402 | 13-79 |
| Exon 4 | 403-604 | 80-147 |
| Exon 5 | 605-754 | 148-197 |
| Exon 6 | 755-857 | 198-231 |
| Exon 7 | 868-971 | 232-269 |
| Exon 8 | 972-1070 | 270-302 |
| Exon 9 | 1071-1210 | 303-349 |
| Exon 10 | 1211-1368 | 350-401 |
| Exon 11 | 1369-1491 | 402-442 |
| Exon 12 | 1492-1577 | 443-471 |
| Exon 13 | 1578-1641 | 472-492 |
| Exon 14 | 1642-1709 | 493-515 |
| Exon 15 | 1710-1768 | 516-535 |
| Exon 16 | 1769-1850 | 536-562 |
| Exon 17 | 1851-2072 | 563-636 |
| Exon 18 | 2073-2213 | 637-683 |
| Exon 19 | 2214-4914 | 684-763 |
| Cytoplasmic | 142-359 | 1-65 |
| Transmembrane | 360-428 | 66-88 |
| Extracellular | 429-2453 | 89-763 |
| Replaced region | 429-2456 | 89-763 |

The mouse TFR1 gene (Gene ID: 22042) is located in Chromosome 16 of the mouse genome, which is located from 32427714 to 32451612 of NC_000082.7. The 5' UTR is from 32427738 to 32427854; and from 32431986 to 32432008; Exon 1 is from 32427738 to 32427854; the first intron is from 32427855 to 32431985; Exon 2 is from 32431986 to 32432044; the second intron is from 32432045 to 32433383; Exon 3 is from 32433384 to 32433585; the third intron is from 32433586 to 32434010; Exon 4 is from 32434011 to 32434212; the fourth intron is from 32434213 to 32435566; Exon 5 is from 32435567 to 32435716; the fifth intron is from 32435717 to 32435914; Exon 6 is from 32435915 to 32436017; the sixth intron is from 32436018 to 32437035; Exon 7 is from 32437036 to 32437149; the seventh intron is from 32437150 to 32437450; Exon 8 is from 32437451 to 32437549; the eighth intron is from 32437550 to 32437854; Exon 9 is from 32437855 to 32437994; the ninth intron is from 32437995 to 32439183; Exon 10 is from 32439184 to 32439341; the tenth intron is from 32439342 to 32439992; Exon 11 is from 32439993 to 32440115; the eleventh intron is from 32440116 to 32441874; Exon 12 is from 32441875 to 32441960; the twelfth intron is from 32441961 to 32442189; Exon 13 is from 32442190 to 32442253; the thirteen intron is from 32442254 to 32443186; Exon 14 is from 32443187 to 32443254; the fourteenth intron is from 32443255 to 32443585; Exon 15 is from 32443586 to 32443644; the fifteenth intron is from 32443645 to 32443801; Exon 16 is from 32443802 to 32443883; the sixteenth intron is from 32443884 to 32445366; Exon 17 is from 32445367 to 32445588; the seventeenth intron is from 32445589 to 32447293; Exon 18 is from 32447294 to 32447434; the eighteenth intron is from 32447435 to 32448911; Exon 19 is from 32448912 to 32451612; and the 3'UTR is from 32449155 to 32451612; based on transcript NM_011638.4. All relevant information for mouse TFR1 locus can be found in the NCBI website with Gene ID: 22042, which is incorporated by reference herein in its entirety.

FIG. 9 shows the alignment between human TFR1 amino acid sequence (NP_003225.2; SEQ ID NO: 2) and mouse TFR1 amino acid sequence (NP_035768.1; SEQ ID NO: 1). Thus, the corresponding amino acid residue or region between human and mouse TFR1 can be found in FIG. 9.

TFR1 genes, proteins, and locus of the other species are also known in the art. For example, the gene ID for TFR1 in *Rattus norvegicus* (rat) is 64678, the gene ID for TFR1 in *Felis catus* (cat) is 493880, the gene ID for TFR1 in *Canis lupus familiaris* (dog) is 403703, and the gene ID for TFR1 in *Sus scrofa* (pig) is 397062. The relevant information for these genes (e.g., intron sequences, exon sequences, amino acid residues of these proteins) can be found, e.g., in NCBI database, which is incorporated by reference herein in its entirety. FIG. 10 shows the alignment between human TFR1 amino acid sequence (NP_003225.2; SEQ ID NO: 2) and rat TFR1 amino acid sequence (NP_073203.1; SEQ ID NO: 31). Thus, the corresponding amino acid residue or region between human and rodent TFR1 can be found in FIG. 10.

The present disclosure provides human or chimeric (e.g., humanized) TFR1 nucleotide sequence and/or amino acid sequences. In some embodiments, the entire sequence of mouse exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, cytoplasmic region, transmembrane region, and/or extracellular region are replaced by the corresponding human sequence. In some embodiments, a "region" or "portion" of mouse exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, cytoplasmic region, transmembrane region, and/or extracellular region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, or 2000 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 660, or 670 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, cytoplasmic region, transmembrane region, or extracellular region. In some embodiments, a region, a portion, or the entire sequence of mouse exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19 (e.g., a portion of exon 4, exons 5-18, and a portion of exon 19) are replaced by a region, a portion, or the entire sequence of the human exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19 (e.g., a portion of exon 4, exons 5-18, and a portion of exon 19).

In some embodiments, a "region" or "portion" of the cytoplasmic region, transmembrane region, extracellular region, exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19 is deleted.

In some embodiments, the present disclosure is related to a genetically-modified, non-human animal whose genome comprises a chimeric (e.g., humanized) TFR1 nucleotide sequence. In some embodiments, the chimeric (e.g., humanized) TFR1 nucleotide sequence encodes a TFR1 protein comprising an extracellular region. In some embodiments, the extracellular region described herein is at least 80%, 85%, 90%, 95%, or 100% identical to amino acids 89-760 of SEQ ID NO: 2. In some embodiments, the extracellular region comprises the entire or part of human TFR1 extracellular region. In some embodiments, the genome of the animal comprises a sequence that is at least 80%, 85%, 90%, 95%, or 100% identical to SEQ ID NO: 3, 4, 5, 6, 7, 8, or 10.

In some embodiments, the genetically-modified non-human animal described herein comprises a sequence encoding a human or humanized TFR1 protein. In some embodiments, the TFR1 protein comprises, from N-terminus to C-terminus, a cytoplasmic region, a transmembrane region, and an extracellular region. In some embodiments, the humanized TFR1 protein comprises a human or humanized cytoplasmic region. In some embodiments, the humanized TFR1 protein comprises an endogenous cytoplasmic region. In some embodiments, the humanized TFR1 protein comprises a human or humanized transmembrane region. In some embodiments, the humanized TFR1 protein comprises an endogenous transmembrane region. In some embodiments, the humanized TFR1 protein comprises a human or humanized extracellular region. In some embodiments, the humanized TFR1 protein comprises an endogenous extracellular region.

In some embodiments, the genetically-modified non-human animal described herein comprises a human or humanized TFR1 gene. In some embodiments, the humanized TFR1 gene comprises 19 exons. In some embodiments, the humanized TFR1 gene comprises endogenous or humanized exon 1, endogenous or humanized exon 2, endogenous or humanized exon 3, human or humanized exon 4, human or humanized exon 5, human or humanized exon 6, human or humanized exon 7, human or humanized exon 8, human or humanized exon 9, human or humanized exon 10, human or humanized exon 11, human or humanized exon 12, human or humanized exon 13, human or humanized exon 14, human or humanized exon 15, human or humanized exon 16, human or humanized exon 17, human or humanized exon 18, and/or human or humanized exon 19. In some embodiments, the humanized TFR1 gene comprises endogenous or humanized intron 1, endogenous or humanized intron 2, human or humanized intron 3, human or humanized intron 4, human or humanized intron 5, human or humanized intron 6, human or humanized intron 7, human or humanized intron 8, human or humanized intron 9, human or humanized intron 10, human or humanized intron 11, human or humanized intron 12, human or humanized intron 13, human or humanized intron 14, human or humanized intron 15, human or humanized intron 16, human or humanized intron 17, and/or human or humanized intron 18. In some embodiments, the humanized TFR1 gene comprises human or humanized 5' UTR. In some embodiments, the humanized TFR1 gene comprises human or humanized 3' UTR. In some embodiments, the humanized TFR1 gene comprises endogenous 5' UTR. In some embodiments, the humanized TFR1 gene comprises endogenous 3' UTR.

Thus, in some embodiments, the present disclosure also provides a chimeric (e.g., humanized) TFR1 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse TFR1 mRNA sequence (e.g., NM_011638.4), mouse TFR1 amino acid sequence (e.g., SEQ ID NO: 1), or a portion thereof (e.g., exon 1, exon 2, exon 3, a portion of exon 4, and a portion of exon 19); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human TFR1 mRNA sequence (e.g., NM_003234.4), human TFR1 amino acid sequence (e.g., SEQ ID NO: 2), or a portion thereof (e.g., a portion of exon 4, exons 5-18, and a portion of exon 19).

In some embodiments, the sequence encoding amino acids 89-763 of mouse TFR1 (SEQ ID NO: 1) is replaced. In some embodiments, the sequence is replaced by a sequence encoding a corresponding region of human TFR1 (e.g., amino acids 89-760 of human TFR1 (SEQ ID NO: 2)).

In some embodiments, the nucleic acids as described herein are operably linked to a promotor or regulatory element, e.g., an endogenous mouse TFR1 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from part of or the entire mouse TFR1 nucleotide sequence (e.g., a portion of exon 4, exons 5-18, and a portion of exon 19 of NM_011638.4).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as part of or the entire mouse TFR1 nucleotide sequence (e.g., exons 1-3, a portion of exon 4, and a portion of exon 19 of NM_011638.4).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from part of or the entire human TFR1 nucleotide sequence (e.g., exon 1, exon 2, exon 3, a portion of exon 4, and a portion of exon 19 of NM_003234.4).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as part of or the entire human TFR1 nucleotide sequence (e.g., a portion of exon 4, exons 5-18, and portion of exon 19 of NM_003234.4).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from part of or the entire mouse TFR1 amino acid sequence (e.g., amino acids 89-763 of NP_035768.1 (SEQ ID NO: 1)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as part of or the entire mouse TFR1 amino acid sequence (e.g., amino acids 1-88 of NP_035768.1 (SEQ ID NO: 1)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from part of or the entire human TFR1 amino acid sequence (e.g., amino acids 1-88 of NP_003225.2 (SEQ ID NO: 2)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as part of or the entire human TFR1 amino acid sequence (e.g., amino acids 89-760 of NP_003225.2 (SEQ ID NO: 2)).

The present disclosure also provides a humanized TFR1 mouse amino acid sequence, wherein the amino acid sequence is selected from the group consisting of:

a) an amino acid sequence shown in SEQ ID NO: 1, 2, or 9;
b) an amino acid sequence having a homology of at least 90% with or at least 90% identical to the amino acid sequence shown in SEQ ID NO: 1, 2, or 9;
c) an amino acid sequence encoded by a nucleic acid sequence, wherein the nucleic acid sequence is able to hybridize to a nucleotide sequence encoding the amino acid shown in SEQ ID NO: 1, 2, or 9 under a low stringency condition or a strict stringency condition;
d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 1, 2, or 9;
e) an amino acid sequence that is different from the amino acid sequence shown in SEQ ID NO: 1, 2, or 9 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 1, 2, or 9.

The present disclosure also provides a humanized TFR1 amino acid sequence, wherein the amino acid sequence is selected from the group consisting of:

a) all or part of amino acids 89-760 of SEQ ID NO: 2;
b) an amino acid sequence have a homology of at least 90%, 91%, 92%, 93%, 94%, 95%, 96%, 97%, 98%, or 99% to amino acids 89-760 of SEQ ID NO: 2;
c) an amino acid sequence that is different from amino acids 89-760 of SEQ ID NO: 2 by no more than 10, 9, 8, 7, 6, 5, 4, 3, 2 or no more than 1 amino acid; and
d) an amino acid sequence that comprises a substitution, a deletion and/or insertion of one or more amino acids to amino acids 89-760 of SEQ ID NO: 2.

The present disclosure also provides a humanized TFR1 amino acid sequence, wherein the amino acid sequence is selected from the group consisting of:

a) all or part of amino acids 1-88 of SEQ ID NO: 1;
b) an amino acid sequence have a homology of at least 90%, 91%, 92%, 93%, 94%, 95%, 96%, 97%, 98%, or 99% to amino acids 1-88 of SEQ ID NO: 1;
c) an amino acid sequence that is different from amino acids 1-88 of SEQ ID NO: 1 by no more than 10, 9, 8, 7, 6, 5, 4, 3, 2 or no more than 1 amino acid; and
d) an amino acid sequence that comprises a substitution, a deletion and/or insertion of one or more amino acids to amino acids 1-88 of SEQ ID NO: 1.

The present disclosure also relates to a TFR1 nucleic acid (e.g., DNA or RNA) sequence, wherein the nucleic acid sequence can be selected from the group consisting of:

a) a nucleic acid sequence as shown in SEQ ID NO: 3, 4, 5, 6, 7, or 8, or a nucleic acid sequence encoding a homologous TFR1 amino acid sequence of a humanized mouse TFR1;
b) a nucleic acid sequence that is able to hybridize to the nucleotide sequence as shown in SEQ ID NO: 3, 4, 5, 6, 7, or 8 under a low stringency condition or a strict stringency condition;
c) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 3, 4, 5, 6, 7, or 8;
d) a nucleic acid sequence that encodes an amino acid sequence, wherein the amino acid sequence has a homology of at least 90% with or at least 90% identical to the amino acid sequence shown in SEQ ID NO: 1, 2, or 9;
e) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 1, 2, or 9;
f) a nucleic acid sequence that encodes an amino acid sequence, wherein the amino acid sequence is different from the amino acid sequence shown in SEQ ID NO: 1, 2, or 9 by no more than 10, 9, 8, 7, 6, 5, 4, 3, 2 or no more than 1 amino acid; and/or
g) a nucleic acid sequence that encodes an amino acid sequence, wherein the amino acid sequence comprises a substitution, a deletion and/or insertion of one or more amino acids to the amino acid sequence shown in SEQ ID NO: 1, 2, or 9.

The present disclosure further relates to a TFR1 genomic DNA sequence of a humanized mouse. The DNA sequence is obtained by reverse transcription of the mRNA obtained by transcription thereof is consistent with or complementary to the DNA sequence homologous to the sequence shown in SEQ ID NO: 5 or 8.

The disclosure also provides an amino acid sequence that has a homology of at least 90% with, or at least 90% identical to the sequence shown in SEQ ID NO: 1, 2, or 9, and has protein activity. In some embodiments, the homology with the sequence shown in SEQ ID NO: 1, 2, or 11 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 1, 2, or 9 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 3, 4, 5, 6, 7, or 8, and encodes a polypeptide that has protein activity. In some embodiments, the homology with the sequence shown in SEQ ID NO: 3, 4, 5, 6, 7, or 8 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 3, 4, 5, 6, 7, or 8 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For example, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) TFR1 from an endogenous non-human TFR1 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous TFR1 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wild-type nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wild-type amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

As used herein, the term "humanized protein" or "humanized polypeptide" refers to a protein or a polypeptide, wherein at least a portion of the protein or the polypeptide is from the human protein or human polypeptide. In some embodiments, the humanized protein or polypeptide is a human protein or polypeptide.

As used herein, the term "humanized nucleic acid" refers to a nucleic acid, wherein at least a portion of the nucleic acid is from the human. In some embodiments, the entire nucleic acid of the humanized nucleic acid is from human. In some embodiments, the humanized nucleic acid is a humanized exon. A humanized exon can be e.g., a human exon or a chimeric exon.

In some embodiments, the chimeric gene or the chimeric nucleic acid is a humanized TFR1 gene or a humanized TFR1 nucleic acid. In some embodiments, at least one or more portions of the gene or the nucleic acid is from the human TFR1 gene, at least one or more portions of the gene or the nucleic acid is from a non-human TFR1 gene. In some embodiments, the gene or the nucleic acid comprises a sequence that encodes an TFR1 protein. The encoded TFR1 protein is functional or has at least one activity of the human TFR1 protein or the non-human TFR1 protein, e.g., interacting with transferrin; regulating cellular uptake of iron by endocytosis; and maintaining iron homeostasis.

In some embodiments, the chimeric protein or the chimeric polypeptide is a humanized TFR1 protein or a humanized TFR1 polypeptide. In some embodiments, at least one or more portions of the amino acid sequence of the protein or the polypeptide is from a human TFR1 protein, and at least one or more portions of the amino acid sequence of the protein or the polypeptide is from a non-human TFR1 protein. The humanized TFR1 protein or the humanized TFR1 polypeptide is functional or has at least one activity of the human TFR1 protein or the non-human TFR1 protein.

In some embodiments, the cytoplasmic region is human or humanized. In some embodiments, the cytoplasmic region is endogenous. In some embodiments, the transmembrane region is human or humanized. In some embodiments, the transmembrane region is endogenous. In some embodiments, the extracellular region is human or humanized. In some embodiments, the extracellular region is endogenous.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," *Cold Spring Harbor Laboratory Press,* 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae(climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/O1a. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129). In some embodiments, the non-human animal is a rodent. In some embodiments, the non-human animal is a mouse having a BALB/c, A, A/He, A/J, A/WySN, AKR, AKR/A, AKR/J, AKR/N, TA1, TA2, RF, SWR, C3H, C57BR, SJL, C57L, DBA/2, KM, NIH, ICR, CFW, FACA, C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL (C57BL/10Cr and C57BL/O1a), C58, CBA/Br, CBA/Ca, CBA/J, CBA/st, or CBA/H background.

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized TFR1 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/$\gamma c^{null}$ mice (Ito, M. et al., NOD/SCID/$\gamma c^{null}$ mouse: an excellent recipient mouse model for engraftment of human cells, Blood 100(9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human TFR1 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/$\gamma c^{null}$ mice, nude mice, Rag1 and/or Rag2 knockout mice, NOD-Prkdc$^{scid}$ IL-2r$\gamma^{null}$ mice, NOD-Rag $1^{-/-}$-IL2rg$^{-/-}$ (NRG) mice, Rag $2^{-/-}$-IL2rg$^{-/-}$ (RG) mice, and a combination thereof. These genetically modified animals are described, e.g., in U.S.20150106961, which is incorporated herein by reference in its entirety. In some embodiments, the mouse can include a replacement of all or part of mature TFR1 coding sequence with human mature TFR1 coding sequence.

Genetically modified non-human animals that comprise a modification of an endogenous non-human TFR1 locus. In some embodiments, the modification can comprise a human nucleic acid sequence encoding at least a portion of a mature TFR1 protein (e.g., at least 10%, 20%, 30%, 40%, 50%, 60%, 70%, 80%, 90%, 95%, 96%, 97%, 98%, or 99% identical to the mature TFR1 protein sequence). Although genetically modified cells are also provided that can comprise the modifications described herein (e.g., ES cells, somatic cells), in many embodiments, the genetically modified non-human animals comprise the modification of the endogenous TFR1 locus in the germline of the animal.

Genetically modified animals can express a human TFR1 and/or a chimeric (e.g., humanized) TFR1 from endogenous mouse loci, wherein the endogenous mouse TFR1 gene has been replaced with a human TFR1 gene and/or a nucleotide sequence that encodes a region of human TFR1 sequence or an amino acid sequence that is at least 10%, 20%, 30%, 40%, 50%, 60%, 70&, 80%, 90%, 95%, 96%, 97%, 98%, or 99% identical to the human TFR1 sequence. In various embodiments, an endogenous non-human TFR1 locus is modified in whole or in part to comprise human nucleic acid sequence encoding at least one protein-coding sequence of a mature TFR1 protein.

In some embodiments, the genetically modified mice express the human TFR1 and/or chimeric TFR1 (e.g., humanized TFR1) from endogenous loci that are under control of mouse promoters and/or mouse regulatory elements. The replacement(s) at the endogenous mouse loci provide non-human animals that express human TFR1 or chimeric TFR1 (e.g., humanized TFR1) in appropriate cell types and in a manner that does not result in the potential pathologies observed in some other transgenic mice known in the art. The human TFR1 or the chimeric TFR1 (e.g., humanized TFR1) expressed in animal can maintain one or more functions of the wild-type mouse or human TFR1 in the animal. For example, human or non-human TFR1 ligands (e.g., transferrin) can bind to the expressed TFR1. Furthermore, in some embodiments, the animal does not express endogenous TFR1. In some embodiments, the animal expresses a decreased level of endogenous TFR1 as compared to a wild-type animal. As used herein, the term "endogenous TFR1" refers to TFR1 protein that is expressed from an endogenous TFR1 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human TFR1 (NP_003225.2) (SEQ ID NO: 2). In some embodiments, the genome comprises a sequence encoding an amino acid sequence that is at least 70%, 75%, 80%, 85%, 90%, 95%, 99%, or 100% identical to SEQ ID NO: 9.

The genome of the genetically modified animal can comprise a replacement at an endogenous TFR1 gene locus of a sequence encoding a region of endogenous TFR1 with a sequence encoding a corresponding region of human TFR1. In some embodiments, the sequence that is replaced is any sequence within the endogenous TFR1 gene locus, e.g., exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, 5'-UTR, 3'-UTR, intron 1, intron 2, intron 3, intron 4, intron 5, intron 6, intron 7, intron 8, intron 9, intron 10, intron 11, intron 12, intron 13, intron 14, intron 15, intron 16, intron 17, intron 18, etc. In some embodiments, the sequence that is replaced is within the regulatory region of the endogenous TFR1 gene. In some embodiments, the sequence that is replaced is exon 4, exon 5, exon 6, exon 6, exon 8, exon 9, exon 10, exon 11, exon 12, exon 13, exon 14, exon 15, exon 16, exon 17, exon 18, exon 19, or a portion thereof, of an endogenous mouse TFR1 gene locus.

The genetically modified animal can have one or more cells expressing a human or chimeric TFR1 (e.g., humanized TFR1) having, from N-terminus to C-terminus, a cytoplasmic region, a transmembrane region, and an extracellular region. In some embodiments, the extracellular region comprises a sequence that is at least 50%, 60%, 70%, 80%, 90%, 95%, 99% identical to the extracellular region of human TFR1. In some embodiments, the extracellular region of the humanized TFR1 has a sequence that has at least 10, 20, 30, 40, 50, 60, 70, 80, 90, 100, 150, 200, 250, 300, 350, 400, 450, 500, 550, 600, 620, 650, 660, 665, 666, 667, 668, 669, 670, 671, or 672 amino acids (e.g., contiguously or non-contiguously) that are identical to human TFR1. In some embodiments, the extracellular region of the humanized TFR1 has a sequence that is 5-760 or 10-672 amino acids (e.g., contiguously or non-contiguously). Because human TFR1 and non-human TFR1 (e.g., mouse TFR1) sequences, in many cases, are different, antibodies that bind to human TFR1 will not necessarily have the same binding affinity with non-human TFR1 or have the same effects to non-human TFR1. Therefore, the genetically modified animal having a human or a humanized extracellular region can be used to better evaluate the effects of anti-human TFR1 antibodies in an animal model. In some embodiments, the genome of the genetically modified animal comprises a sequence encoding an amino acid sequence that corresponds to a portion or the entire sequence of exon 4, exon 5, exon 6, exon 7, exon 8, exon 9, exon 10, exon 11, exon 12, exon 13, exon 14, exon 15, exon 16, exon 17, exon 18, and/or exon 19 of human TFR1, a portion or the entire sequence of extracellular region of human TFR1, or a portion or the entire sequence of amino acids 89-760 of SEQ ID NO: 2.

In some embodiments, the genome of the genetically modified animal comprises a portion of exon 4, exons 5-18, and a portion of exon 19 of human TFR1 gene. In some embodiments, the portion of exon 4 includes at least 50, 70, 100, 130, 150, 160, 165, 166, 167, 168, 169, 170, 180, 190, or 196 nucleotides. In some embodiments, the portion of exon 19 includes at least 100, 200, 220, 230, 235, 236, 237, 238, 239, 240, 241, 242, 243, 244, 245, 250, 270, 300, 500, 700, 1000, 1300, 1500, 1700, 2000, 2200, 2500, 2700, 2900, or 2901 nucleotides. In some embodiments, the genome of the genetically modified animal comprises about 20-63430, about 20-22158, about 20-5224, or about 20-2016 nucleotides (contiguous or non-contiguous nucleotides) of human TFR1 gene sequence.

In some embodiments, the non-human animal can have, at an endogenous TFR1 gene locus, a nucleotide sequence encoding a chimeric human/non-human TFR1 polypeptide, wherein a human portion of the chimeric human/non-human TFR1 polypeptide comprises a portion of human TFR1 extracellular domain, and wherein the animal expresses a functional TFR1 on a surface of a cell of the animal. The human portion of the chimeric human/non-human TFR1 polypeptide can comprise an amino acid sequence encoded by a portion of exon 4, exons 5-18, and/or a portion of exon 19 of human TFR1. In some embodiments, the human portion of the chimeric human/non-human TFR1 polypeptide can comprise a sequence that is at least 80%, 85%, 90%, 95%, or 99% identical to amino acids 89-760 of SEQ ID NO: 2. In some embodiments, the cytoplasmic region includes a sequence corresponding to the entire or part of amino acids 1-65 of SEQ ID NO: 1. In some embodiments, the transmembrane region includes a sequence corresponding to the entire or part of amino acids 66-88 of SEQ ID NO: 1.

In some embodiments, the non-human portion of the chimeric human/non-human TFR1 polypeptide comprises transmembrane and/or cytoplasmic regions of an endogenous non-human TFR1 polypeptide.

Furthermore, the genetically modified animal can be heterozygous with respect to the replacement at the endogenous TFR1 locus, or homozygous with respect to the replacement at the endogenous TFR1 locus.

In some embodiments, the humanized TFR1 locus lacks a human TFR1 5'-UTR. In some embodiment, the humanized TFR1 locus comprises an endogenous (e.g., mouse) 5'-UTR. In some embodiments, the humanization comprises an endogenous (e.g., mouse) 3'-UTR. In appropriate cases, it may be reasonable to presume that the mouse and human TFR1 genes appear to be similarly regulated based on the similarity of their 5'-flanking sequence. As shown in the present disclosure, humanized TFR1 mice that comprise a replacement at an endogenous mouse TFR1 locus, which retain mouse regulatory elements but comprise a humanization of TFR1 encoding sequence, do not exhibit pathologies. Both genetically modified mice that are heterozygous or homozygous for humanized TFR1 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized TFR1 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized TFR1 in the genome of the animal.

Figure 2:
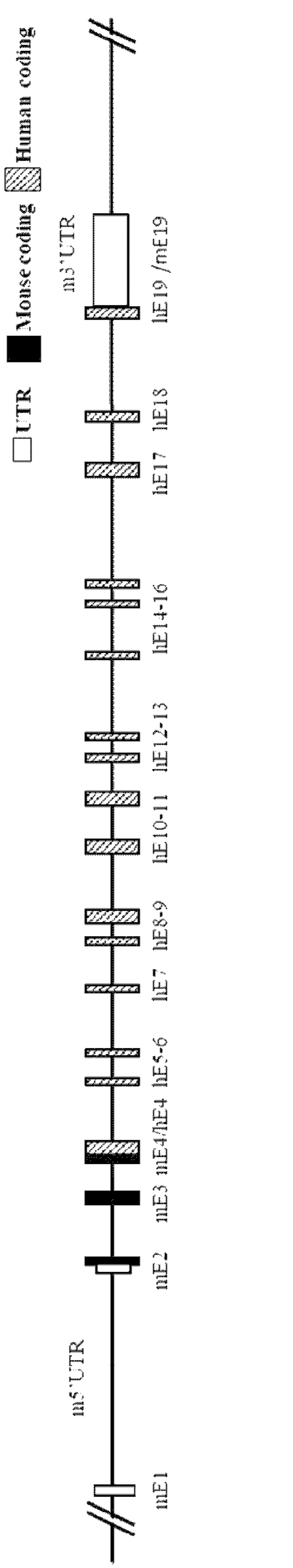
FIG. 2 is a schematic diagram showing humanized TFR1 gene locus.
Figure 3:
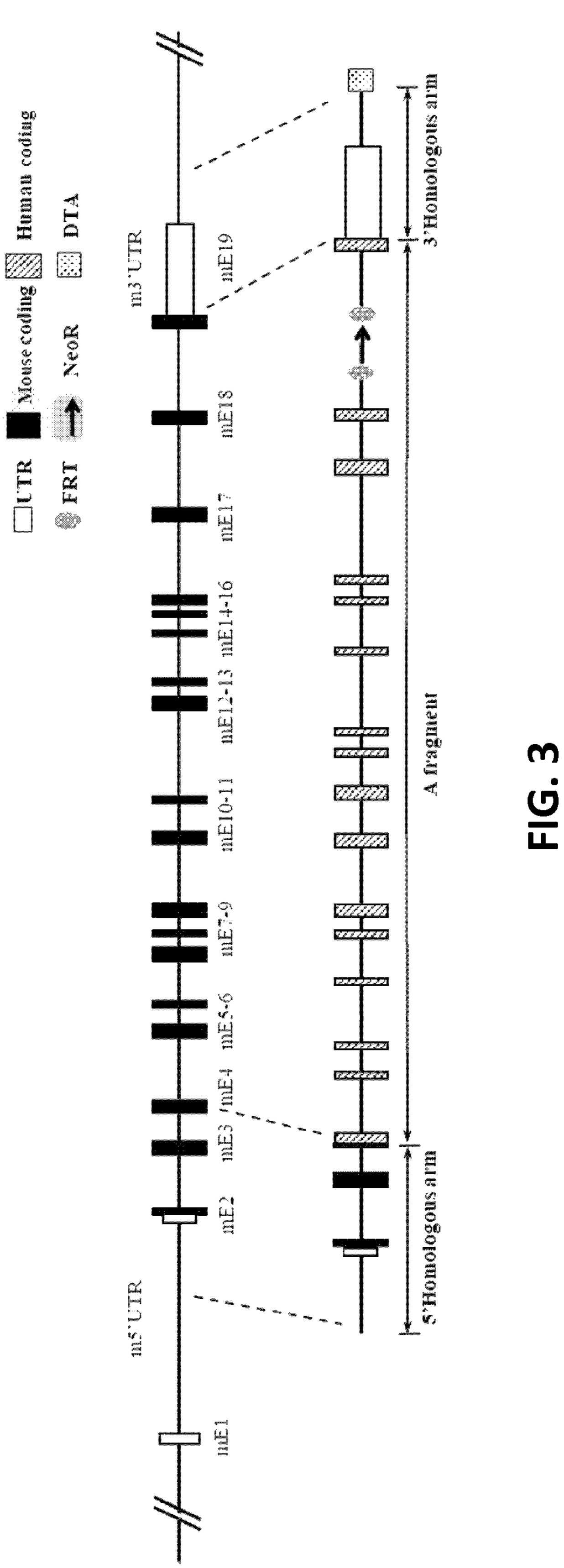
FIG. 3 is a schematic diagram showing a TFR1 gene targeting strategy.
Figure 5:
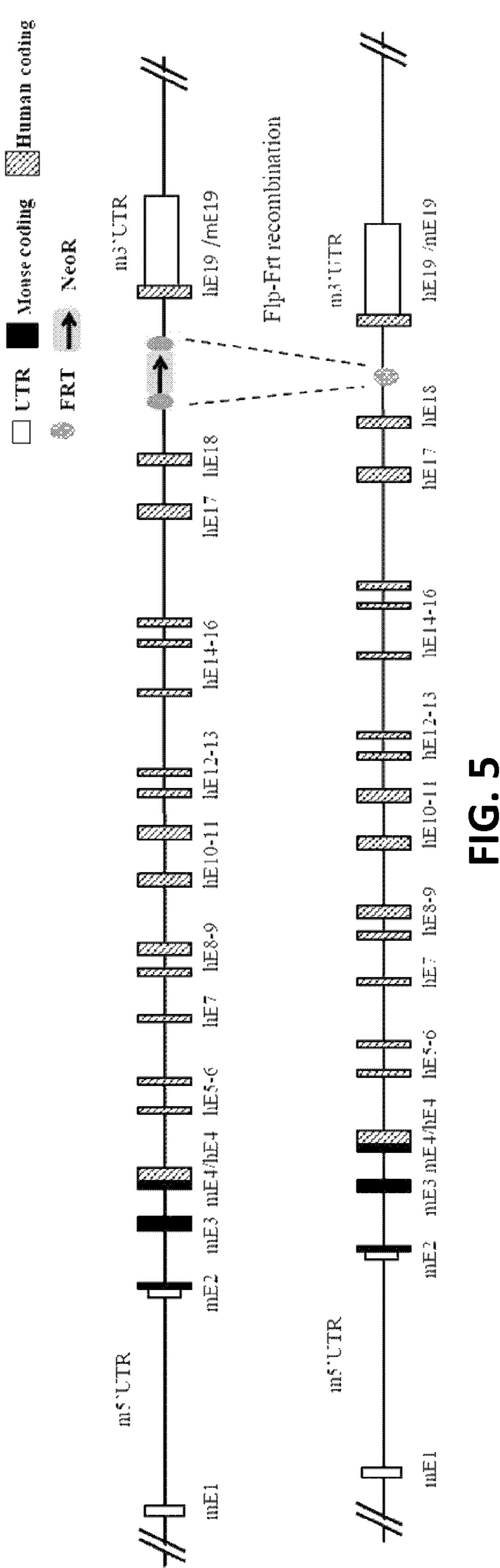
FIG. 5 is a schematic diagram showing the Flp-Frt recombination process in TFR1 gene humanized mice.
Figures 6A, 6B, 6C, 6D:
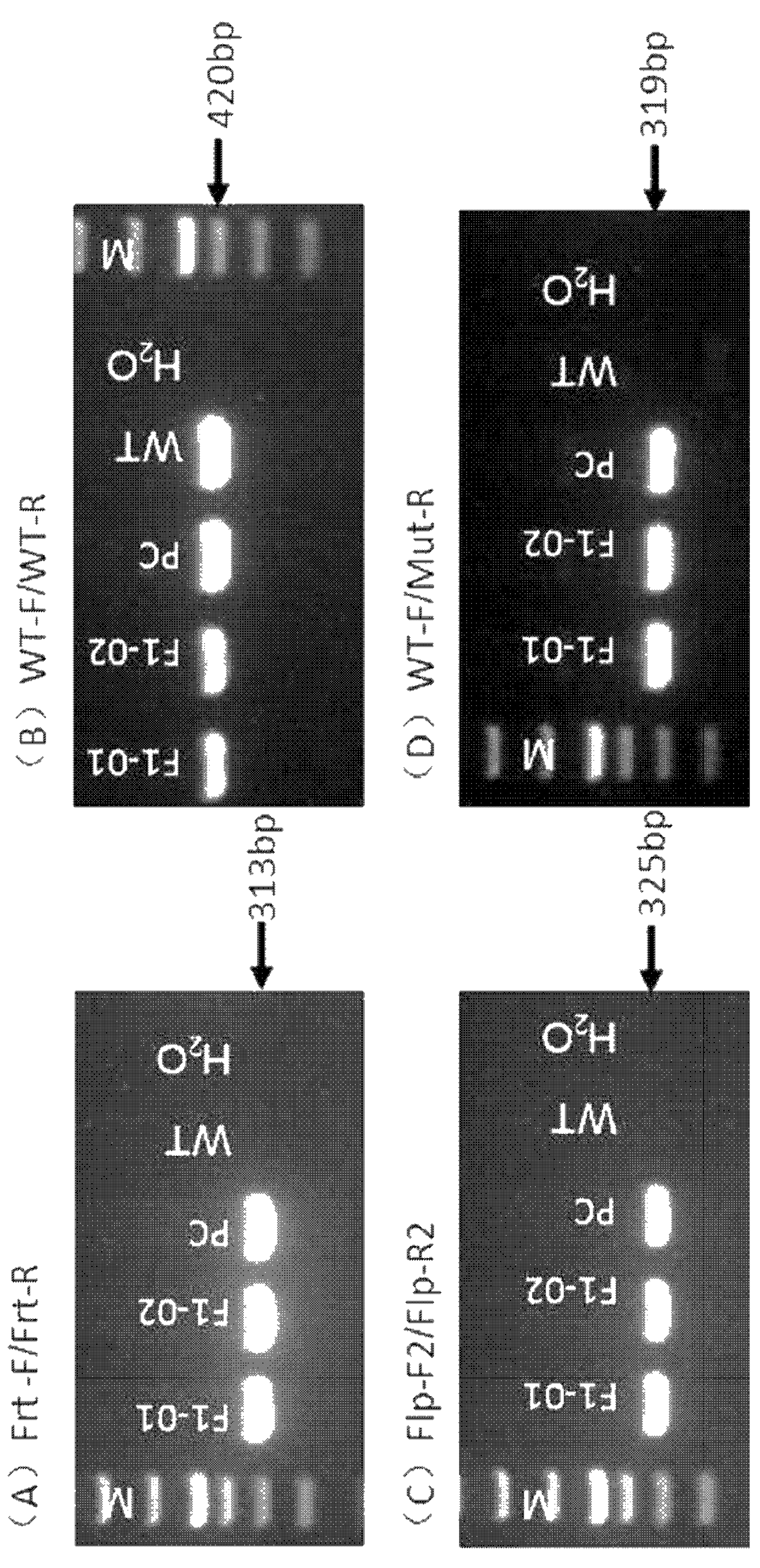
FIGS. 6A-6D show mouse tail PCR identification results of F1 generation mice by primer pairs Frt-F/Frt-R, WT-F/WT-R, Flp-F2/Flp-R2, and WT-F/Mut-R, respectively. M is a marker. PC is a positive control. WT is a wild-type control. $H_2O$ is a water control.

In some embodiments, the non-human mammal comprises the genetic construct as described herein (e.g., gene construct as shown in FIGS. 2, 3, and 5). In some embodiments, a non-human mammal expressing human or humanized TFR1 is provided. In some embodiments, the tissue-specific expression of human or humanized TFR1 protein is provided.

In some embodiments, the expression of human or humanized TFR1 in a genetically modified animal is controllable, as by the addition of a specific inducer or repressor substance. In some embodiments, the specific inducer is selected from Tet-Off System/Tet-On System, or Tamoxifen System.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cells can be obtained from the cell culture established using the same constructs and the standard cell transfection techniques. The integration of genetic constructs containing DNA sequences encoding human TFR1 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized TFR1 protein.

Vectors

The present disclosure relates to a targeting vector, comprising: a) a DNA fragment homologous to the 5' end of a region to be altered (5' arm), which is selected from the TFR1 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the TFR1 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000082.7; c) the DNA fragment homologous to the 3' end of the region to be altered (3' arm) is selected from the nucleotide sequences that have at least 90% homology to the NCBI accession number NC_000082.7.

In some embodiments, a) the DNA fragment homologous to the 5' end of a region to be altered (5' arm) is selected from the nucleotides from the position 32429794 to the position 32434036 of the NCBI accession number NC_000082.7; c) the DNA fragment homologous to the 3' end of the region to be altered (3' arm) is selected from the nucleotides from the position 32449155 to the position 32453445 of the NCBI accession number NC_000082.7.

In some embodiments, the length of the selected genomic nucleotide sequence in the targeting vector can be more than about 3 kb, about 4 kb, about 5 kb, about 6 kb, about 7 kb, about 8 kb, about 9 kb, about 10 kb, about 15 kb, about 20 kb, about 21 kb, about 22 kb, about 23 kb, about 24 kb, or about 25 kb.

In some embodiments, the region to be altered is exon 4, exon 5, exon 6, exon 7, exon 8, exon 9, exon 10, exon 11, exon 12, exon 13, exon 14, exon 15, exon 16, exon 17, exon 18, and/or exon 19 of TFR1 gene (e.g., a portion of exon 4, exons 5-18, and a portion of exon 19 of mouse TFR1 gene).

The targeting vector can further include one or more selectable markers, e.g., positive or negative selectable markers. In some embodiments, the positive selectable marker is a Neo gene or Neo cassette. In some embodiments, the negative selectable marker is a DTA gene.

In some embodiments, the sequence of the 5' arm is shown in SEQ ID NO: 3; and the sequence of the 3' arm is shown in SEQ ID NO: 4.

In some embodiments, the sequence is derived from human (e.g., 196051942-196074099 of NC_000003.12). For example, the target region in the targeting vector is a part or entirety of the nucleotide sequence of a human TFR1, preferably exon 4, exon 5, exon 6, exon 7, exon 8, exon 9, exon 10, exon 11, exon 12, exon 13, exon 14, exon 15, exon 16, exon 17, exon 18, and/or exon 19 of the human TFR1. In some embodiments, the nucleotide sequence of the humanized TFR1 encodes the entire or the part of human TFR1 protein with the NCBI accession number NP_003225.2 (SEQ ID NO: 2).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell. In some embodiments, the cell is an embryonic stem cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," *Nature Reviews Drug Discovery* 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous TFR1 gene locus, a sequence encoding a region of an endogenous TFR1 with a sequence encoding a corresponding region of human or chimeric TFR1. In some embodiments, the replacement occurs in a germ cell, a somatic cell, a blastocyst, or a fibroblast, etc. The nucleus of a somatic cell or the fibroblast can be inserted into an enucleated oocyte.

FIG. 3 shows a humanization strategy for a mouse TFR1 locus. In FIG. 3, the targeting strategy involves a vector comprising a 5' end homologous arm, a human TFR1 gene fragment, and a 3' homologous arm. The process can involve replacing endogenous TFR1 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous TFR1 sequence with human TFR1 sequence.

Thus, in some embodiments, the methods for making a genetically modified, humanized animal, can include the step of replacing at an endogenous TFR1 locus (or site), a nucleic acid encoding a sequence encoding a region of endogenous TFR1 with a sequence encoding a corresponding region of human TFR1. The sequence can include a region (e.g., a part or the entire region) of exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19 of a human TFR1 gene. In some embodiments, the sequence includes a portion of exon 4, exons 5-18, and a portion of exon 19 of a human TFR1 gene (e.g., nucleic acids 548-2566 of NM_003234.4). In some embodiments, the region is located within the extracellular region of TFR1 (e.g., amino acids 89-760 of SEQ ID NO: 2; or amino acids 89-763 of SEQ ID NO: 1). In some embodiments, the endogenous TFR1 locus is exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, and/or exon 19 of mouse TFR1. In some embodiments, the sequence includes a portion of exon 4, exons 5-18, and a portion of exon 19 of mouse TFR1 gene (e.g., nucleic acids 429-2456 of NM_011638.4).

In some embodiments, the methods of modifying a TFR1 locus of a mouse to express a chimeric human/mouse TFR1 peptide can include the steps of replacing at the endogenous mouse TFR1 locus a nucleotide sequence encoding a mouse TFR1 with a nucleotide sequence encoding a human TFR1, thereby generating a sequence encoding a chimeric human/mouse TFR1.

In some embodiments, the nucleotide sequence encoding the chimeric human/mouse TFR1 can include a first nucleotide sequence encoding a cytoplasmic region and a transmembrane region of mouse TFR1; and a second nucleotide sequence encoding an extracellular region of human TFR1.

In some embodiments, the nucleotide sequences as described herein do not overlap with each other (e.g., the first nucleotide sequence and the second nucleotide sequence do not overlap). In some embodiments, the amino acid sequences as described herein do not overlap with each other.

The present disclosure further provides a method for establishing a TFR1 gene humanized animal model, involving the following steps:

(a) providing the cell (e.g. a fertilized egg cell) based on the methods described herein;
(b) culturing the cell in a liquid culture medium;
(c) transplanting the cultured cell to the fallopian tube or uterus of the recipient female non-human mammal, allowing the cell to develop in the uterus of the female non-human mammal;
(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudopregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

In some embodiments, methods of making the genetically modified animal comprises modifying the coding frame of the non-human animal's TFR1 gene, e.g., by inserting a nucleotide sequence (e.g., cDNA sequence) encoding human or humanized TFR1 protein immediately after the endogenous regulatory element of the non-human animal's TFR1 gene. For example, one or more functional region sequences of the non-human animal's TFR1 gene can be knocked out, or inserted with a sequence, such that the non-human animal cannot express or expresses a decreased level of endogenous TFR1 protein. In some embodiments, the coding frame of the modified non-human animal's TFR1 gene can be all or part of the nucleotide sequence from exon 1 to exon 19 of the non-human animal's TFR1 gene.

In some embodiments, methods of making the genetically modified animal comprises inserting a nucleotide sequence encoding human or humanized TFR1 protein and/or an auxiliary sequence after the endogenous regulatory element of the non-human animal's TFR1 gene. In some embodiments, the auxiliary sequence can be a stop codon, such that the TFR1 gene humanized animal model can express human or humanized TFR1 protein in vivo, but does not express non-human animal's TFR1 protein. In some embodiments, the auxiliary sequence includes WPRE (WHP Posttranscriptional Response Element) and/or poly A.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized TFR1 protein, e.g., in a physiologically appropriate manner, provide a variety of uses that include, but are not limited to, developing therapeutics for human diseases and disorders, and assessing the toxicity and/or the efficacy of these human therapeutics in the animal models.

In various aspects, genetically modified animals are provided that express human or humanized TFR1, which are useful for testing agents that can decrease or block the interaction between TFR1 and TFR1 ligands (e.g., transferrin) or the interaction between TFR1 and anti-human TFR1 antibodies, testing whether an agent can increase or decrease the immune response, and/or determining whether an agent is an TFR1 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., leukemia, lymphoma, or a B or T cell tumor). In some embodiments, the anti-TFR1 antibody blocks or inhibits the TFR1-related signaling pathway.

In some embodiments, the anti-TFR1 antibody described herein can block the interaction between TFR1 and transferrin, thereby inhibiting iron import, e.g., by endocytosis. In some embodiments, the anti-TFR1 antibody described herein can block the interaction between TFR1 and gamma-aminobutyric acid receptor-associated protein (GABARAP) or human homeostatic iron regulator protein (HFE).

In some embodiments, the genetically modified animals can be used for determining effectiveness of an anti-TFR1 antibody for the treatment of cancer. The methods involve administering the anti-TFR1 antibody (e.g., anti-human TFR1 antibody) to the animal as described herein, wherein the animal has a tumor; and determining inhibitory effects of the anti-TFR1 antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT. In addition, a delicate balance is required for these antibodies, as TFR1 is also expressed on many other cells. Thus, it is important that the humanized TFR1 functions in a largely similar way as compared to the endogenous TFR1, so that the results in the humanized animals can be used to predict the efficacy or toxicity of these therapeutic agents in the human. In some embodiments, the anti-TFR1 antibody can directly target cancer cells expressing TFR1, e.g., by inducing complement mediated cytotoxicity (CMC) or antibody dependent cellular cytoxicity (ADCC) to kill the cancer cells.

In some embodiments, the tumor comprises one or more cancer cells (e.g., human or mouse cancer cells) that are injected into the animal. In some embodiments, the anti-TFR1 antibody prevents transferrin from binding to TFR1. In some embodiments, the anti-TFR1 antibody does not prevent transferrin from binding to TFR1.

In some embodiments, the genetically modified animals can be used for determining whether an anti-TFR1 antibody is a TFR1 agonist or antagonist. In some embodiments, the methods as described herein are also designed to determine the effects of the agent (e.g., anti-TFR1 antibodies) on TFR1, e.g., whether the agent can stimulate immune cells or inhibit immune cells (e.g., T cells, B cells, or NK cells), whether the agent can increase or decrease the production of cytokines, whether the agent can activate or deactivate immune cells (e.g., T cells, B cells, or NK cells), whether the agent can cross blood-brain barrier; whether the agent can upregulate the immune response or downregulate immune response, and/or whether the agent can induce complement mediated cytotoxicity (CMC) or antibody dependent cellular cytoxicity (ADCC). In some embodiments, the genetically modified animals can be used for determining the effective dosage of a therapeutic agent for treating a disease in the subject, e.g., cancer.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1-TVt/TVc)×100, where TVt and TVc are the mean tumor volume (or weight) of treated and control groups.

In some embodiments, the anti-TFR1 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the cancer described herein is lymphoma, non-small cell lung cancer, cervical cancer, leukemia, ovarian cancer, nasopharyngeal cancer, breast cancer, endometrial cancer, colon cancer, rectal cancer, gastric cancer, bladder cancer, glioma, lung cancer, bronchial cancer, bone cancer, prostate cancer, pancreatic cancer, liver and bile duct cancer, esophageal cancer, kidney cancer, thyroid cancer, head and neck cancer, testicular cancer, glioblastoma, astrocytoma, melanoma, myeloproliferation abnormal syndromes, and sarcomas. In some embodiments, the leukemia is selected from acute lymphocytic (lymphoblastic) leukemia, acute myeloid leukemia, myeloid leukemia, chronic lymphocytic leukemia, multiple myeloma, plasma cell leukemia, and chronic myelogenous leukemia. In some embodiments, the lymphoma is selected from Hodgkin's lymphoma and non-Hodgkin's lymphoma, including B-cell lymphoma, diffuse large B-cell lymphoma, follicular lymphoma, mantle cell lymphoma, marginal zone B-cell lymphoma, T-cell lymphoma, and Waldenstrom macroglobulinemia. In some embodiments, the sarcoma is selected from the group consisting of osteosarcoma, Ewing sarcoma, leiomyosarcoma, synovial sarcoma, soft tissue sarcoma, angiosarcoma, liposarcoma, fibrosarcoma, rhabdomyosarcoma, and chondrosarcoma. In a specific embodiment, the tumor is breast cancer, ovarian cancer, endometrial cancer, melanoma, kidney cancer, lung cancer, or liver cancer.

In some embodiments, the cancer described herein is a solid cancer (e.g., esophageal squamous cell carcinoma, breast cancer, ovarian cancer, lung cancer, cervical cancer, bladder cancer, osteosarcoma, pancreatic cancers, cholangiocarcinoma, renal cell carcinoma, hepatocellular carcinoma, adrenal cortical carcinoma), a cancer of the nervous system, or hematopoietic malignancies (e.g., acute lymphoblastic leukemia (ALL), chronic lymphocytic leukemia (CLL), or non-Hodgkin lymphoma (NHL)).

In some embodiments, the TFR1 antibody is designed for treating brain cancer, breast cancer, colon cancer, liver cancer, ovarian cancer, lung cancer, bone cancer, leukemia, and/or lymphoma.

In some embodiments, the anti-TFR1 antibody is designed for treating various autoimmune diseases, including rheumatoid arthritis, Crohn's disease, systemic lupus erythematosus, ankylosing spondylitis, inflammatory bowel diseases (IBD), ulcerative colitis, or scleroderma. In some embodiments, the anti-TFR1 antibody is designed for treating various immune disorders, including allergy, asthma, and/or atopic dermatitis. Thus, the methods as described herein can be used to determine the effectiveness of an anti-TFR1 antibody in inhibiting immune response. In some embodiments, the immune disorders described herein is allergy, asthma, myocarditis, nephritis, hepatitis, systemic lupus erythematosus, rheumatoid arthritis, scleroderma, hyperthyroidism, idiopathic thrombocytopeniarpura, autoimmune hemolytic anemia, ulcerative colitis, autoimmune liver disease, diabetes, pain and/or neurological disorders, etc.

In some embodiments, the anti-TFR1 antibody is designed for treating various bone diseases, e.g., fractures, bone degeneration, arthritis, bone deformities, osteoporosis, and/or necrosis of the femoral head. In some embodiments, the anti-TFR1 antibody is designed for treating various neurodegenerative diseases, e.g., cerebral ischemia, brain injury or, epilepsy, Alzheimer's disease, Parkinson's disease, amyotrophic lateral sclerosis and/or spinocerebellar ataxia.

The present disclosure also provides methods of determining toxicity of an antibody (e.g., anti-TFR1 antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

In some embodiments, the genetically modified animals described herein can be used for determining effectiveness of an anti-TFR1 antibody for treating a disease or a condition. In some embodiments, the disease or condition is related to iron uptake or iron-related metabolism. The methods can involve administering the anti-TFR1 antibody (e.g., anti-human TFR1 antibody) to the animal as described herein; and determining effects of the anti-TFR1 antibody on the disease or condition.

In some embodiments, the genetically modified animals described herein can be used for determining delivery efficiency of a therapeutic agent to cross the blood-brain barrier. The methods can involve administering the therapeutic agent (e.g., comprising an anti-TFR1 antibody or antigen-binding fragment thereof; or an anti-TFR1 bispecific or multi-specific antibody or antigen-binding fragment thereof) to the animal, and determining concentration of the therapeutic agent over time (e.g., pharmacokinetics) in brain and/or serum of the animal. In some embodiments, the therapeutic agent comprises an anti-TFR1 antibody or antigen-binding fragment thereof. In some embodiments, an agent is linked to the anti-TFR1 antibody or antigen-binding fragment thereof (e.g., the C-terminal of the anti-TFR1 antibody). In some embodiments, the anti-TFR1 bispecific or multi-specific antibody or antigen-binding fragment thereof can also target a second antigen. In some embodiments, the second antigen is a protein implicated in Alzheimer's disease (e.g., BACE1 or amyloid beta).

In some embodiments, the genetically modified animals described herein can be used for determining efficacy of a therapeutic agent to treat a disease in the central nervous system. The methods can involve administering the therapeutic agent (e.g., comprising an anti-TFR1 antibody or antigen-binding fragment thereof; or an anti-TFR1 bispecific or multi-specific antibody or antigen-binding fragment thereof) to the animal, and determining the effects of the agent on the disease.

In some embodiments, upon administration, the anti-TFR1 antibody concentration (e.g., any of the monospecific, bispecific, or multi-specific anti-TFR1 antibodies or antigen-binding fragments thereof described herein) is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than that of a control antibody (e.g., human IgG) in the brain of the animal. In some embodiments, upon administration, the anti-TFR1 antibody concentration (e.g., any of the monospecific, bispecific, or multi-specific anti-TFR1 antibodies or antigen-binding fragments thereof described herein) is less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, or less than 20% of that of a control antibody (e.g., human IgG) in the serum of the animal. In some embodiments, the concentration of the therapeutic agent described herein (e.g., any of the monospecific, bispecific, or multi-specific anti-TFR1 antibodies or antigen-binding fragments thereof described herein) is determined over a period of at least 5 hours, at least 10 hours, at least 15 hours, at least 20 hours, or at least 25 hours. At a specific time point (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours after administration), a ratio of the antibody concentration in the brain versus the antibody concentration in the serum can be calculated. In some cases, the ratio is at least 0.5, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 for the therapeutic agent described herein (e.g., any of the monospecific, bispecific, or multi-specific anti-TFR1 antibodies or antigen-binding fragments thereof described herein). In some embodiments, the ratio for the therapeutic agent described herein is at least 5-fold, 10-fold, 20-fold, 30-fold, 40-fold, 50-fold, 60-fold, 70-fold, 80-fold, 90-fold, or 100-fold as compared to the ratio for a control antibody (e.g., human IgG).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the TFR1 gene function, human TFR1 antibodies, drugs for human TFR1 targeting sites, the drugs or efficacies for human TFR1 targeting sites, the drugs for immune-related diseases and antitumor drugs.

In some embodiments, the disclosure provides a method to verify in vivo efficacy of TCR-T, CAR-T, and/or other immunotherapies (e.g., T-cell adoptive transfer therapies). For example, the methods include transplanting human tumor cells into the animal described herein, and applying human CAR-T to the animal with human tumor cells. Effectiveness of the CAR-T therapy can be determined and evaluated. In some embodiments, the animal is selected from the TFR1 gene humanized non-human animal prepared by the methods described herein, the TFR1 gene humanized non-human animal described herein, the double- or multi-humanized non-human animal generated by the methods described herein (or progeny thereof), a non-human animal expressing the human or humanized TFR1 protein, or the tumor-bearing or inflammatory animal models described herein. In some embodiments, the TCR-T, CAR-T, and/or other immunotherapies can treat the TFR1-associated diseases described herein. In some embodiments, the TCA-T, CAR-T, and/or other immunotherapies provides an evaluation method for treating the TFR1-associated diseases described herein.

Genetically Modified Animal Model With two or more Human or Chimeric Genes

The present disclosure further relates to methods for generating genetically modified animal model with two or more human or chimeric genes. The animal can comprise a human or chimeric TFR1 gene and a sequence encoding an additional human or chimeric protein.

In some embodiments, the additional human or chimeric protein can be programmed cell death protein 1 (PD-1), programmed cell death ligand 1 (PD-L1), cytotoxic T-lymphocyte-associated protein 4 (CTLA-4), TNF receptor superfamily member 4 (OX40), lymphocyte-activation gene 3 (LAG3), T-cell immunoglobulin and mucin-domain containing-3 (TIM-3), or CD73.

The methods of generating genetically modified animal model with two or more human or chimeric genes (e.g., humanized genes) can include the following steps:

(a) using the methods of introducing human TFR1 gene or chimeric TFR1 gene as described herein to obtain a genetically modified non-human animal;
(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, PD-L1, CTLA-4, OX40, LAG-3, TIM3, or CD73. Some of these genetically modified non-human animal are described, e.g., in PCT/CN2018/110069, PCT/CN2017/090320, PCT/CN2017/099574, PCT/CN2017/099577, PCT/CN2017/099575, PCT/CN2017/110435, PCT/CN2019/127084, PCT/CN2017/110494, and PCT/CN2019/119793; each of which is incorporated herein by reference in its entirety.

In some embodiments, the TFR1 humanization is directly performed on a genetically modified animal having a human or chimeric PD-1, PD-L1, CTLA-4, OX40, LAG-3, TIM3, or CD73 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-TFR1 antibody and an additional therapeutic agent for the treatment of cancer. The methods include administering the anti-TFR1 antibody and the additional therapeutic agent to the animal, wherein the animal has a tumor; and determining the inhibitory effects of the combined treatment to the tumor. In some embodiments, the additional therapeutic agent is an antibody that specifically binds to PD-1, PD-L1, CTLA-4, OX40, LAG-3, TIM3, or CD73. In some embodiments, the additional therapeutic agent is an anti-CTLA4 antibody (e.g., ipilimumab), an anti-PD-1 antibody (e.g., nivolumab), or an anti-PD-L1 antibody.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the combination treatment is designed for treating melanoma, carcinomas (e.g., pancreatic carcinoma), mesothelioma, hematological malignancies (e.g., Non-Hodgkin's lymphoma, lymphoma, chronic lymphocytic leukemia), or solid tumors (e.g., advanced solid tumors). In some embodiments, the combination treatment is designed for treating breast cancer, colon cancer, cervical cancer, fibrosarcoma, liver cancer, lung cancer, non-small cell lung cancer (NSCLC), melanoma, ovarian cancer, renal cancer, skin cancer, plasmacytoma, lymphoma, and/or leukemia.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

DraIII, EcoRV, and AseI restriction enzymes were purchased from NEB (Catalog numbers: R3510V, R3195V, and R0101M, respectively).

C57BL/6 mice and Flp transgenic mice were purchased from the China Food and Drugs Research Institute National Rodent Experimental Animal Center.

Purified anti-mouse CD16/32 Antibody was purchased from BioLegend (Catalog number: 101302).

Brilliant Violet 510™ anti-mouse CD45 Antibody was purchased from BioLegend (Catalog number: 103138).

PerCP/Cy5.5 anti-mouse TCRβ Antibody was purchased from BioLegend (Catalog number: 109228).

FITC anti-Mouse CD19 Antibody was purchased from BioLegend (Catalog number: 115506).

Brilliant Violet 605™ anti-mouse TER-119/Erythroid Cells Antibody was purchased from BioLegend (Catalog number: 116239).

PE anti-mouse CD43 Antibody was purchased from BioLegend (Catalog number: 143205).

APC anti-human CD43 Antibody was purchased from BioLegend (Catalog number: 343205).

APC anti-human CD71 Antibody was purchased from BioLegend (Catalog number: 334107).

Zombie NIR™ Fixable Viability Kit was purchased from BioLegend (Catalog number: 423106).

Brilliant Violet 605™ anti-mouse TER-119/Erythroid Cells Antibody was purchased from BioLegend (Catalog number: 116239).

PE anti-mouse CD71 Antibody was purchased from BioLegend (Catalog number: 113807).

Example 1: Generation of Mice with Humanized TFR1 Gene

The genome of a non-human animal (e.g., a mouse) can be modified to include a nucleic acid sequence encoding all or a part of a human TFR1 protein, such that the genetically modified non-human animal can express a human or humanized TFR1 protein. The mouse TFR1 gene (NCBI Gene ID: 22042, Primary source: MGI: 98822, UniProt ID: Q62351) is located at 32427714 to 32451612 of chromosome 16 (NC_000082.7), and the human TFR1 gene (NCBI Gene ID: 7037, Primary source: HGNC: 117631, UniProt ID: P02786) is located at 196018694 to 196082123 of chromosome 3 (NC_000003.12). The mouse TFR1 transcript is NM_011638.4, and the corresponding protein sequence NP_035768.1 is set forth in SEQ ID NO: 1. The human TFR1 transcript is NM_003234.4, and the corresponding protein sequence NP_003225.2 is set forth in SEQ ID NO: 2. Mouse and human TFR1 gene loci are shown in FIG. 1.

All or part of nucleotide sequences encoding human TFR1 protein can be introduced into the mouse endogenous TFR1 locus, so that the mouse expresses human or humanized TFR1 protein. Specifically, under the control of the mouse TFR1 gene regulatory element, a nucleotide sequence encoding human TFR1 protein was used to replace the corresponding mouse sequence using gene-editing techniques, to obtain a humanized TFR1 gene locus as shown in FIG. 2, thereby humanizing mouse TFR1 gene.

As shown in the schematic diagram of the targeting strategy in FIG. 3, the targeting vector contains homologous arm sequences upstream and downstream of the mouse TFR1 gene, and an "A Fragment" containing DNA sequences of human TFR1 gene. Specifically, sequence of the upstream homologous arm (5' homologous arm, SEQ ID NO: 3) is identical to nucleotide sequence of 32429794-32434036 of NCBI accession number NC_000082.7, and sequence of the downstream homologous arm (3' homologous arm, SEQ ID NO: 4) is identical to nucleotide sequence of 32449155-32453445 of NCBI accession number NC_000082.7. The human genomic DNA sequence from the TFR1 gene (SEQ ID NO: 5) is identical to nucleotide sequence of 196051942-196074099 of NCBI accession number NC_000003.12.

The targeting vector also includes an antibiotic resistance gene for positive clone screening (neomycin phosphotransferase gene, or Neo), and two Frt recombination sites flanking the antibiotic resistance gene, that formed a Neo cassette. The connection between the 5' end of the Neo cassette and the human sequence was designed as:

```
                                        (SEQ ID NO: 6)
5'-TAGCCTCCTTTAGAATTTTAACCTTAGAAGATTAGCATTAGCCAAT

TGCATCTGGCGAATCGGACCCACAAGAGCACTGAGGTCGGAAGTTCCTA

TTCTCTAGAAA-3',
```

wherein the "C" in sequence "ATTAGC" is the last nucleotide of the human sequence, and the "C" in sequence "CAATT" is the first nucleotide of the Neo cassette. The connection between the 3' end of the Neo cassette and the human sequence was designed as:

```
                                        (SEQ ID NO: 7)
5'-TCATCAGTCCAGGATACATAGATTACCACAACTCCGAGCCTGGTTC

TCAGCATTCTTTTTTCCTTACTCTGCTATAGAAA-3',
```

wherein the last "C" in sequence "CGAGC" is the last nucleotide of the Neo cassette, and the "C" in sequence "CTGGT" is the first nucleotide of the human sequence. In addition, a coding gene with a negative selectable marker (a gene encoding diphtheria toxin A subunit (DTA)) was also constructed downstream of the 3' homologous arm of the targeting vector. The mRNA sequence of the engineered mouse TFR1 after humanization and its encoded protein sequence are shown in SEQ ID NO: 8 and SEQ ID NO: 9, respectively.

The targeting vector was constructed, e.g., by restriction enzyme digestion and ligation. The constructed targeting vector sequences were preliminarily confirmed by restriction enzyme digestion, and then verified by sequencing. Embryonic stem cells of C57BL/6 mice were transfected with the correct targeting vector by electroporation. The positive selectable marker genes were used to screen the cells, and the integration of exogenous genes was confirmed by PCR (PCR primers are shown in the table below) and Southern Blot.

TABLE 3

| PCR primer sequences and target fragment length | | |
|---|---|---|
| Primer name and SEQ ID NO | Primer sequence (5'-3') | Target fragment size |
| PCR-F1 (SEQ ID NO: 10) | AGCTAGTGCTGAAGAGTAAGAGCCT | 4626 bp |
| PCR-R1 (SEQ ID NO: 11) | CACTTGATGGTGCCGGTGAAGTCTG | |
| PCR-F2 (SEQ ID NO: 12) | GCTCGACTAGAGCTTGCGGA | 5416 bp |
| PCR-R2 (SEQ ID NO: 13) | GGTGTCTGTGAGCTGCCTCACTTG | |

Figure 4:
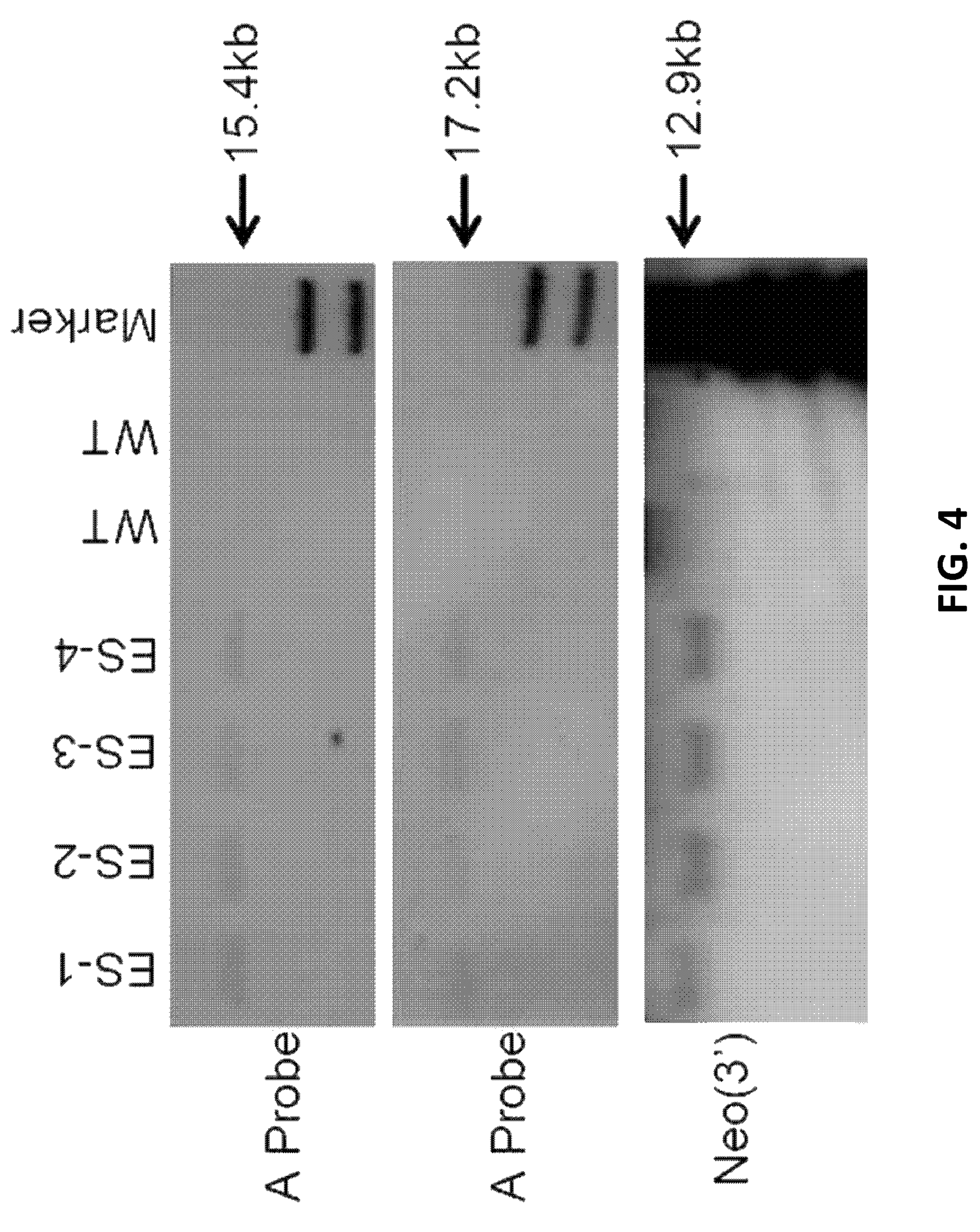
FIG. 4 shows Southern Blot results of cells after recombination using the A Probe and Neo Probe. WT is a wild-type control.

Specifically, after mouse embryonic stem cells were transfected with targeting vectors, the clones identified as positive by PCR were then verified by Southern Blot (cell DNA was digested with DraIII, EcoRV, and AseI, respectively, and hybridized with three probes) to screen out correct positive clone cells. The restriction enzymes, probes, and the size of target fragments are shown in the table below. The Southern Blot detection results are shown in FIG. 4. The results indicate that 4 PCR-positive embryonic stem cells (ES-1 to ES-4) were verified as positive clones without random insertions.

TABLE 4

| Enzymes and probes used in Southern Blot | | | |
|---|---|---|---|
| Restriction emzyme | Probe | Wild-type fragment size | Recombinant fragment size |
| DraIII | A Probe | — | 15.4 kb |
| EcoRV | A Probe | — | 17.2 kb |
| AseI | Neo (3') | — | 12.9 kb |

The following primers were used for Southern Blot identification:

A Probe:

A Probe-F:
(SEQ ID NO: 14)
5'-GGTGAGAAGAAACTAAACTATGCCA-3',

A Probe-R:
(SEQ ID NO: 15)
5'-TCTGGTTCACCCAGGTTAGAGC-3';

Neo Probe:

Neo Probe-F:
(SEQ ID NO: 18)
5'-GGATCGGCCATTGAACAAGAT-3',

Neo Probe-R:
(SEQ ID NO: 19)
5'-CAGAAGAACTCGTCAAGAAGGC-3'.

The positive clones that had been screened (black mice) were introduced into isolated blastocysts (white mice), and the resulted chimeric blastocysts were transferred to a culture medium for short-term culture and then transplanted to the fallopian tubes of the recipient mother (white mice) to produce the F0 chimeric mice (black and white). The F2 generation homozygous mice were obtained by backcrossing the F0 generation chimeric mice with wild-type mice to obtain the F1 generation mice, and then breeding the F1 generation heterozygous mice with each other. The positive mice were also bred with the Flp transgenic mice to remove the positive selectable marker genes (schematic diagram shown in FIG. 5), and then the humanized homozygous mice with a humanized TFR1 gene were obtained by breeding the heterozygous mice with each other.

The genotype of the TFR1 gene humanized mice can be verified by PCR using primers shown in the table below. The identification results of exemplary F1 generation mice (Neo cassette removed) are shown in FIGS. 6A-6D, wherein two mice numbered F1-01 and F1-02 were identified as positive heterozygous mice. PCR primers used are shown in the table below.

TABLE 5

| PCR primer sequences and target fragment length | | |
|---|---|---|
| Primer name and SEQ ID NO | Primer sequence (5'-3') | Target fragment size (bp) |
| WT-F (SEQ ID NO: 20) | AGTAAGACAAGGTGTGCACCCATGT | WT: 420 |
| WT-R (SEQ ID NO: 21) | TCAGGACTGAACTTGGGAAGTTGAG | |
| WT-F (SEQ ID NO: 20) | AGTAAGACAAGGTGTGCACCCATGT | Mut: 319 |
| Mut-R (SEQ ID NO: 22) | ATATAAGCGACGTGCTGCAGGGAAG | |
| Frt-F (SEQ ID NO: 23) | AGGCCGGTCTCGAACTCCCAACC | Mut: 313 |
| Frt-R (SEQ ID NO: 24) | GAGCCACTGTACCCAGCCAGCTGAT | |
| Flp-F2 (SEQ ID NO: 25) | GACAAGCGTTAGTAGGCACATATAC | Mut: 325 |
| Flp-R2 (SEQ ID NO: 26) | GCTCCAATTTCCCACAACATTAGT | |

The results indicate that genetically engineered mice with a humanized TFR1 gene can be constructed using the methods described herein. The mice can be stably passaged without random insertions.

Expression of humanized TFR1 protein in positive mice can be confirmed, e.g., by flow cytometry or fluorescence-activated cell sorting (FACS). Specifically, one 7-week-old female C57BL/6 wild-type mouse and one 7-week-old female TFR1 gene humanized heterozygous mouse were selected. Bone marrow tissues were collected after euthanasia by cervical dislocation, and the cells were stained with Purified anti-mouse CD16/32 Antibody (an anti-mouse CD16/32 antibody); Brilliant Violet 510™ anti-mouse CD45 Antibody (an anti-mouse CD45 antibody); PerCP/Cy5.5 anti-mouse TCRβ Antibody (an anti-mouse TCRβ antibody); FITC anti-Mouse CD19 Antibody (an anti-mouse CD19 antibody); Brilliant Violet 605™ anti-mouse TER-119/Erythroid Cells Antibody (an anti-mouse TER-119 antibody); PE anti-mouse CD43 Antibody (an anti-mouse CD43 antibody); APC anti-human CD43 Antibody (hCD43-PE; an anti-human CD43 antibody); PE anti-mouse CD71 Antibody (mTFR1; an anti-mouse TFR1 antibody); and APC anti-human CD71 Antibody (hTFR1; an anti-human TFR1 antibody), followed by flow cytometry detection.

The results showed that 50.6% of B cells (characterized by mCD45+ mCD19+) in the spleen of the C57BL/6 mouse were mTFR1 positive (characterized by mCD45+ mCD19+ mTFR1+), and 0.20% were hTFR1 positive (characterized as mCD45+ mCD19+ hTFR1+). In the spleen of the TFR1 gene humanized heterozygous mouse, 32.9% of B cells were mTFR1 positive (characterized by mCD45+ mCD19+ mTFR1+) and 11.3% were hTFR1 positive (characterized by mCD45+ mCD19+ hTFR1+). The results showed that expression of mouse TFR1 but not humanized TFR1 was detected in wild-type mouse splenocytes; whereas expression of both mouse TFR1 and humanized TFR1 were detected in the TFR1 gene humanized heterozygous mouse in vivo. The above experimental results indicate that TFR1 can be expressed normally in TFR1 gene humanized mice.

Figure 7A:
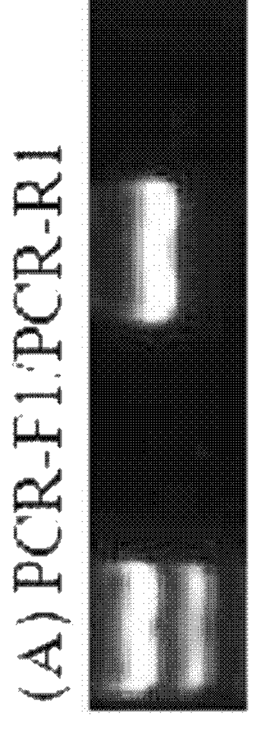
FIGS. 7A-7C show RT-PCR detection results of humanized TFR1 mRNA, mouse TFR1 mRNA, and GAPDH mRNA, respectively, in splenocytes of wild-type C57BL/6 mice (+/+) and TFR1 gene humanized homozygous mice (H/H). M is a marker. $H_2O$ is a water control. GAPDH is an internal reference.
Figure 7B:
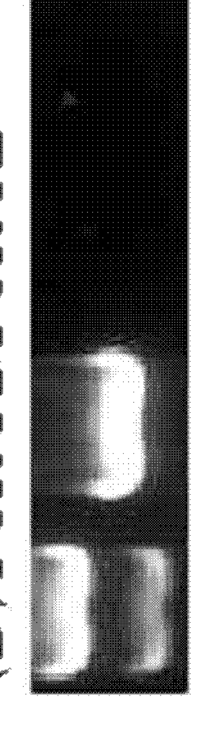
Figure 7C:
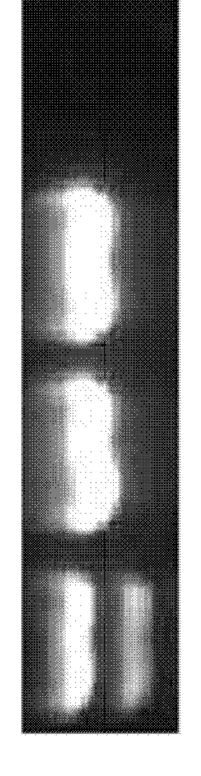

F2 generation TFR1 gene humanized homozygous mice were obtained by cross-breeding F1 generation heterozygous mice. Transcription of mRNA in TFR1 gene humanized homozygous mice was detected by RT-PCR. Specifically, one 7-week-old female C57BL/6 wild-type mouse and one TFR1 gene humanized homozygous mouse (generated using the methods described herein) were selected. Mouse splenocytes were collected after euthanasia by cervical dislocation. Cellular RNA was extracted according to the instructions of the TRIzol™ kit. The extracted cellular RNA was then reverse transcribed into cDNA, and then detected by RT-PCR using the primers shown below. As shown in FIGS. 7A-7C, only mouse TFR1 mRNA, but not humanized TFR1 mRNA, was detected in the C57BL/6 wild-type mouse. By contrast, only humanized TFR1 mRNA, but not mouse TFR1 mRNA, was detected in the TFR1 gene humanized homozygous mouse.

The following primers were used in RT-PCR detection:

```
PCR-F1:
                              (SEQ ID NO: 27)
5'-CTCTGCTTTGCAGCTATTGCAC-3',

PCR-R1:
                              (SEQ ID NO: 28
5'-CAGGATTCTCCACCAGGTAAACA-3';
```

-continued

```
PCR-F2:
                              (SEQ ID NO: 29)
5'-GTTCGAGAGTCACCACGCTGAG-3',

PCR-R2:
                              (SEQ ID NO: 30)
5'-GGCAACCCTGATGACTGAGATG-3';

GAPDH-F:
                              (SEQ ID NO: 16)
5'-TCACCATCTTCCAGGAGCGAGA-3',

GAPDH-R:
                              (SEQ ID NO: 17)
5'-GAAGGCCATGCCAGTGAGCTT-3'.
```

Similar methods using flow cytometry as described above can be used to verify the expression of humanized TFR1 protein in TFR1 gene humanized homozygous mice. Specifically, one 7-week-old female C57BL/6 wild-type mouse and one 7-week-old female TFR1 gene humanized homozygous mouse were selected. Bone marrow tissues were collected after euthanasia by cervical dislocation, and the cells were stained with Purified anti-mouse CD16/32 Antibody (an anti-mouse CD16/32 antibody); Brilliant Violet 605™ anti-mouse TER-119/Erythroid Cells Antibody (an anti-mouse TER-119 antibody); PE anti-mouse CD71 Antibody (mTFR1; an anti-mouse TFR1 antibody); and APC anti-human CD71 Antibody (hTFR1; an anti-human TFR1 antibody), followed by flow cytometry detection. The results showed that 14.2% of erythroid cells (characterized by mTer119+) in the bone marrow of C57BL/6 mouse were mTFR1 positive (characterized by mTer119+ mTFR1+), and 0.087% were hTFR1 positive (characterized by mTer119+ hTFR1+). In the bone marrow of the TFR1 gene humanized homozygous mouse, 0.04% of erythroid cells were mTFR1 positive and 10.1% were hTFR1 positive. The results indicate that the TFR1 gene humanized mice generated using the methods described herein can successfully express humanized TFR1 protein in vivo.

Further, leukocytes and T cells in the spleen, lymph nodes, and peripheral blood of wild-type C57BL/6 mice and TFR1 gene humanized homozygous mice were collected for immuno-phenotyping detection by flow cytometry. Routine blood tests and biochemical tests were also performed. The results showed that the percentages of leukocyte subtypes (including B cells, T cells, NK cells, CD4+ T cells, CD8+ T cells, granulocytes, dendritic cells (DC cells), macrophages, monocytes) and T cell subtypes (including CD4+ T cells, CD8+ T cells, and Treg cells), as well as the routine blood tests and biochemical tests in each tissue sample of the TFR1 gene humanized homozygous mice were basically the same as those detected in C57BL/6 wild-type mice. The results indicate that humanization of TFR1 gene did not significantly affect the differentiation of leucocytes and T cells, development, and distribution of leukocytes and T cells in spleen, lymphoid tissue and peripheral blood in mice.

Figures 8A, 8B, 8C:
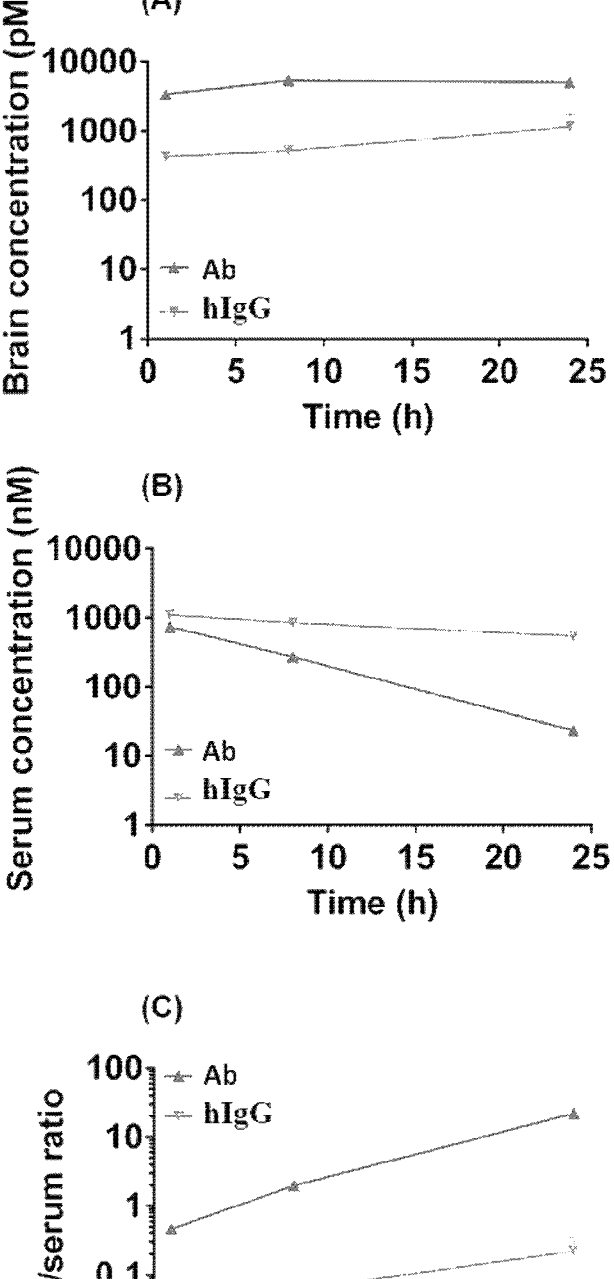
FIG. 8A shows the PK detection result of anti-human TFR1 antibody Ab in mouse brain tissue as determined by ELISA. Human IgG1 (hIgG) is a control.
FIG. 8B shows the PK detection result of anti-human TFR1 antibody Ab in mouse serum as determined by ELISA. Human IgG1 (hIgG) is a control.
FIG. 8C shows the concentration ratio of anti-human TFR1 antibody Ab over time in mouse brain tissue versus serum. Human IgG1 (hIgG) is a control.

Example 2: Pharmacokinetics (PK) Detection of Anti-Human TFR1 Antibodies in Mice The PK process of anti-human TFR1 antibodies in mouse brain tissue and serum was detected as follows. TFR1 gene humanized homozygous mice were selected and randomly placed into a control group and a treatment group. The control group mice were injected with 10 mg/kg of control human IgG1 (hIgG), and the treatment group mice were injected with an equal molar amount (10.9 mg/kg) of an anti-human TFR1 antibody Ab through tail vein. Mouse brain tissue and serum samples were collected, and the concentration of anti-human TFR1 antibody Ab in mouse brain tissue and serum samples was measured by ELISA using an anti-human Fc antibody. As shown in FIGS. 8A-8C, the concentration of Ab in the brain tissue of the treatment group mice remained at a high level during the experimental period (FIG. 8A); the concentration of Ab in serum decreased with time (FIG. 8B); and the Ab concentration ratio in the brain tissue versus serum of the treatment group mice was significantly higher than that of the control group mice (FIG. 8C). The results indicate that the brain of TFR1 gene humanized mice can take up intravenously administered anti-human TFR1 antibody. Thus, the TFR1 gene humanized mice described herein can be used as an animal model to evaluate the effective delivery and efficacy evaluation of protein therapeutic drugs to the central nervous system (CNS).

Example 3: In Vivo Efficacy Verification

The TFR1 gene humanized mice generated herein can be used to evaluate the efficacy of modulators targeting human TFR1. For example, the TFR1 gene humanized homozygous mice described herein can be subcutaneously inoculated with mouse colon cancer cells MC38. When the tumor grows to about 100 $mm^3$, the mice are randomly placed into a control group and several treatment groups based on tumor size. The treatment group mice can be randomly selected and administered with drugs (e.g., antibodies) targeting human TFR1, and the control group mice can be administered with an equal volume of saline. Tumor volume and body weight of the mice can be measured, and the results can be used to effectively evaluate the in vivo safety and efficacy of drugs, e.g., by comparing changes of tumor volume and body weight of the mice.

Example 4: Generation of Double- or Multi-Gene Humanized Mice

The TFR1 gene humanized mice generated using the methods described herein can also be used to generate double- or multi-gene humanized mouse models. For example, in Example 1, the embryonic stem (ES) cells for blastocyst microinjection can be selected from mice comprising other genetic modifications such as modified (e.g., human or humanized) PD-1, PD-L1, CTLA-4, OX40, LAG3, TIM3, and/or CD73 genes. Alternatively, embryonic stem cells from humanized TFR1 mice described herein can be isolated, and gene recombination targeting technology can be used to obtain double-gene or multi-gene-modified mouse models of TFR1and other gene modifications. In addition, it is also possible to breed the homozygous or heterozygous TFR1 gene humanized mice obtained by the methods described herein with other genetically modified homozygous or heterozygous mice, and the offspring can be screened. According to Mendel's law, it is possible to generate double-gene or multi-gene modified heterozygous mice comprising modified (e.g., human or humanized) TFR1 gene and other genetic modifications. Then the heterozygous mice can be bred with each other to obtain homozygous double-gene or multi-gene modified mice. These double-gene or multi-gene modified mice can be used for in vivo validation of gene regulators targeting human TFR1 and other genes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified, non-human animal whose genome comprises at least one chromosome comprising a sequence encoding a chimeric TFR1 (Transferrin Receptor Protein 1), wherein the sequence encoding the chimeric TFR1 is operably linked to an endogenous TFR1 gene's regulatory element in the at least one chromosome; wherein the chimeric TFR1 comprises the extracellular region of human TFR1 and the cytoplasmic region of endogenous TFR1; wherein the animal detectably expresses the chimeric TFR1 on the surface of one or more cells.

2. The animal of claim 1, wherein the chimeric TFR1 comprises an amino acid sequence that is at least 90% identical to the sequence set forth by SEQ ID NO: 9.

3. The animal of claim 1, wherein the chimeric TFR1 comprises an amino acid sequence that is at least 75% identical to amino acids 89-760 of the sequence set forth by SEQ ID NO: 2.

4. The animal of claim 1, wherein the animal is a rodent.

5. The animal of claim 1, wherein the animal is a mouse.

6. The animal of claim 1, wherein the animal does not express endogenous TFR1 or expresses a decreased level of endogenous TFR1.

7. A genetically-modified, non-human animal whose genome comprises a replacement of a portion of an endogenous TFR1 gene encoding the extracellular region of endogenous TFR1 with the corresponding human nucleic acid sequence encoding the extracellular region of human TFR1; wherein the animal detectably expresses a chimeric TFR1 on the surface of one or more cells.

8. The animal of claim 7, wherein the extracellular region of the chimeric TFR1 comprises a sequence that is at least 90% identical to the extracellular region of human TFR1.

9. The animal of claim 7, wherein the animal is heterozygous or homozygous with respect to the replacement of the portion of the endogenous TFR1 gene at the animal's genome.

10. A method for making a genetically-modified, non-human animal, comprising: replacing in the genome of the animal, the portion of an endogenous TFR1 gene encoding the extracellular region of endogenous TFR1 with the corresponding human nucleic acid sequence encoding the extracellular region of human TFR1.

11. The method of claim 10, wherein the corresponding human nucleic acid sequence comprises a portion of exon 4, exon 5, exon 6, exon 7, exon 8, exon 9, exon 10, exon 11, exon 12, exon 13, exon 14, exon 15, exon 16, exon 17, exon 18, and a portion of exon 19, of a human TFR1 gene.

12. The animal of claim 1, wherein the chimeric TFR1 comprises an amino acid sequence that is at least 95% identical to the sequence set forth by SEQ ID NO: 9.

13. The animal of claim 1, wherein the chimeric TFR1 comprises an amino acid sequence that is at least 90% identical to amino acids 89-760 of the sequence set forth by SEQ ID NO: 2.

* * * * *

SEQUENCE LISTING

```
Sequence total quantity: 31
SEQ ID NO: 1            moltype = AA  length = 763
FEATURE                 Location/Qualifiers
source                  1..763
                        mol_type = protein
                        organism = Mus musculus
SEQUENCE: 1
MMDQARSAFS NLFGGEPLSY TRFSLARQVD GDNSHVEMKL AADEEENADN NMKASVRKPK  60
RFNGRLCFAA IALVIFFLIG FMSGYLGYCK RVEQKEECVK LAETEETDKS ETMETEDVPT  120
SSRLYWADLK TLLSEKLNSI EFADTIKQLS QNTYTPREAG SQKDESLAYY IENQFHEFKF  180
SKVWRDEHYV KIQVKSSIGQ NMVTIVQSNG NLDPVESPEG YVAFSKPTEV SGKLVHANFG  240
TKKDFEELSY SVNGSLVIVR AGEITFAEKV ANAQSFNAIG VLIYMDKNKF PVVEADLALF  300
GHAHLGTGDP YTPGFPSFNH TQFPPSQSSG LPNIPVQTIS RAAAEKLFGK MEGSCPARWN  360
IDSSCKLELS QNQNVKLIVK NVLKERRILN IFGVIKGYEE PDRYVVVGAQ RDALGAGVAA  420
KSSVGTGLLL KLAQVFSDMI SKDGFRPSRS IIFASWTAGD FGAVGATEWL EGYLSSLHLK  480
AFTYINLDKV VLGTSNFKVS ASPLLYTLMG KIMQDVKHPV DGKSLYRDSN WISKVEKLSF  540
DNAAYPFLAY SGIPAVSFCF CEDADYPYLG TRLDTYEALT QKVPQLNQMV RTAAEVAGQL  600
IIKLTHDVEL NLDYEMYNSK LLSFMKDLNQ FKTDIRDMGL SLQWLYSARG DYFRATSRLT  660
TDFHNAEKTN RFVMREINDR IMKVEYHFLS PYVSPRESPF RHIFWGSGSH TLSALVENLK  720
LRQKNITAFN ETLFRNQLAL ATWTIQGVAN ALSGDIWNID NEF                  763

SEQ ID NO: 2            moltype = AA  length = 760
FEATURE                 Location/Qualifiers
source                  1..760
                        mol_type = protein
                        organism = Homo sapiens
SEQUENCE: 2
MMDQARSAFS NLFGGEPLSY TRFSLARQVD GDNSHVEMKL AVDEEENADN NTKANVTKPK  60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
```

-continued

```
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                        760

SEQ ID NO: 3            moltype = DNA  length = 4243
FEATURE                 Location/Qualifiers
source                  1..4243
                        mol_type = other DNA
                        organism = synthetic construct
SEQUENCE: 3
gattgggaga gaagtcaagg atctcatagg tggtcaggga gctacaactg cagtagtaaa  60
gaagtaggac ttaaaagaac agggccggca ctaatttga ggatctagat cgggccctca  120
attaaggaac ttcctttgt gtgaactcag aatttgaaat gaaatgtgct tgtcagaacc  180
attgcatggc ttattttta atgaaaagtc tggctagtat ctgcttatct tccagcttcc  240
agctcaaagt taaggtcata gatcaaaaga actatgtctt tatcttagtt gtatcttaat  300
ttttattaga attgaatggt tttcctaatg tttggtaaca tcaaaggtgt gtaagtaaaa  360
gtgagaaatc aagattaact ttctcttggc aaagattgtt gacattggtg acatcttgga  420
ccaaatgaga attgtttac ttttaaatgt cccatcaaca gctctcagtt aggctgttct  480
atctggtttg tcttgccatg cttgcagagt atagatttga caatttgaaa attcaaaaag  540
ctatataaat aggtatgttg ctatatgtaa gattttaaat gagtcagtta agacttaaag  600
aataactggg tttattttat cttgtcaggt tatcactgtg tagaccaggt tgaccttgaa  660
aacaaattct ctgcttccca agtgctggga ttaaaggcgt gtgtcactag ctctgacact  720
ggctactttg gaactactat ggtgttcaca aatgcagagt tgagtgttgg gattaaatgg  780
aaatttcatg tcttttttt taactttccc ttctacacag ggcttctctg tgtagtcctg  840
gctgtccttg tagctctaga ctaggctgaa ttcaaactca gatccaccca cctaagtgct  900
gagattaaag gcatgtgcca ccactgccca gttctgaatt gttggggttt tttttttgtt  960
gttattctta attttagttc gatgaattaa aatcgaaata acttgtttct tagaaaaata  1020
aggtgtaatt gggttataaa gccaaattta gacattaata ccaacagcct gtttaggctc  1080
aaaattgttc aatcatttta ttagtattat tattaatcat atcaacttga gacctgtttg  1140
ggaaagcaga atattttagg gatagctatt tcagacaagc attaatgtgt tagctgtttt  1200
tttcccccta gaatatgatt aaaattggct cagggtgggg ccttctagtt ctggctctag  1260
cgattgggtc tgtttctggt gaggtggtag tgataaactg taacagaagg gacaagagat  1320
tgggcttctg agaacatgta tgatctggta tgtgacttta atcattaaag catggggatt  1380
caaaaatact aatgaatagg ccttagaact agtcctgagt gttttgtaaa ataacagtct  1440
taattctcct agtttctgga ttttttctt tgtctttgga tactaagttt aagcatttat  1500
ttggacagag tggtgcccac tagctgttct attctagtac ttgggaggca agaggcagaa  1560
cgaacatggc cagcttggac aacttaagaa aactgaaagg cttgccatcc tagtttttct  1620
tttgattaaa cacacttata ttctaactag ttttctctat cctttgggtt ttgttttgtt  1680
ttttatttgt tttgtagctc tagctggctg gcttcggaat tgcctgcctc ccaagtgcta  1740
ggattaaagg catcacagtc actacccaat tgatatcatg attcttaatt caacttctaa  1800
gaacaaatta tcacactctg aatctaacat ggaatagcat tatccatgtt cagatatctt  1860
tgtctcaagg ctcaggttta tcctttgtag ctttcttttt gctatcccac ctctattcag  1920
catccagtca aggatcactg agttggttat cagtaaatta aacattttaa ttaatgtcta  1980
ggagacaggt tatggtatag ttctcagtgc tgggaagttg acatggtagg atctcagttc  2040
atggccagcc agaactttct ggtgagatcc tggttcaagc actacagagc ttttctagaa  2100
aagtaactat atttaggagt aagtttgata taatgacaat cccatcgtaa gccttcagta  2160
acctgatgca ttggtctctg ttttaatatc aggtactccc ttgtagcagc tgagaatgat  2220
ggatcaagcc agatcagcat tctctaactt ggtaaggtac tttcatctat ctgaaaaaat  2280
gttcagtaaa aaacaaaaca aaaacatgac ttcacccagt gagtacaaga tgatacccccc  2340
aatttttttt tttttatta tatgtatgta cactgtagct gtcttcagac acaccagaag  2400
agggcgtcag atctcatcag atggttgtga gccaccatgt ggttgctggg acttgaacac  2460
tggacctttg gaaaagcagt tgggtactct tacccactga gctatcacac cagccccaat  2520
accccaaatt ttgaccagcc ttttttttt ttttttttt tttttaaat ctgaactaat  2580
ggtattaagg tgaaacagat tgcacaaaag aggtactagg tttttctttg aggcaaggtc  2640
tttctatatt gcctcaggtt gaccttaaac tccaacttcc tttttttccc caagtgctgg  2700
agattgtaga cagatatata caacacccca aaacaaatat gtttagtttc gattaagatt  2760
cattatgtgg ggctagaggg atgacttaga ggttaagaac actgcctgct cttccagagg  2820
tcctgagttc aattcccagc aaccacgtgg tggctcacaa ccatctgtaa tgggatccga  2880
tgccctcttt ctggtgtgtt tgaagacagc tacagtgtcc tcatacataa aaaaaataaa  2940
caaacagatc ttttaaaaaa aaaggtacag tgtacttata cattatataa atgaatgatt  3000
ctttaaaaaa ttaattatgg gaaatactta tgaagaatag ggtagctttg gctgttttgg  3060
aaacgttata taacaaggta gaactaaaat gtatgccagt aatcccagag gaatcattag  3120
ccagtcaggg ctagtctgag caatgtggca agataaaccc atctctttaa aaaaaaaaaa  3180
aagtattata aatagaaatg ttataggaaa caggaaatag aaaccctcga aaggctgaat  3240
gaaagagtat tagtgggctg gagagatggt tcagcggtta agagcactat ctcctgagtt  3300
cagttcccag tgaccacatg gtggctcaca gccatctgta atgagatctg acgccctctt  3360
ctggggtgtc tgaagacagc gacagtgtac tcacataaaa taaatacata aagactgtta  3420
gttagccttc atctaccatt tacagaactg ggcacagaaa ggagttcatc agttataaag  3480
ggtaactttc catatgaatg tttgtcatat tattatgcat atagtataat gaccaaacta  3540
ctgtaatgtc ttaatatttg tatctctttt ctctttttta aaaatatcag tttggtgggg  3600
aaccattgtc atacacccgg tttagccttg ctcggcaagt agatggagat aacagtcatg  3660
tggagatgaa actggctgca gatgaagaag aaaatgccga caataacatg aaggctagtg  3720
tcagaaaacc caagaggttt aatggaagac tctgctttgc agctattgca ctagtcattt  3780
tcttcttgat tggtaagaat gagtggccat tcagaaggat ttcttatgac taactagttc  3840
```

-continued

```
ttagactagc tagttcttag actagctagt tcttgtttct tttggatgag gagatgcttt  3900
gtactttaaa tggcactggg gctccctacc tgccggcaga ttaggtcctg caagatggga  3960
aacgtttaca ttatggatgt tttattagag atatgcagga catttggaat agtactaaga  4020
aaggcttcca gtaagacaag gtgtgcaccc atgtcttaaa caggtcactg taaaatatga  4080
cttagttgtg gtaatttaaa ttccattaaa ctcaggttca taattttcta ttagattctc  4140
atagtttaat taaaagtttt cagggataag ttaaaaatga gttctgtgag tttagctcta  4200
aaacttcctg tttttaggat tcatgagtgg ctacctgggc tat                    4243

SEQ ID NO: 4            moltype = DNA  length = 4291
FEATURE                 Location/Qualifiers
source                  1..4291
                        mol_type = other DNA
                        organism = synthetic construct
SEQUENCE: 4
atgtaacatg cataattaaa taagagcagg gtagtctgtt tctagacttg tgttggttgt  60
gctaaatttt cattagagct ctaaaatcta atgttaaaat tctacccaat catctaatgt  120
cttaggcagc agcttttagt gcggggttgg acctacactt caagtacaat ggataacact  180
ttccatgttt gtgatatctt ctcagattat ctttaaaatt tttgagtcct ttgtaataac  240
ttcctctttg cttcatggtc atgaaaatgt cagaaccagt tgtaagaaca atgctatatg  300
tcctgagggc attaactagt gtcttttgag gtaggagaaa gagtgtgctt gtggagggtc  360
aacgtggtag ttgggtagtt ggagattgcc ccgtctccat ctgatcttcc attgagctgt  420
atgcccttaa ggatgtagct ggtttgcatt tccctaaatt agacagtaac tttcagaaga  480
gatggaactt gttttcttgc cagcaaggtt gaaaataggt ccttagctgg accaatttgt  540
ctgtttacag gaataagtaa ggccttactg gttaaccttg gtgttcttta tgatgagacc  600
agaagccaaa gacctcaagt tttctctcct cttggcatct gccctatagt ctttagttct  660
ttgtttttat tttgttttc tttttttccc aacattttct gaaaaagaac aagttttaga  720
ctcaatttgt cagacttgaa aagaacacac tgccaagttt tggccaaagt gttagtcttc  780
aggaaagctt tctatcattt tggcactgag atatttattg tttatttatc agtgacagag  840
ttcactataa atagtgttgt ttttttttta tatatagaag ataattatcg gaagcagtgc  900
cttccataat tatgacagtt atactgtcgt tttcttttaa taaaagcagc atctgctaat  960
gagacccaca gatactggaa gttttgcact tatggtcagc acttgcaact ttaggaagga  1020
agaatgccac aatccaaata atatgagcta gaagaggatt gggttaaata agagattcct  1080
aattgagttg gggaaaaaaa tgatagtttt cctaagtgca gtgagttgtg gccaagttaa  1140
atgtcattta aaggctatgg tagtacttac atctacaaaa ttttacagct caatttattc  1200
aagatgtaac tcaaaatcaa ttttgcaaaa tttccagtac ctttgtcaca aacttaactc  1260
acattatcgg gagcagtgtc ttccataatg cataaagaac aaggtagttt ttgcctacca  1320
cagtgtctat atcggagaca gtgatctcca tatgttacac taagggtgta cgtaattatc  1380
gggaacagtg tttcccataa ttttcttcat gcaatgacat cttcagagct tgaagatcgt  1440
tagtatctaa catgaattcc taacttcctg tagctcctta gttttagttg caaaaaacat  1500
ttgtggtcat tgagcatttg gtgggtaaaa tcaactgctg taaaatcatt acttccaaga  1560
tccttttttta aaatgtgggt attttgttat ctctggttta tggaataaaa gcatacgttt  1620
ataatgtttg ctggtgacaa aggaatttaa ctatctccct ttatttgcat gttacatgtt  1680
atttcctaaa tgtagttctt agaagtttga attcattttt ggtttttggg agggtagaaa  1740
gtagagaata atgggtgttg ggaagacaaa gcttgcaaaa ggatctttat gtacctgctc  1800
atcactatgg tggctatgaa ttatgtaggt aatgagcaag atcacattaa caaagactag  1860
ttaaccatca ttacgcatct aatcagtttt gccatggggt cagttcaaag ctgccacctg  1920
agaatgtcac taggctctca gggtcttggc accactcgcc caagttatat ccaccagatt  1980
attttgagcc tcactgagtt gttttgctac tcagtccctt cagtcttcac agtgtttctc  2040
ttgtaccagt atgagtatca ccgtgcataa tgggattcca agtcttgaat gaaggcatgc  2100
attttacata gacgtctctg tgaaataacc tttgttgtaa gtggtgtttc cagtcaaagc  2160
agtaagttgg taaggtttag tcttgggtga aatgtggatc tgagtaataa gtagcttctg  2220
ctacttatca ggttattgtt ggttaaaatg tagattttga agataaaaat agatcttttg  2280
tcatgactca ctgctagaat ttgcatgacc tttactgtgt tagcttttga atgccttttg  2340
gtttggactt gccaacctat actgtctttg ctgaaatgcc cttataaatg tatacagctg  2400
gtatgtaaca atgtgaagat tccttacctg acttaataaa atacttcgat aatactgact  2460
tgtcggactc atttcatagc aaaactagct atagagttct tatatcctcc tccactatca  2520
acctcaccag agtagtagtt acgcagacac actgatctct tgatagagat tctaatctag  2580
cttcttgtcc ttagtatatt tacatagatt ctacagcaac aaaaattggt cttattttga  2640
gcctcactga gttctaaaaa ttgggcctga aaagatggta ttaactggtc ttgcagaggg  2700
cctagcttct tagcacatat ttggtttaca agtgcttata actccagcta caggatctgt  2760
ttgttaccct cttctgggat ccacaggtac tgaatgcatg aggtgcgatg gcaggcaaat  2820
atgcatacaa aaatgcccat tgcattgagt ctcattccca aagtgttttt tctttcgtgt  2880
ctttcttact ctatcattgt ggcaatccat catgacaggg aagagagaca tgatacaagt  2940
gtgaggtgac ctatcattgt ctccagacaa agcattctca attctgaaat tccaggggtt  3000
tgggcctgct cagttctgtc tggtgggcca gtccacttgc tccacatgaa cctgggagac  3060
ctgggcttaa aaatgaacag actagtctca tgtggtagcc aactttattc aggacatagt  3120
ttaaaaggat aacctgggtg ccagagagat ggctcagcag ttaagggcac tgactgctct  3180
tccagaggac cagggttcaa atcctagcac cctggcagct catctgtaat gtctgtaatt  3240
ccaagatcag acactctcac atggacatac atgcaggcca aaaaaaaaaa aaaaaatgca  3300
cataaagtta aaagagagaa atctggaatg aaaattctgc tcagcttctg aggtctctct  3360
taatgccact tccacttatc catgagcatg gggaatatct ttgcaaactt catgggccat  3420
tttggcaaaa caaaatgtgc cttctcatgg taggcccgga tactgcatga aatacaacag  3480
ttctgtacta aaccgaagct ggttgaaata gtgaccaccg ttcctgtcaa tgggttccca  3540
tggaggctac tgagttcagc aatattatcc tcatgcagct gggcttggtg gcacatgcct  3600
ttaatcccag cacgcaggag gcagaggcag gtggatttct gagttcaagg ccagcctggt  3660
ctacagagtg agttccagga cagccagggc tacacagaga aaccctgtct caaaaaaacaa  3720
aacaaaacaa caacaaatta tcctcacggt gtgggatcca ggtgagctca agatgaggtc  3780
cagcttccag agtactcgag gtttgacctt ggcagttgac aacaatggca gagagcagtg  3840
tgatggaggt ccaggaggag ctcatgagaa tcctggccaa gggtagcctc tgagatgctg  3900
```

```
ttcctctggt gtttgccaac aagcaggagt tcaaactgcc tgcaggaaag tggctgagat  3960
cacagacaaa ctggggtggc actctacacc acagggttag ttcaagtcac tcgagccacc  4020
cgcagggatg ggctttatgg aggactagac tagttgtcca atcagctcag gagacagagt  4080
tccctccctc tccctcctgt ctgtcttctg ttcctctttt atgtagcaaa cgtgactcag  4140
tggcacgcct ctcttgcact cctatgagat atcactgaaa ttattattat tattataaaa  4200
aagagaaacc gcctcactat tggtgccaag aaaggatttt ggtgtctaag catctggcct  4260
ctgggaacca atgagctgaa gagtggcatg a                                 4291

SEQ ID NO: 5            moltype = DNA  length = 22158
FEATURE                 Location/Qualifiers
source                  1..22158
                        mol_type = other DNA
                        organism = synthetic construct
SEQUENCE: 5
tgtaaagggg tagaaccaaa aactgagtgt gagagactgg caggaaccga gtctccagtg  60
agggaggagc caggagagga cttccctgca gcacgtcgct tatattggga tgacctgaag  120
agaaagttgt cggagaaact ggacagcaca gacttcaccg gcaccatcaa gtgagtgcca  180
gctgctgtgc aagtatctag acaagtaatt caagaattat gataggccac ggggaaacaa  240
taatggtgac actgtgggga atggcttgtt agagaagaca agacttgtca tgtttagcta  300
aagaggggaa ggggcctgta aaaaactgaa actatactgg taggggaaaa ggtagaactt  360
ctctggggag tctccttttt cttaaaaaat taataggccc ttgatgtttt ccccatcttt  420
gtagcttatt gcttgctgtc attctctggc tctgattttt cttcttaacc tcttgtaacg  480
ttgtactaag ctctgctttg ctgacaagga catcagtagc ttttctctgt tttaggaagc  540
aacacatgcc agaagtagcc tttttcatct ccttgatcat gggtaactgc ctgccttaag  600
tctctagtgc ttcttaattt ctgtgatact cacccattaa cccctaggcc agtcagtatc  660
cagagacaat gtctccctct ggtggaggct ggaatacggt ggcgtgctct catctcaccg  720
cagcttcatc cccctaccat agcctcctga gtagctggga ctataagcac gcagcaccac  780
acccagctaa tttttttttt ttttttttta agagatggag tctcaccatg tctcccaggc  840
cggtctgttc ttagattttt atttatttac ttatttattt tgagatggag tcttacgtgt  900
tgcccaggct ggagtgcagt ggcacgattt cagctcagtg caacctctgt ctcccaggtt  960
taagcaattc tcctacctca gtctcctgag tagctgagat cacaggcttg taccaccatg  1020
ctctgctaat ttttgtgggt tttttttttt tttttttttt tttgcagaaa cgggatttca  1080
ccatgttggc caggctggtg tctaactcct gacctcagat gatcctcctg tcttggctcc  1140
caaagtgctg gaattacagg atgaggcact gcacctggcc aaatttctat tttatattta  1200
tttatttatt ttatttgtaa tggctttctt ggcaaaaact agaaagcatg ctagacaaat  1260
tctaaaagag ctgtaacact tgtccataga gtttactat ctttgcacat acatgcctct  1320
gtgcaaagaa taaatttatc ttttcctttt tgcaagcttc ctacacttac agtggtacta  1380
taattcttta gtcttaagtt atggcatttt ctacttcatc tagttgatgc ttttgtgttt  1440
atttactgta caccagacct tatggttaaa gtgagagtat agtccacccc acaaaaatgt  1500
aagaactaat atgctgagta aatagaaaga agtatgggag atcggaccaa ggagcagttc  1560
tgcttcaggg tattcagatg cttcacaagt aggtgagaat tgaaactatg cactctgttc  1620
agcacagtat tactatctta gattttatag tagatctgga agctactcat ttcccctaaa  1680
actatcctaa gcagatacat tgtgttatga tgaggctctt gaaggagtgc tttgtagtgg  1740
gtaaagaagc tttgaagtta caagatttgg ggcaaaattt tttttctttt gtgatattct  1800
ggtcagtcta gaagttttgg gtcacagttc atttatctga actatgaggg ataatatttt  1860
gctttcaaaa caatttgttt aatccttgac ttaaatgttt attttaaagt aaacttaagt  1920
tcatttaaaa ggcatttttct cctccaggct gctgaatgaa aattcatatg tccctcgtga  1980
ggctggatct caaaaagatg aaaatcttgc gttgtatgtt gaaaatcaat ttcgtgaatt  2040
taaactcagc aaagtctggc gtgatcaaca ttttgttaag attcaggtca aagacaggta  2100
tgttgaaaga tggtaaactt atttttatac aagtagctat tttcaggtgt gctaaatata  2160
gcaaagactt tttgttagtg ttgttggctt ttttttgaaa tggagtctcg ctctgttgcc  2220
caggctggag tgcagtggca caatctctgc tcactgcagc ctttgccttc tgggttcaag  2280
tgattctcct gccttagcct ccagagcagc tgggattaca ggcgcacgcc accacgccca  2340
gctaattttt gtatttttag tagaggtggg atggtctcga acttttgacc tcaggtgatc  2400
agcccgcctg ggcctcccaa agtgctggga ttacaggcgt gagccaccgc atgcggccca  2460
aaggctttta aaataaaaat caagcttaag atttagaggt aaatttcctc aagccaaata  2520
atgcaagaca tactaaatgt aagctattgt gtttttttgga aggatgacct taggcttatt  2580
ttaacttaat ctttttaaca gcgctcaaaa ctcggtgatc atagttgata agaacggtag  2640
acttgtttac ctggtggaga atcctggggg ttatgtggcg tatagtaagg ctgcaacagt  2700
tactgtaagt aaagcaaaac agtgcatgag actcttccct attgaatcat tcaaaactca  2760
tcttttctgt tcttaggagt tataaattta cctgtaaaat gtaaatgatc atgagatatt  2820
ttggttttca accctctaat gacacagtca acatgcattg tcttctctct ctaatcactt  2880
tccccatgtc ctgttttatt ttttctttat agtactgcta gcagctgaca ttatctatgc  2940
ctttgtttcc attagaatgt gagccagatg aagaatcatg ggttagttct atttactgcc  3000
atgttgcaga gctttggaga atgcctgaca tacatagtag tatttgctaa acaaatgcat  3060
atcctccctg tggggacaga tgtaaatatc catcttggct ggggcctagt cttagcttga  3120
ttcgttaatg cttgatcttt ttctattttt gttttgagac agggtgtcac tctgttgccc  3180
tagctggagt gcagtggcgt gagcttggct cactgcattc tccaccacca cccaggctca  3240
agtgagcctc ttgagtagct gagatgtcca gttaattttt atttttattt ttattattat  3300
tattattatt attattatta ttatttggta gagacagggt tttgccatgt tggccaggct  3360
ggtcttcaat tgaaactcct gggctcaggt gattcaccac cctcagcctc ccaaagtgct  3420
gggattacag gaggaagctg cttcgcccag cccttgatct ttttaaattt aggcaaatat  3480
agtcaaatta acacagaaat agagaacaga tagatagaat aattttcagc ttaaaaatca  3540
catttgtggc tgggcgtggt ggctcacgcc tgtaatccca gcactttggg agtccaaggt  3600
gggtggatca cctaaggtca gagctaccag cctggccaac atggtgaact ctattaaaaa  3660
tacaaaaatt agccaggcgt ggtggtgggt gcctgtaatc ccagctactt gggaggctgg  3720
ggcaggagaa tcgcttgaag ccaggaggtg gaggttgcag tgagcggata ttgcgccatt  3780
gcactccagc ctgagcaaca aaagcgaaat tccatctcaa aaaaaaaaaa aaaatcacat  3840
ttgtaagtca ggcgtatctc tagtggatac ctttcggggc tggtgcagtt ctgtgttgat  3900
```

-continued

```
tccttgcctt tctggatact tgtgctttat ccctttgcct ggctgcctat aagccaggag  3960
tttagagatg ggtaggttgt tctgttaaag aacattgaag atttttgttc aacttcaagc  4020
tttctgtatt gagggcttgg ttgttagtgt cagtttatgg ctgttcatct ggactcttat  4080
gagcttagga acatcatgac acatctaaag ttggtgtatg caagtcactt tgttgtaata  4140
gatggtgttt taattttggg acagatttat tatcagacct ttcagttaaa acctatttct  4200
atgatgtcct caaggctaag attgttccag gcctccagtc ccatgaccag cctacatagg  4260
cctctttaat ctaaatgccc ttcagatgaa aggcagcatg ggataaaagc atgaaagaca  4320
taggaggcca aaaatcttga ttttattcca atagctctga cctaaaagtt gtaaagtttt  4380
ttagaactca tgtctttttt aggccttggc ctccttttat ctcttacttg ggttgcctgt  4440
cttaggtttg atctataaca ctcttctgtc tcaagatttt agagctgttc cgataccata  4500
atgctcatta aatctaatgt ctttgttcta gggtaaactg gtccatgcta attttggtac  4560
taaaaaagat tttgaggatt tatacactcc tgtgaatgga tctatagtga ttgtcagagc  4620
agggaaaatc acctttgcag aaaaggtgag tatgagttat tataatatta aatacagtac  4680
ttttggtatc ttactcttca ggtaagtgat atttcttgtt aatattctta cattctgaaa  4740
atcagcaatc ttaaactctc ataccagata atataattta ttaaaatgct caacaaatga  4800
agtaagttcc acttacctaa tcagaagtgc ttaagtgaaa gctatttctc tgtataactc  4860
agttttacgc atatacagaa ttcagctaaa agcatgtttt ataaaaagga aaattaatag  4920
ccaaacatac acaaggaact agagtggaac atatcaaaag acagtggtga tttctgcatt  4980
tttaaaaaaa gtggcagggc tcacacctgt aatcccaaca ctttaggagg ctgaggtggg  5040
aggactgctt gagccctgga ggttgtgaga tgtgactcgt gccactccag cctgagtgac  5100
agtgagactc aaaaaagtgg ttgtcttaga tgggttttttg ttatttttct tttctttttt  5160
ttttttttt ttgagacgga gtctcttgtc accctggctg gagtgcagtg gcgtgatctc  5220
agctcactgc aacctccgcc tcccaggttc aagtgatgct cctgcctcag ccttctgagt  5280
agctgggatt acaggtgccc accaccacca tgcctggcta atttttgcat tttagtaga  5340
gacagggttt cacgacgttg gcctggctgg tcttgaactc ctgacgtcag gtgatccacc  5400
tgccttggcc tcccagattg ctgggattac aggtgtgagc caccactcct ggcctttgtt  5460
attctttttt tttttttttt ttttttttg agagggagtt ttgctctttt gtccaggctg  5520
gagtgcagtg gcgcaatttt ggctcactgc aacctctgcc ttatggtttc aagcgattct  5580
cctgcctcag cttcccaaat agctgggaat acaggcgcca gccactgcgc ccagttaatt  5640
tttgtatttt tagtagagac agggtttcac catgttggcc aggctggtct cgaactcctg  5700
agcttgtgat ccccctgcct cagccttgca aggtgttggg attacaggcg tgagccacca  5760
ctcctggccc gttactctta ttttgcaaac aagtgagtta atttttcagg aagcaattaa  5820
taaattacca gataaacaat ttgaaatatt tggaagtatt ataagtttag tcctctgtaa  5880
ccatttggcc tttagcataa tgtccaggat gtattctcat ttcgtatgat cagatcttca  5940
ttttctgagc tttatatgtt ttcttttagg ttgcaaatgc tgaaagctta aatgcaattg  6000
gtgtgttgat atacatggac cagactaaat ttcccattgt taacgcagaa ctttcattct  6060
ttggacatgt gagttatttc ttgagtaaat caccgtttg agttccttga gttgttcttg  6120
gattcctgta ttagcagaaa tagcactgtg tcttccttaa ctgctctttt ttctgggagg  6180
gcgttagcag taagcaagaa gatagattac attgactttg aggctttatt atttgttgct  6240
aaaagtactt tgtcaatagt gccttgaatt tgagaatttc catatgccat gaaaacagga  6300
gtcacattgt agagccactc agatttttga ggcttcaagt tggtaaacta aggttgggct  6360
gcagccttat accaaacctg aatcttacag agaagttttg aggaagtatg tgatggagtg  6420
aattgctctt ttgttttcct aggctcatct ggggacaggt gacccttaca cacctggatt  6480
cccttccttc aatcacactc agtttccacc atctcggtca tcaggattgc ctaatatacc  6540
tgtccagaca atctccagag ctgctgcaga aaagctgttt gggtaagttt ttatttgaaa  6600
gcggtcttgc atagtgaggt tttatgatta gggaagaacg gtaatatgtt gattaaaatg  6660
ttaaacatga tgataatttt ccacatttgg gaatttggag gatggttagc tgttaccttg  6720
gtacagatat aaatgaattt ttctctataa agagatctta ataatggact ttggacttat  6780
aaacacagga gaataaggag acttataaac ccagtgaatt ccttgtgcaa gattcctggc  6840
atagcttctg ctcaagtact tctgtgctga agcacgatgc ctatagcagc ccattcagtt  6900
agtagagaga atctgttaga attcatattg ggataaaatc ctattccccg aaacatccat  6960
ttgtctggat ttttcttcta agcaatacgg tatgattcca gttaccttgt ctatagattg  7020
agaagccttg cttcttatga tggtttccag agaaaccatt tatggttgtg gctcgctcct  7080
ctggatatcc tccctgtaac gttagtgtct ctctttaaaa acagagccca gttccattag  7140
agtacgtagc attaattttg atttggatgt ggacatattt atcatttcct gttattacag  7200
gatggagatc tagtttcagg cctttatgaa agcatttatc tcctgtatga catagttct  7260
ctgatcctgt ttctttaaca taattggata gtgaaaatat attctacttg atagtctcaa  7320
atgaagaaca tctgtatata aggagtatat gaaataccat gactgttgat catgctgaga  7380
ggcctttagc ataggggagt gtgtaacata ccatgactat tgataacgct aagaggcatt  7440
tagcataggt gattttttg actcattcta cctaccacct acaaatcgta accaacctgt  7500
gaagccagcg tcccatctta tccttatgta gtaggggagt aataatgttt caacctatat  7560
ttatgtaagt aagccccctt aggagcagct attatttggg taacacagag gaattagata  7620
ggggaagcac aagatttttt ttttattttg acagtctcac tctgttgccc aggcaggagt  7680
gcagtggcat gatcctggct cactgcaacc tccacctcct gggttcaagg aattctgcct  7740
cggccttcca aagtgctggg attacaggcg tgagccaccg cacccagctg aggaatattt  7800
tttataactg agctaagaat gtgtactatc cttgttagtg gtgacagttg ggaaacataa  7860
aagtgtatta atattctttt atatattaga agaacttcat tttgagtcca tcttggtatg  7920
tattccaaat ataaactacg taagtatgtc tggcagaaag gcgcatagtt agagaagtgt  7980
tttaaaatat tgcttaatta atggtttcca attggctgcc tgcagatcaa agtaagacgc  8040
aaatggttca ccactagaga gtaagttttt ttttgttttt attttgtttt gttttgtttt  8100
gttttttttt gagacaggac ttgtgctctg ttgcccaggc tggagtgcag tggcgtgatc  8160
tcggctcact gcagcctccg cctcccaggt tcaagcgatt ctcctcctca tcctccttag  8220
tagctgggat tacaggcgca tgccaccatg cccagttaat ttttgtattt ttagtagagt  8280
cggggtttca ccatgtcggt caggctggtc ttgaactcct gaccttgtga tccacctgcc  8340
tcagcctccc aaagtgctgg gattacaggg gtgagccact tcgccgggct gagagtaagt  8400
tttgtttata tgtcctctta atctgtaact tcactggaca ggagtaaacc ctgggcaagg  8460
aacaataact cagaacttac gcctgctttc tgattctagg aatatggaag gagactgtcc  8520
ctctgactgg aaaacagact ctacatgtag gatggtaacc tcagaaagca agaatgtgaa  8580
gctcactgtg agcaatgtgc tgaaagagat aaaaattctt aacatctttg gagttattaa  8640
```

```
aggctttgta gaaccaggta aagaccgccc cccccccccc ccgccccgct ttttttttgt  8700
tttcttttct gttcctaagg atgtggctag agaaggagcg agtgtaggaa tgctggcttg  8760
gcttggtttt atgaagtgct caatcttgtc tgtcctaaag ttaattgttt atgtgttagt  8820
ttcttttttt ttttttgag aaagagtttc actcttgttg cccaggctgg agtgcagtgg  8880
tgtgatctcg gctcactgca atttccgcct cccaggttca agccattctc ctgcctcagc  8940
ctccccagta gctgggatta caggcatgcg ccaccacgcc tggctaattt tgtattttta  9000
gtagagacag ggtttctcca tgttggtcag gctccatgag gtcagagctc ctgacctcag  9060
gtgatctgcc tccctcagcc tcccaaagtg ctgggattac aggcatgagc caccgcgccc  9120
agcctatgtg tcagttttat tgggaggtaa taaggcccta ggaaattctt gttaaaaatt  9180
gaccattatg actagaaaat ctattctaag ttattgacta gaccagtgat aagcaaattt  9240
cttaaggggg cagataataa acctttgcc aggctataca gtctctcttt tagctgttca  9300
actctgtggg agcaagaaaa caggcacaga ctgtgcgtag tgaatgggca tgcgggctgt  9360
agtttgccag tccctggagt taactttaaa tgcaatcaaa cagccaacac ttactaagaa  9420
ataagtcctt ggacttaagt agtcagtaaa tttaattagt agtgtaggaa aaaagtagct  9480
ctactagtaa ggtaaaatta atattctcat gtgaattttt aattcccaga gtttttagtc  9540
agatttgaag taaggctctt ttatccttaa tacatatact gtgcttttac ctttctactg  9600
atgtgctaat tctagaaaag tttagaagct gattatataa gttctttctt cctcttttt  9660
ctttttaaa gatcactatg ttgtagttgg ggcccagaga gatgcatggg gccctggagc  9720
tgcaaaatcc ggtgtaggca cagctctcct attgaaactt gcccagatgt tctcagatat  9780
ggtcttaaaa ggtagagtac aaattttgat tcttttgaat attggtgcac tgcatacagt  9840
tctagatgtt atactgtgct ttgctcactt tgcctgcatt cctgtggttc tcatgctaga  9900
ctctagttct taaatacaag gcagattgtc ttttgttgta gctgcctttt cctttgaaac  9960
agctttccat aaagtgtctt aactgtgcta gaaatcacca gtttctttga gacagtggag  10020
ttactgagcc ctagtgctta gtgtggtgga tccagagtga taaggtggat catagtccct  10080
aagcaatcta tttgaaagca gtagcatacc tctctactca tgtactgagg cctaacagct  10140
attgaaattt tgttctgttt attcatttat tcatttttg agacagagtt tcactctgtt  10200
gcccaggctg gagtgcagtg gtgtgatctc acttagctca ctgcaacctc tgcctcccga  10260
cttcaagcaa ttctcctgcc tcagcctcct gagtagctgg gattacaggc acccacaacc  10320
acacccggcc aatttttgta tttttactag agacagggtt tcgccatgtt ggccaggcta  10380
gtctcctgac ctcaagtgat tcacccgcct cagcctccca aaatgctgct agtgagccac  10440
cgtgccctgc ctcttttgtt tattttgag cctttctgtc ctactttcca ctctttcaca  10500
ctcctaccca cccacacatt caaaatcacg tcacattctt gaatctttgg gtcttagggc  10560
aaactgcaat gcttaacttt aatacagagt acattaatgg agaaaaagat acagtgaggg  10620
aagtgggagg gatggagggc agtgtgatac atgtaacctc aaaaggtgct gtcacaaata  10680
tagtttctct gcaaactctt cttgtaactt aaatttgtga atttttattt tattttagaa  10740
ttattttttt aaaaatccaa tgtttggatt tacctctgaa gatttttctc aagatgtgca  10800
tcatcatgct tacactgttt tcaatgatct ctgggtccag aagttaagga actccaagaa  10860
tgaaattgtg aaagggtgac tactggcccc tgctatgtac tcaaaatctt atttgcagat  10920
ctcctatctt gctctttgta ggttacttta aaaaaaatta ttcctattct tttattcttt  10980
tacctggggt ctcaaaaaaa gattttgtta gtttttttt tcttttttgg ctcagaaaaa  11040
aaagattttg gaatctgcta tcttggaatt agaccttctg attcatctta agtgggatac  11100
cttccatcct tgtctgtgta taacctttcc tcaggtaaag ctaacttttt tctctttcag  11160
atgggtttca gcccagcaga agcattatct ttgccagttg gagtgctgga gactttggat  11220
cggttggtgc cactgaatgg ctagaggtat tctttatcat cccttcccat attggacacg  11280
agcttgtggg cttaggctgt tgtccagaag tgatgttttt ataggtttga ttttaccact  11340
tttgcctttg cgtttagtct cagtagagtc cagaattgaa aatgaatccc taatgctact  11400
gtatgtgata aataaacaga tttatactta ttagtgtttt cccttctctt ctagggatac  11460
ctttcgtccc tgcatttaaa ggctttcact tatattaatc tggataaagc ggttcttggt  11520
aagtatccct ttcattagct gtgtatgaat tcaggtaaac ttttttgaga tggagttttg  11580
ctcttgtcgc ccaggctgga gtgcaatggc acgatctcgg ctcactgcaa cctctgtctc  11640
ccagattcaa gcgattctcc tgccttagcc tcctgagtag ctgggattac aggtgctcac  11700
taccacaccc agctaatttt ttgtattttt agtagagaca gggcttcact atgttggcca  11760
ggatggtctc gaactcctga cctcaggcga tctgcctgcc tcggcctggg attacagatg  11820
tgggccactg tgcctggcca gataaactac tttgaagtgg aagaaagctt tttttttttt  11880
ttgagacagg gtctcactgt attgcccagg ctagagtgca gtggcacaat cttggctcac  11940
tgcagccttg acctcctggg ctcaggtgat cctcccactt cagccacctg gctaattttt  12000
tttgtagaga tggggttttg ccatgttgcc caggctggtg tcaaactcct gagttcaagc  12060
attctatgtc agctgcccaa aatgctgcgg ttacaggcat gagccattgc cctcagcctg  12120
tatcttaacc ttcctttaaa tagtctgtca agttacacag tgagcacaat tgcttgtcta  12180
gaacagtggg tagttctcag tgtggccccc agatgagtag cattaggaac tgttacgaat  12240
gcaaactgtc atgtctaccc cagacctttg agtcagaaat gggagtgttg gtctaaaaac  12300
tgggcttttt gggctgggcg cagtggtgca cgcctgtaat cccagcactt gggaggccaa  12360
ggcaggcgga tcacctgagg tcaggagttc gagaccagcc tggccaacat ggtgaaaccc  12420
cgtctctact aaaaatacca aaattagccg ggtgtggtgg cgagtacctg taatcccagc  12480
tactcaggag gctgaggtag gagaatcact tgaacccggg aggcagaggt tgcagtgagc  12540
caagatggcg ccattgccct ccagcctggg cgacagagcg agactccatc tcaaaaaaac  12600
aaacaaaaaa actgggcttt ttttttggca acccttgggg aataaaaacc tattattttc  12660
ttaaggacaa agtatcctga agcaaaaaaa cccaaacaaa gaaacaaaaa actttaacaa  12720
gcactacagg taattctgat ggactaaagt tttaggacca taagtctgga ctatattgag  12780
gtgagaagaa actaaactat gccatataga atggtactta gagagtaatt cacatcctgt  12840
tacgttgtgg catcactgat agaaatattg gataatgaaa cttctagaag agtttgaatg  12900
ttcactggca gcagaaaatt gacaaaaggg tttgaatgtt atttaaagtg cagctgtaca  12960
ttcaacagga atggggtaaa aaagaaagtg cagatgtagc tgatgagctg agaatagtga  13020
aatgtctaca tgggggaaaa aaggaaagag ttacaattaa acctctctag gttagttatt  13080
tccctgttgt atgtttgccg cagaatgtgc tgagtatagc aagcatacta tgtatagctc  13140
taacctgggt gaaccagaaa gttaaacatg aaattgctaa tgggggaggc tgcacatgtg  13200
tgggggcagt ggatttatgg gacctctagg tacctttctc ttaattttgc tgctgaacct  13260
aaaactggtc tgattttttt tttttttttt tttttttttt ttgagatgga gtctcgcttt  13320
gtcacccagg ctggagtgca gtggcgccat cccagctcac tgcaagctcc gcctcccggg  13380
```

-continued

```
ttcatgccat tctcctgcct cagcctcccg agtagctggg actacaggtg cccgccacca  13440
cacccggcta atttttttgta tttttagtag agacggggtt tcactgtgcc agccaagatg  13500
gtctcgatct cctgaccttg tgatccaccc gtctgggcct cccaaagtcc tgggattaca  13560
ggcgtgagcc accgtgcccg gcctaactgc tctgatattt ttaaaaaagg tgacttggat  13620
taaagtatgc aaactcaagg agtagtacga gcccacttga gtgaagttag cttagttgct  13680
aaagagcttg ataccaaaat tacttttgtt tacttgatga atgggatagt tgttgcacag  13740
ggccactgat ctagattact gtcttatttg tcaagtactt atagttgtag aagtagcagt  13800
gtgaaaatta tcggaatgga gaaggggcaa tgataaaaca atttattttc aggtaccagc  13860
aacttcaagg tttctgccag cccactgttg tatacgctta ttgagaaaac aatgcaaaat  13920
gtgagtatat acctcattac aaaaatgtat gacttaattt ttgttgaatc aacctgagat  13980
aaaaaacact gatatgtaaa ccgtagtcag taacaaaaaa taggaattga gaataaattt  14040
tatagcagcg ttatttaagg gatacttgcc tattgaacca tatgagatga gggctccaat  14100
cttaaagaat atgttgttta tttaggaata tataacaaaa tgccatgagg cctaagctgt  14160
agtgcagggg cccacagggg attgtctata gagtcacaat gctaaggaag gcttaaatca  14220
acttgaacta tactttgaga aggccggagg aaatattcat tgaataaaca attaccatag  14280
ttttgaatga gggagagcat gtgaaagaaa atatttgcct atgtggggtg gggggagggg  14340
agagggatag cattgggaga tatacctaac gctagatgac gagttagtgg gtgcagtgca  14400
ccagcatggc acatgtatac atatgtaact aacctgcaca atgtgcacat gtaccctaaa  14460
atttaaagta taattaaaaa aaaaataaat aaataaataa aaaagaaaat atttgcctaa  14520
tgggattaga ggctgtatat tggagtgagt aaagttagaa acaggtcaga tagcagacat  14580
tggccttgat ccaagagata ctagggatta taggatctca agcaaggtga tcatgaattt  14640
gccagttagg ttggtggcat aagatgcact agaaggaaga aaccagaaac aagataggca  14700
tagtgtgaag cccagagagg gcttttacaa ttgtgggtaa gccaccatgg ttttgtttgt  14760
ttgtttgttt gtttttgaga tggagtcttc ctctgtcttc ctccagcact caggctggag  14820
tgcaatggtg cgatcttggc tcactgcagc ctccacctcc tgggttcaag cgattctcct  14880
gcctcagcct cctgaggagc tgggactaca ggtgcacacc accacacctg gctaattttt  14940
gtatttttag tagagacggg gtttcaccat gttggccagg atggtctcaa tcccttgacc  15000
tcatgatctc ttgaccttgg cctcccaaaa tgctgggatt acaggtgtga gccaccgcgc  15060
ccagctttta ttcatttttt tttccttttt ttttttaag agataaagtc ttgctgtgtt  15120
gcccaggcta gtctcaaact tctgggctca agtgatcctc ccagctcggc ctcccaaagt  15180
gttgggattg cagttgtgaa ctaccccacc cggcctaggc ccacttttaa aatgttaatt  15240
aagaagaaaa cattttttcc tcaccataac taaaggaact gacaacatga gcctagttag  15300
taataactta aagttgagat tgttttaact atcataaata atttcttttc aagaagatat  15360
aatacaagtt ttttatttaa aaattgttat agagtaacat gttagtgact agcctgaata  15420
aataagttcc aaaaggttag ttttaatgat aatttcttat cttacaggtg aagcatccgg  15480
ttactgggca atttctatat caggacagca actgggccag caaagtgtaa gttgagaaaa  15540
gtgaatgaac aaactaatag aaaagcagag attctaccta ctacattagg tagaatctaa  15600
atctgtcctt gcattgaact tacttacacc taaagatatt cagctaaaga atttattttg  15660
gatgggggga ctagcacgat agaacagtct attctttaaa acactttcta aagacacatt  15720
ctttgtcttt gcagtgagaa actcacttta gacaatgctg ctttcccttt ccttgcatat  15780
tctggaatcc cagcagtttc tttctgtttt tgcgaggtaa gtctgttcat ttaaatgaca  15840
aatggagaga ggctctctaa aaggaagtga tctgtatttg ggaatagggc attgcaatgg  15900
gaatgcctgt gctatagtca actatgtaca tattcagagg agtaaaggaa aacaagtttt  15960
taaggacaaa tgacgaggat tacaaaatta ctttgaggta attattcttg gctaccaaga  16020
tcaataacaa ggatgacacc agtccaaggt tgacaggcag ttgctaggca gattttctca  16080
cgagagaagt tttttggtgc aaggttgcag tggcctttgt gtaaggttgt agtttttgta  16140
aaaaggaaaa aaaaaaaccc ttaatccttg ttatcagaca tacaagggtg agacccttct  16200
cttcagggtt gcatttttgt taacactagt gactccattt tgattttgac aacttgcaca  16260
tatcttagtt gttgggtttt ttttgtttgt tttttgtttt gttttttttt ttttttttga  16320
caatggtgac ttgctctgtc acccaggctg gggtgcagtg gcccgatcat ggctcactgc  16380
agcctcaagc agtcctcccc cttcagcctc caaactgttt ggattatagg caagagctac  16440
ttactacacc tggccatgga tcttcttgtg tcaactttga gaccaaattt actgcagtgc  16500
ttaaaatgtt ttaagaagtt atacacatgt gctggatgtg gtagctcacg cctgtaatcc  16560
tgtagcagga caagccgcag acaaatcccc tcagacaccg agttaaagaa ggaagggctt  16620
tatttggctg ggagctttgg caagactcac gtctccaaaa actgagctcc ccgagtgagc  16680
aattcctgac ctttttaagg gcttacaact aagggagtct gcgtgagagg gtcgtgatca  16740
attgggcaag caggggggtac gtgactgggg gttgcatgca ccggtaatta gaacagaaca  16800
gaacaggacg ggattttcac agtgcttttc tatacaatgt ctggaatcta tagataacat  16860
aactggttag gtcagggctc gatctttaac caggaccagg gtgcggcagc gctgggctgt  16920
ccacctctgc cttttagttt ttacttcttc tttctttgga ggcagaaatt gggcataaga  16980
caatatgagg ggtggtctcc tcccttaatc ccagcacttt gggaggccaa ggaaggcgga  17040
ttacgaagtc aggagtttga gactagcctg accaaaatgg tgaaaccccg tctctgctaa  17100
aaatacaaaa attagtcgga catagtggcg tgtgcctgta accccagcta ctcaggaggc  17160
tgaggcagga gaatcgcttg aacctgggag gcagaggttg cagtgagctg agatggagcc  17220
actgcactgc agcttgggtg acagagcaag accctgtctc aaaaaaaaaa gttatacaca  17280
tgtaattatt gcatgttcct tcattattag ttttaacata gacttgttaa tctcaattag  17340
cttaattagc atttgagttt attgctaaaa cttctttatg agttttaata atgaggcttg  17400
gccgagtgtg gtgggtcata cctgtaatcc cagcatttgg gaggccaagg cgggtagatc  17460
acttgaggtc aggagttcaa gaccagcctg gccaacatgg ttaaacccca tctctactaa  17520
aaatacaaaa aaattagctg ggcatggtgg cacatgccta taatcccagc tgctcaggag  17580
gctgaggtgg aagaatcgct tgaacccagg gggcagaggt tgcagtgagc cgagatcgtg  17640
ccattgcact ctagcctggg caacagagca agatcgtcta acaacaacaa aaaaaaaacc  17700
aaggctgaat ttcttgagtg attgagcagt ggctatctat tggacagtcc agctgaacag  17760
tattttcctc aggctgggtg cagtaactca cacctataat tccggcacat tgggtggctg  17820
aggtgggcag atcacttgag gccaggagtg agaccagcct gggtaacgtg cctagactat  17880
atctctacaa aaaatttttt aaattaagtg gcccagtggc cagctgtagt cccaactcct  17940
tgggaggctg aggcaggggg gtcacttgag ctaggagctt aaggctgtgg ggagccatga  18000
ttgcatcacc acgctccagc ctgggtgaca gagtgacctc gtctcaaggc tgcagggagc  18060
catgattgca tcactgcact ccagcctggg tgacagagag aggcctcgtc tcaaggctgc  18120
```

```
ggggagctgt gattgcatca ctgcactcta gcctgggtga cagagtgacc tcgtctcaag  18180
gctagaggga gccatgattg catcactgca ctccagcctg ggtgacagag agagacctcg  18240
tctcaaggct gcagggagtc atgattgcat cgctgcactc tagcctgggt gacagagacc  18300
ttgtctcaag gctgcgggga gtcatgattg cattgctgca ctctagcctg ggtgacagag  18360
agaccttgtc tcaaggctgt ggggagtcgt gattgcatca ctgcactcta gcctgggtga  18420
cagagagacc tcgtctcaag gtatgtttca tgtatcttct ctttttttcat tgataaaggc  18480
ccaaacttcc cagagagaaa aacatacagc cttaaggaat ttggctagaa gtctattcag  18540
ggcatatgat acgatagaac agggattctg tagaacctgg aagaaagtag tcactctagg  18600
agtaggttag cttgagagaa gtagcaagaa tgtacttaaa gcagcagata atgagataga  18660
attggggtaa attgcggtag gaatatgtta gaagcaaggg tggaactgtc gtcactgtta  18720
cctcgatggc gaagccagaa tgtgaggctc ttgctcttag aactcacgtg agtaccatag  18780
cctcgcgttg tcttgcagga cacagattat ccttatttgg gtaccaccat ggacacctat  18840
aaggaactga ttgagaggat tcctgagttg aacaaagtgg cacgagcagc tgcagaggtc  18900
gctggtcagt tcgtgattaa actaacccat gatgttgaat tgaacctgga ctatgagagg  18960
tacaacagcc aactgctttc atttgtgagg gatctgaacc aatacagagc agacataaag  19020
gtgagcactg attccaatta cgtttttatt ttgctgaatg tcaagtattt tgaaatgtga  19080
tgtgttcctg tgtgttcctg ttggaagggt gattgtagcc atagtacatt ttaaagtgaa  19140
ctgaggtata attgtatgta gaattggtaa cttgtttgag agaagtcggg aggctgtgga  19200
ttagagacct aggacagagc tcagcaggtg tttcagaatc cagagcagtg tcaggttttc  19260
tgtcactcat gtctcccagg cagcccgtca gtaggacacg gaatatgaag atctcagcaa  19320
ggagttgggc tgtgtgcctc tcgggcgtga cccggatgga aagacagcac agctagcagg  19380
attccatctc gtagtgatct gcgcatctaa aagtcaaata ttctattaaa cgaaactgat  19440
aagcagggtg aggtggtgca tacccgtagc cccagctact tctgctgagg caggaggatt  19500
gctggagtcc agcccaggca acatagcaaa atcccatctc taaataaatt aataaaacta  19560
atattaaagt agcttccaga ttgttttatg gtactaggag ttgattttta acagatctct  19620
taattgaagt aaatcactga caaccgaatc ttttttatatc tttttttattt ttatttttat  19680
tttatttttt ttgagagatg aagtctcgct cttgtccccc aggctggaat gcaatgacat  19740
gatctcggct cactgcaacc tccacctccc ggctttaagc gattctcctg cctcggctcc  19800
ccaggtagct gggattacag gcgtgtgcca ccatgcccag atagtttttg tgtttttagt  19860
agaagccggg gttttaccat gttggccagg ctgaagtgca gtggcgagat ctcggctcac  19920
tgtaagatgc gcctcccggg ttcacgccat tctcctgcct aagcctcccg agtagctggg  19980
actacaggtg ccggccacca cgcccggcta atttttttgta tttttagtag agccggggtt  20040
ttaccatgtt ggccaggctg gtcttgaact cctgacctca ggtgatccac ccacctcggc  20100
ctcccaaagt gctgggatca caggcatgag ccaccacgcc cggcatctta tgtctttctt  20160
gaaactaatt gtaactgttg aaaatggaac ttaccaggtg gaaataacta aatcctgaag  20220
taccttgaac caaaatgttt tcccctatag ggacattttc ccccaaaagg agaattgaac  20280
tggaaacaat atagtacata ggattatata attatgttca atttcttaat gagaatggtt  20340
ttcttacatg ctgggctcaa atatgagtgt atatcacagt ccatagagct tggaacccct  20400
gtgcaaggtg ctttcggagt cttgagctta tctgcgagtt ccttttatca gaatcttact  20460
taacgcacgt taaattagaa aggcatacaa aagaatgtcc ttagaaataa aacttctcat  20520
agcgaataat gtctgtttca ggaaatgggc ctgagtttac agtggctgta ttctgctcgt  20580
ggagacttct tccgtgctac ttccagacta acaacagatt tcgggaatgc tgagaaaaca  20640
gacagatttg tcatgaagaa actcaatgat cgtgtcatga gagtaagtga acttttggga  20700
aaggaggaac taaagtatgt gtaaaataac cgataaatct tacacttctg caaagtggac  20760
aaactctagg agtctagaat tcctttaaga agggagcatt aatggtttag ctgtcatttt  20820
ctgtttctgc tgtctaattc agaacttagt caaacctagt ctttttggaa gagacttgct  20880
gtaaaacttc catgtatgct ccaatgggga aaagaatctg aacacattta aagttttcct  20940
ttgtaaaatg aatcagtttc ctttaaaaaa atttttttttt tttttgagac agagtttcac  21000
tgttgttgcc caagctggag tgcaatggca cggtctcggc tcactgcacc ctccacctcc  21060
caggttcaag tgattctcct gccttagcct cccgagttgc tgtgattaca ggtgcccaac  21120
accacgcccg gctcattttt tgtattttta gtagaaacgg agtttcacca tgttagccag  21180
gccggtctcg aactcccaac ctcaagtgat ccacctgcct tggcctccca aagtgctggt  21240
attacaagcg tgagccgctg tgcctagcct cctttagaat tttaacctta gaagattagc  21300
attagcctgg ttctcagcat tcttttttcc ttactctgct atagaaagtc tgatcagctg  21360
gctgggtaca gtggctcatg cctgtaattc cagtactttg ggaggccgag gcaagcggat  21420
cacctgaggt caggagttca agaccagcct gaccaacatg gagaaacccc atctctacta  21480
aaaatacaaa aattagctgg gcgtggtggt gcatgcctgt aattccagct gctcaggagg  21540
ctgaggcagg agaattactt gaacccggga ggtggaggtt gcagtgagct gagatcgcgc  21600
cattgtactc cagcctgggc aacaagagcg aaactctgtc tcaacaacaa caaaaagccg  21660
ggcacggtgg ctcacacctg taatcccagc atgaattgct tgaactcggg aggtggaggg  21720
taccagtgag ccgagatagc gctgttgcac tccagtctgg gcaacaagag cgaaactctg  21780
tgtcaaaaaa aaaaaaaaaa aaaaaaagtc tgatcggcat tcttaaattt gggacatttt  21840
acatttgaag tgaactgttg ttttactaca aaagtcacag ggctgtgtaa attgccttgt  21900
gtgttgtttt cgtaggtgga gtatcacttc ctctctccct acgtatctcc aaaagagtct  21960
cctttccgac atgtcttctg gggctccggc tctcacacgc tgccagcttt actggagaac  22020
ttgaaactgc gtaaacaaaa taacggtgct tttaatgaaa cgctgttcag aaaccagttg  22080
gctctagcta cttggactat tcagggagct gcaaatgccc tctctggtga cgtttgggac  22140
attgacaatg agttttaa                                                22158
```

```
SEQ ID NO: 6            moltype = DNA  length = 106
FEATURE                 Location/Qualifiers
source                  1..106
                        mol_type = other DNA
                        organism = synthetic construct
SEQUENCE: 6
tagcctcctt tagaatttta accttagaag attagcatta gccaattgca tctggcgaat  60
cggacccaca agagcactga ggtcggaagt tcctattctc tagaaa                 106

SEQ ID NO: 7            moltype = DNA  length = 80
```

```
FEATURE                Location/Qualifiers
source                 1..80
                       mol_type = other DNA
                       organism = synthetic construct
SEQUENCE: 7
tcatcagtcc aggatacata gattaccaca actccgagcc tggttctcag cattcttttt  60
tccttactct gctatagaaa                                              80

SEQ ID NO: 8           moltype = RNA  length = 4911
FEATURE                Location/Qualifiers
source                 1..4911
                       mol_type = other RNA
                       organism = synthetic construct
SEQUENCE: 8
gtgcggaagg aagtgacgta gatccagagg gccggccggg gggtggggcc gagctataag  60
ctttgggtgg gaggcagcgc tgccttcaga aggcgtgcgg agcgcgggct gctgcattgc  120
ggactgtaga ggcgcttcct agtactccct tgtagcagct gagaatgatg gatcaagcca  180
gatcagcatt ctctaacttg tttggtgggg aaccattgtc atacacccgg tttagccttg  240
ctcggcaagt agatggagat aacagtcatg tggagatgaa actggctgca gatgaagaag  300
aaaatgccga caataacatg aaggctagtg tcagaaaacc caagaggttt aatggaagac  360
tctgctttgc agctattgca ctagtcattt tcttcttgat tggattcatg agtggctacc  420
tgggctattg taaaggggta gaaccaaaaa ctgagtgtga gagactggca ggaaccgagt  480
ctccagtgag ggaggagcca ggagaggact tccctgcagc acgtcgctta tattgggatg  540
acctgaagag aaagttgtcg gagaaactgg acagcacaga cttcaccggc accatcaagc  600
tgctgaatga aaattcatat gtccctcgtg aggctggatc tcaaaaagat gaaaatcttg  660
cgttgtatgt tgaaaatcaa tttcgtgaat ttaaactcag caaagtctgg cgtgatcaac  720
attttgttaa gattcaggtc aaagacagcg ctcaaaactc ggtgatcata gttgataaga  780
acggtagact tgtttacctg gtggagaatc ctgggggtta tgtggcgtat agtaaggctg  840
caacagttac tggtaaactg gtccatgcta attttggtac taaaaaagat tttgaggatt  900
tatacactcc tgtgaatgga tctatagtga ttgtcagagc agggaaaatc acctttgcag  960
aaaaggttgc aaatgctgaa agcttaaatg caattggtgt gttgatatac atggaccaga  1020
ctaaatttcc cattgttaac gcagaacttt cattctttgg acatgctcat ctggggacag  1080
gtgaccctta cacacctgga ttcccttcct tcaatcacac tcagtttcca ccatctcggt  1140
catcaggatt gcctaatata cctgtccaga caatctccag agctgctgca gaaaagctgt  1200
ttgggaatat ggaaggagac tgtccctctg actggaaaac agactctaca tgtaggatgg  1260
taacctcaga aagcaagaat gtgaagctca ctgtgagcaa tgtgctgaaa gagataaaaa  1320
ttcttaacat ctttggagtt attaaaggct ttgtagaacc agatcactat gttgtagttg  1380
gggcccagag agatgcatgg ggccctggag ctgcaaaatc cggtgtaggc acagctctcc  1440
tattgaaact tgcccagatg ttctcagata tggtcttaaa agatgggttt cagcccagca  1500
gaagcattat ctttgccagt tggagtgctg gagactttgg atcggttggt gccactgaat  1560
ggctagaggg ataccttttcg tccctgcatt taaaggcttt cacttatatt aatctggata  1620
aagcggttct tggtaccagc aacttcaagg tttctgccag cccactgttg tatacgctta  1680
ttgagaaaac aatgcaaaat gtgaagcatc cggttactgg gcaatttcta tatcaggaca  1740
gcaactgggc cagcaaagtt gagaaactca ctttagacaa tgctgctttc cctttccttg  1800
catattctgg aatcccagca gtttctttct gtttttgcga ggacacagat tatccttatt  1860
tgggtaccac catggacacc tataaggaac tgattgagag gattcctgag ttgaacaaag  1920
tggcacgagc agctgcagag gtcgctggtc agttcgtgat taaactaacc catgatgttg  1980
aattgaacct ggactatgag aggtacaaca gccaactgct ttcatttgtg agggatctga  2040
accaatacag agcagacata aaggaaatgg gcctgagttt acagtggctg tattctgctc  2100
gtggagactt cttccgtgct acttccagac taacaacaga tttcgggaat gctgagaaaa  2160
cagacagatt tgtcatgaag aaactcaatg atcgtgtcat gagagtggag tatcacttcc  2220
tctctcccta cgtatctcca aaagagtctc ctttccgaca tgtcttctgg ggctccggct  2280
ctcacacgct gccagcttta ctggagaact tgaaactgcg taaacaaaat aacggtgctt  2340
ttaatgaaac gctgttcaga aaccagttgg ctctagctac ttggactatt cagggagctg  2400
caaatgccct ctctggtgac gtttgggaca ttgacaatga gttttaaatg taacatgcat  2460
aattaaataa gagcagggta gtctgtttct agacttgtgt tggttgtgct aaattttcat  2520
tagagctcta aaatctaatg ttaaaattct acccaatcat ctaatgtctt aggcagcagc  2580
ttttagtgcg gggttggacc tacacttcaa gtacaatgga taacactttc catgtttgtg  2640
atatcttctc agattatctt taaaattttt gagtcctttg taataacttc ctctttgctt  2700
catggtcatg aaaatgtcag aaccagttgt aagaacaatg ctatatgtcc tgagggcatt  2760
aactagtgtc ttttgaggta ggagaaagag tgtgcttgtg gagggtcaac gtggtagttg  2820
ggtagttgga gattgccccg tctccatctg atcttccatt gagctgtatg cccttaagga  2880
tgtagctggt ttgcatttcc ctaaattaga cagtaacttt cagaagagat ggaacttgtt  2940
ttcttgccag caaggttgaa aataggtcct tagctggacc aatttgtctg tttacaggaa  3000
taagtaaggc cttactggtt aaccttggtg ttctttatga tgagaccaga agccaaagac  3060
ctcaagtttt ctctcctctt ggcatctgcc ctatagtctt tagttctttg tttttatttt  3120
gtttttcttt ttttcccaac attttctgaa aaagaacaag ttttagactc aatttgtcag  3180
acttgaaaag aacacactgc caagttttgg ccaaagtgtt agtcttcagg aaagctttct  3240
atcattttgg cactgagata tttattgttt atttatcagt gacagagttc actataaata  3300
gtgttgtttt tttttatat atagaagata attatcggaa gcagtgcctt ccataattat  3360
gacagttata ctgtcgtttt cttttaataa aagcagcatc tgctaatgag acccacagat  3420
actggaagtt ttgcacttat ggtcagcact tgcaacttta ggaaggaaga atgccacaat  3480
ccaaataata tgagctagaa gaggattggg ttaaataaga gattcctaat tgagttgggg  3540
aaaaaaatga tagttttcct aagtgcagtg agttgtggcc aagttaaatg tcatttaaag  3600
gctatggtag tacttacatc tacaaaattt tacagctcaa tttattcaag atgtaactca  3660
aaatcaattt tgcaaaattt ccagtacctt tgtcacaaac ttaactcaca ttatcgggag  3720
cagtgtcttc cataatgcat aaagaacaag gtagtttttg cctaccacag tgtctatatc  3780
ggagacagtg atctccatat gttacactaa gggtgtacgt aattatcggg aacagtgttt  3840
cccataattt tcttcatgca atgacatctt cagagcttga agatcgttag tatctaacat  3900
```

```
gaattcctaa cttcctgtag ctccttagtt ttagttgcaa aaaacatttg tggtcattga  3960
gcatttggtg ggtaaaatca actgctgtaa aatcattact tccaagatcc ttttttaaaa  4020
tgtgggtatt ttgttatctc tggtttatgg aataaaagca tacgtttata atgtttgctg  4080
gtgacaaagg aatttaacta tctccccttta tttgcatgtt acatgttatt tcctaaatgt  4140
agttcttaga agtttgaatt catttttggt ttttgggagg gtagaaagta gagaataatg  4200
ggtgttggga agacaaagct tgcaaaagga tctttatgta cctgctcatc actatggtgg  4260
ctatgaatta tgtaggtaat gagcaagatc acattaacaa agactagtta accatcatta  4320
cgcatctaat cagttttgcc atggggtcag ttcaaagctg ccacctgaga atgtcactag  4380
gctctcaggg tcttggcacc actcgcccaa gttatatcca ccagattatt ttgagcctca  4440
ctgagttgtt ttgctactca gtcccttcag tcttcacagt gtttctcttg taccagtatg  4500
agtatcaccg tgcataatgg gattccaagt cttgaatgaa ggcatgcatt ttacatagac  4560
gtctctgtga aataaccttt gttgtaagtg gtgtttccag tcaaagcagt aagttggtaa  4620
ggtttagtct tgggtgaaat gtggatctga gtaataagta gcttctgcta cttatcaggt  4680
tattgttggt taaaatgtag attttgaaga taaaaataga tcttttgtca tgactcactg  4740
ctagaatttg catgaccttt actgtgttag cttttgaatg ccttttggtt tggacttgcc  4800
aacctatact gtctttgctg aaatgccctt ataaatgtat acagctggta tgtaacaatg  4860
tgaagattcc ttacctgact taataaaata cttcgataat actgaaaaaa a            4911

SEQ ID NO: 9            moltype = AA  length = 760
FEATURE                 Location/Qualifiers
source                  1..760
                        mol_type = protein
                        organism = synthetic construct
SEQUENCE: 9
MMDQARSAFS NLFGGEPLSY TRFSLARQVD GDNSHVEMKL AADEEENADN NMKASVRKPK  60
RFNGRLCFAA IALVIFFLIG FMSGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                        760

SEQ ID NO: 10           moltype = DNA  length = 25
FEATURE                 Location/Qualifiers
source                  1..25
                        mol_type = other DNA
                        organism = synthetic construct
SEQUENCE: 10
agctagtgct gaagagtaag agcct                                         25

SEQ ID NO: 11           moltype = DNA  length = 25
FEATURE                 Location/Qualifiers
source                  1..25
                        mol_type = other DNA
                        organism = synthetic construct
SEQUENCE: 11
cacttgatgg tgccggtgaa gtctg                                         25

SEQ ID NO: 12           moltype = DNA  length = 20
FEATURE                 Location/Qualifiers
source                  1..20
                        mol_type = other DNA
                        organism = synthetic construct
SEQUENCE: 12
gctcgactag agcttgcgga                                               20

SEQ ID NO: 13           moltype = DNA  length = 24
FEATURE                 Location/Qualifiers
source                  1..24
                        mol_type = other DNA
                        organism = synthetic construct
SEQUENCE: 13
ggtgtctgtg agctgcctca cttg                                          24

SEQ ID NO: 14           moltype = DNA  length = 25
FEATURE                 Location/Qualifiers
source                  1..25
                        mol_type = other DNA
                        organism = synthetic construct
SEQUENCE: 14
ggtgagaaga aactaaacta tgcca                                         25

SEQ ID NO: 15           moltype = DNA  length = 22
```

```
FEATURE                Location/Qualifiers
source                 1..22
                       mol_type = other DNA
                       organism = synthetic construct
SEQUENCE: 15
tctggttcac ccaggttaga gc                                        22

SEQ ID NO: 16          moltype = DNA  length = 22
FEATURE                Location/Qualifiers
source                 1..22
                       mol_type = other DNA
                       organism = synthetic construct
SEQUENCE: 16
tcaccatctt ccaggagcga ga                                        22

SEQ ID NO: 17          moltype = DNA  length = 21
FEATURE                Location/Qualifiers
source                 1..21
                       mol_type = other DNA
                       organism = synthetic construct
SEQUENCE: 17
gaaggccatg ccagtgagct t                                         21

SEQ ID NO: 18          moltype = DNA  length = 21
FEATURE                Location/Qualifiers
source                 1..21
                       mol_type = other DNA
                       organism = synthetic construct
SEQUENCE: 18
ggatcggcca ttgaacaaga t                                         21

SEQ ID NO: 19          moltype = DNA  length = 22
FEATURE                Location/Qualifiers
source                 1..22
                       mol_type = other DNA
                       organism = synthetic construct
SEQUENCE: 19
cagaagaact cgtcaagaag gc                                        22

SEQ ID NO: 20          moltype = DNA  length = 25
FEATURE                Location/Qualifiers
source                 1..25
                       mol_type = other DNA
                       organism = synthetic construct
SEQUENCE: 20
agtaagacaa ggtgtgcacc catgt                                     25

SEQ ID NO: 21          moltype = DNA  length = 25
FEATURE                Location/Qualifiers
source                 1..25
                       mol_type = other DNA
                       organism = synthetic construct
SEQUENCE: 21
tcaggactga acttgggaag ttgag                                     25

SEQ ID NO: 22          moltype = DNA  length = 25
FEATURE                Location/Qualifiers
source                 1..25
                       mol_type = other DNA
                       organism = synthetic construct
SEQUENCE: 22
atataagcga cgtgctgcag ggaag                                     25

SEQ ID NO: 23          moltype = DNA  length = 23
FEATURE                Location/Qualifiers
source                 1..23
                       mol_type = other DNA
                       organism = synthetic construct
SEQUENCE: 23
aggccggtct cgaactccca acc                                       23

SEQ ID NO: 24          moltype = DNA  length = 25
FEATURE                Location/Qualifiers
source                 1..25
                       mol_type = other DNA
                       organism = synthetic construct
SEQUENCE: 24
gagccactgt acccagccag ctgat                                     25
```

-continued

```
SEQ ID NO: 25          moltype = DNA  length = 25
FEATURE                Location/Qualifiers
source                 1..25
                       mol_type = other DNA
                       organism = synthetic construct
SEQUENCE: 25
gacaagcgtt agtaggcaca tatac                                         25

SEQ ID NO: 26          moltype = DNA  length = 24
FEATURE                Location/Qualifiers
source                 1..24
                       mol_type = other DNA
                       organism = synthetic construct
SEQUENCE: 26
gctccaattt cccacaacat tagt                                          24

SEQ ID NO: 27          moltype = DNA  length = 22
FEATURE                Location/Qualifiers
source                 1..22
                       mol_type = other DNA
                       organism = synthetic construct
SEQUENCE: 27
ctctgctttg cagctattgc ac                                            22

SEQ ID NO: 28          moltype = DNA  length = 23
FEATURE                Location/Qualifiers
source                 1..23
                       mol_type = other DNA
                       organism = synthetic construct
SEQUENCE: 28
caggattctc caccaggtaa aca                                           23

SEQ ID NO: 29          moltype = DNA  length = 22
FEATURE                Location/Qualifiers
source                 1..22
                       mol_type = other DNA
                       organism = synthetic construct
SEQUENCE: 29
gttcgagagt caccacgctg ag                                            22

SEQ ID NO: 30          moltype = DNA  length = 22
FEATURE                Location/Qualifiers
source                 1..22
                       mol_type = other DNA
                       organism = synthetic construct
SEQUENCE: 30
ggcaaccctg atgactgaga tg                                            22

SEQ ID NO: 31          moltype = AA  length = 761
FEATURE                Location/Qualifiers
source                 1..761
                       mol_type = protein
                       organism = Rattus norvegicus
SEQUENCE: 31
MMDQARSAFS NLFGGEPLSY TRFSLARQVD GDNSHVEMKL AADEEENADS NMKASVRKPK  60
RFNGRLCFAT IAVVIFFLIG FMIGYLGYCK RVEQKEECVR LAEAEEADKS ENDETEYVPK  120
SSRLFWADLK TLLSEKLNSI EFTDIIKQLS QNTYTPREAG SQKDENLAYY IENLFHDFKF  180
SKVWRDEHYV KIQVKNSVSQ NLVTINSGSN IDPVEAPEGY VAFSKAGEVT GKLVHANFGT  240
KKDFEELNYS VNGSLVIVRA GKITFAEKVA NAQSFNAIGV LIYMDRNTFP VVEADLQFFG  300
HAHLGTGDPY TPGFPSFNHT QFPPSQSSGL PSIPVQTISR AAAEKLFKNM EGNCPPSWNI  360
DSSCKLELSQ NQNVKLTVNN VLKETRILNI FGVIKGYEEP DRYIVVGAQR DAWGPGVAKS  420
SVGTGLLLKL AQVFSDMISK DGFRPSRSII FASWTAGDYG AVGATEWLEG YLSSLHLKAF  480
TYINLDKVVL GTSNFKVSAS PLLYTLMGKI MQDVKHPIDG KYLYRDSNWI SKIEELSLDN  540
AAFPFLAYSG IPAVSFCFCE DEDYPYLGTK LDTYEILIQK VPQLNQMVRT AAEVAGQFII  600
KLTHDIELTL DYEMYNSKLL SFMKDLNQFK ADIKDMGLSL QWLYSARGDY FRATSRLTTD  660
FHNAEKTNRF VMREINDRIM KVEYHFLSPY VSPRESPFRH IFWGSGSHTL SALVENLRLR  720
QKNITAFNET LFRNQLALAT WTIQGVANAL SGDIWNIDNE F                        761
```